United States Patent
Newberry et al.

(10) Patent No.: US 11,241,480 B2
(45) Date of Patent: Feb. 8, 2022

(54) METHODS FOR MODULATION OF DIETARY AND MICROBIAL EXPOSURE WITH COMPOSITIONS COMPRISING AN EGFR LIGAND

(71) Applicants: Rodney Newberry, St. Louis, MO (US); Kathryn Knoop, St. Louis, MO (US); Keely McDonald, St. Louis, MO (US)

(72) Inventors: Rodney Newberry, St. Louis, MO (US); Kathryn Knoop, St. Louis, MO (US); Keely McDonald, St. Louis, MO (US)

(73) Assignee: Washington University, St. Louis, MO (US)

( * ) Notice: Subject to any disclaimer, the term of this patent is extended or adjusted under 35 U.S.C. 154(b) by 509 days.

(21) Appl. No.: 15/880,658

(22) Filed: Jan. 26, 2018

(65) Prior Publication Data
US 2018/0228868 A1  Aug. 16, 2018

Related U.S. Application Data

(60) Provisional application No. 62/450,831, filed on Jan. 26, 2017.

(51) Int. Cl.
| | | |
|---|---|---|
| *A61K 38/18* | (2006.01) | |
| *A61K 9/00* | (2006.01) | |
| *A61P 37/08* | (2006.01) | |
| *A61K 31/728* | (2006.01) | |

(52) U.S. Cl.
CPC ........ *A61K 38/1808* (2013.01); *A61K 9/0095* (2013.01); *A61K 31/728* (2013.01); *A61K 38/1841* (2013.01); *A61P 37/08* (2018.01)

(58) Field of Classification Search
None
See application file for complete search history.

(56) References Cited

U.S. PATENT DOCUMENTS

| | | | |
|---|---|---|---|
| 5,753,622 A | 5/1998 | Buret et al. | |
| 6,191,109 B1 * | 2/2001 | Besner | A61K 38/1808 424/551 |
| 6,531,134 B1 | 3/2003 | Dunbar et al. | |
| 2007/0243290 A1 | 10/2007 | Thompson et al. | |

(Continued)

FOREIGN PATENT DOCUMENTS

NZ        235556 A  *  6/1991  ............. A23C 11/00

OTHER PUBLICATIONS

Singh et al., EGF receptor ligands: recent advances, F1000Res., Version 1, 5(F1000 Faculty Rev):2270, Sep. 2016.*

(Continued)

*Primary Examiner* — Claire Kaufman

(57) ABSTRACT

Among the various aspects of the present disclosure is the provision of compositions and methods for modulation of dietary and microbial exposure. The present disclosure provides for compositions and methods for treating, preventing, or reducing the likelihood of development of an allergic disorder, necrotizing enterocolitis, sepsis, or an inflammatory disease, disorder, or condition in a subject including administering an effective amount of a composition comprising an EGFR ligand.

27 Claims, 41 Drawing Sheets
(39 of 41 Drawing Sheet(s) Filed in Color)
Specification includes a Sequence Listing.

(56) References Cited

U.S. PATENT DOCUMENTS

2011/0245171 A1 10/2011 Hardin et al.
2013/0244935 A1* 9/2013 Besner .............. A61K 38/177
514/9.6

OTHER PUBLICATIONS

Hill et al., Human milk hyaluronan enhances innate defense of the intestinal epithelium, J. Biol. Chem. 288:29090-29104, 2013.*
Nojiri et al.,Clinical significance of amphiregulin and epidermal growth factor in colostrum Arch. Gynecol. Obstet. 286:643-647, 2012.*
Jenerowicz et al., Environmental factors and allergic diseases, Annals Agri. Environ. Med. 19(3):475-481, 2012.*
Palomino et al., A multicenter, randomized, double-blind clinical trial examining th effect of oral human recombinant epidermal growth factor on the healing of duodendal ulcers, Scand. J. Gastroenterol. 35(10):1016-1022, 2000.*
Sullivan et al.,Intestinal mucosa remodeling by recombinant human epidermal growth factor 1_48 in neonates with severe necrotizing enterocolitis, J. Ped. Surg. 42:462-469, 2007.*
Dvorak et al., Comparison of epidermal growth factor and heparin-binding epidermal growth factor-like growth factors for prevention of experimental necrotizing enterocolitis, J. Ped. Gastroenterol Nutr., 47(1):11-18, 2008.*
Dvorak et al., Concentrations of EGF and TGF alpha in preterm milk, Adv Exp Med Biol, 554: 407-409, 2004.*
Nair et al., "Role of Epidermal growth factor and other growth factors in the prevention of necrotizing enterocolitis," Sem. Perinatol. 32(2):107-113, 2008.*
Okuyama et al., The effect of epidermal growth factor on bacterial translocation in newborn rabbits, J. Ped. Surg. 33(2):225-228, 1998.*
Ajayi et al., Pre-weaning and post weaning growth performance of rabbits:influence of genotype and litter size in a humid tropical environment, Intl. J. Agri. Forestry, 8(2):63-69, 2018.*
Beinzen-Derr et al., Role of human milk in extremely low birth weight infants risk of necrotizing enterocolitis or death, J. Perinatol. 29:57-62, 2009.*
Hamilton et al., The role of the epidermal growth factor receptor in sustaining neutrophil inflammation in severe asthma, Clin. Exp. Allergy, 33:233-240, 2003.*
Enomoto et al., Tissue remodeling induced by hypersecreted epidermal growth factor and amphiregulin in the airway after an acute asthma attack, J. Allergy Clin. Immuinol. 124(5):913-920, Nov. 2009.*
Sullivan et al., Epidermal growth factor in necrotising enteritis, The Lancet., vol. 338 Issue 8758, p. 53-54.Jul. 6, 1991.*
Opleta-Madsen et al., Epidermal growth factor and postnatal development of intestinal transport and membrane structure, Ped. Res. 30(4):342-350, 1991.*
O'Loughlin et al.., Effect of epidermal growth factor on ontogeny of the gastrointestinal tract, Am. J. Physiol. 249:G674-G678, 1985.*
Michalsky et al., Heparin-binding EGF-like growth factor is present in human amniotic fluid and breast milk, J. Ped. Surg. 37(1):1-6, 2002.*
Abrams et al., Food introduction and allergy prevention in infants, Canadian Medical Association Journal, 2015, pp. 1297-1301, vol. 187.
Adachi et al., Targeted disruption of the MyD88 gene results in loss of IL-1- and IL-18-mediated function. Immunity, 1998, pp. 143-150, vol. 9.
Adkins, Peripheral CD4+ lymphocytes derived from fetal versus adult thymic precursors differ phenotypically and functionally, Journal of Immunology, 2003, pp. 5157-5164, vol. 171.
Alvisi et al., Recommendations on complementary feeding for healthy, full-term infants, Italian Journal of Pediatrics, 2015, pp. 1-9, vol. 41.

Arpaia et al., Metabolites produced by commensal bacteria promote peripheral regulatory T-cell generation, Nature, 2013, pp. 451-455, vol. 504.
Atarashi et al., Induction of colonic regulatory T cells by Indigenous Clostridium species, Science, 2011, pp. 337-341, vol. 331.
Atarashi et al., TREG induction by a rationally selected mixture of Clostridia strains from the human microbiota, Nature, 2013, pp. 232-236, vol. 500.
Ballard et al., Human milk composition: nutrients and bioactive factors, Pediatric Clinics of North America, 2013, pp. 49-74, vol. 60.
Barnden et al., Defective TCR expression in transgenic mice constructed using cDNA-based alpha- and beta-chain genes under the control of heterologous regulatory elements, 1998, Immunol Cell Biol, pp. 34-40, vol. 76.
Bergstrom et al., Nature of bacterial colonization influences transcription of mucin genes in mice during the first week of life, BMC Research Notes, 2012, pp. 1-7, vol. 5.
Birchenough et al., Altered innate defenses in the neonatal gastrointestinal tract in response to colonization by neuropathogenic *Escherichia coli*, Infection and Immunity, 2013, pp. 3264-3275, vol. 81.
Birchenough et al., Postnatal development of the small intestinal mucosa drives age-dependent, region-selective susceptibility to *Escherichia coli* E1 infection, Scientific Reports, 2017 (Mar. 6), pp. 1-14, vol. 7.
Britton et al., Lumina hydrolysis of recombinant human epidermal growth factor in the rat gastrointestinal tract: segmental and developmental differences, Life Sciences, 1988, pp. 1339-1347, vol. 43.
Carey et al., Rapid Evolution of the CD8+ TCR Repertoire in Neonatal Mice, Journal of Immunology, 2016, pp. 2602-2613, vol. 196.
Carl, Sepsis from the gut: the enteric habitat of bacteria that cause late-onset neonatal bloodstream infections, Clinical Infectious Diseases, 2014, pp. 1211-1218. vol. 58, No. 9.
Chai et al., Helicobacter species are potent drives of colonic T cell responses in homeostasis and inflammation, Science Immunology, 2017 (Jul. 21), pp. 1-12, vol. 2.
Charbonneau et al., Sialylated Milk Oligosaccharides Promote Microbiota-Dependent Growth in Models of Infant Undernutrition, Cell, 2016, pp. 859-871, vol. 164.
Chieppa et al., Dynamic imaging of dendritic cell extension into the small bowel lumen in response to epithelial cell TLR engagement, The Journal of Experimental Medicine, 2006, pp. 2841-2852, vol. 203.
Chu et al., Gene-microbiota interactions contribute to the pathogenesis of inflammatory bowel disease, Science, 2016, pp. 1116-1120, vol. 352.
Cohavy et al., Colonic bacteria express an ulcerative colitis pANCA-related protein epitope, Infection and Immunity, 2000, pp. 1542-1548, vol. 68.
Cong et al., A dominant, coordinated T regulatory cell-IgA response to the intestinal microbiota, Proceedings of the National Academy of Sciences of the United States of America, 2009, pp. 19256-19261, vol. 106.
Desantis et al., Greengenes, a chimera-checked16S rRNA gene database and workbench compatible with ARB, Applied and Environmental Microbiology, 2006, pp. 5069-5072, vol. 72.
Du Toit et al., Randomized Trial on Peanut Consumption in Infants at Risk for Peanut Allergy, New England Journal of Medicine, 2015, pp. 803-813, vol. 372.
Du Toit et al., Effect of Avoidance on Peanut Allergy after Early Peanut Consumption, New England Journal of Medicine, 2016, pp. 1435-1443, vol. 374.
Eckburg et al., Diversity of the human intestinal microbial flora, Science, 2005, pp. 1635-1638, vol. 308.
Elinav et al., NLRP6 inflammasome regulate colonic microbial ecology and risk for colitis Cell, 2011, pp. 745-757, vol. 145.
Ermund et al., Studies of mucus in mouse stomach, small intestine, and colon. I. Gastrointestinal mucus layers have different properties depending on location as well as over the Peyer's patches, American Journal of Physiology-Gastrointestinal and Liver Physiology, 2013, pp. G341-G347, vol. 305.

(56) References Cited

OTHER PUBLICATIONS

Farache et al., Luminal bacteria recruit CD103+ dendritic cells into the intestinal epithelium to sample bacterial antigens for presentation, Immunity, 2013, pp. 581-595, vol. 38.
Fisk, Scientists working to help premature infants, Certified Crop Advisor, 2014, obtained from https://www.certifiedcropadviser.org/science-news/scientists-working-help-premature-infants on Apr. 27, 2018 (2 pages).
Furusawa et al., Commensal microbe-derived butyrate induces the differentiation of colonic regulatory T cells, Nature, 2013, pp. 446-450, vol. 504.
Gaboriau-Routhiau et al., The key role of segmented filamentous bacteria in the coordinated maturation of gut helper T cell responses, Immunity, 2009, pp. 677-689, vol. 31.
Gale et al., Is dietary epidermal growth factor absorbed by premature human infants?, Biology of the neonate, 1989, pp. 104-110, vol. 55.
Gilbert et al., Microbiome-wide association studies link dynamic microbial consortia to disease, Nature, 2016, pp. 94-103, vol. 535.
Gurnee et al., Gut Colonization of Healthy Children and Their Mothers With Pathogenic Ciprofloxacin-Resistant *Escherichia coli*, The Journal of Infectious Disease, 2015, pp. 1862-1868, vol. 212.
Hand et al., Acute gastrointestinal infection induces long-lived microbiota-specific T cell responses, Science, 2012, pp. 1553-1556, vol. 337.
Hapfelmeier et al., Microbe sampling by mucosal dendritic cells is a discrete, MyD88-independent step in ΔinvG S. Typhimurium colitis, Journal of Experimental Medicine, 2008, pp. 437-450, vol. 205.
Hogquist et al., T cell receptor antagonist peptides induce positive selection, Cell, 1994, pp. 17-27, vol. 76.
Hou et al., Toll-like receptors activate innate and adaptive immunity by using dendritic cell-intrinsic and -extrinsic mechanisms, Immunity, 2008, pp. 272-282, vol. 29.
Huijsdens et al., Quantification of bacteria adherent to gastrointestinal mucosa by real-time PCR, Journal of Clinical Microbiology, 2002, pp. 4423-4427, vol. 40.
Ivanov et al., Induction of Intestinal Th17 Cells by Segmented Filamentous Bacteria, Cell, 2009, pp. 485-498, vol. 139.
Jeon et al., A subpopulation of neuronal M4 muscarinic acetylcholine receptors plays a critical role in modulating dopamine-dependent behaviors, The Journal of Neuroscience, 2010, pp. 2396-2405, vol. 30.
Josefowicz et al. Extrathymically generated regulatory T cells control mucosal TH2 inflammation, Nature, 2012, pp. 395-399, vol. 482.
Kim et al., Regulatory T cells prevent catastrophic autoimmunity throughout the lifespan of mice, Nature Immunology, 2007, pp. 191-197, vol. 8.
Kim et al., In vivo structure/function and expression analysis of the CX3C chemokine fractalkine, Blood, 2011, pp. e156-e167, vol. 118.
Kim et al., Dietary antigens limit mucosal immunity by inducing regulatory T cells in the small intestine, Science, 2016, pp. 858-863, vol. 351.
Kim et al., Neonatal acquisition of Clostridia species protects against colonization by bacterial pathogens, Science, 2017 (Apr. 21), pp. 315-319, vol. 356.
Knoop et al., Microbial sensing by goblet cells controls immune surveillance of luminal antigens in the colon, Mucosal Immunology, 2014, pp. 198-210, vol. 8, No. 1.
Knoop et al., Antibiotics promote inflammation through the translocation of native commensal colonic bacteria, Gut, 2016, pp. 1100-1109, vol. 65.
Knoop et al., Antibiotics promote the sampling of luminal antigens and bacteria via colonic goblet cell associated antigen passages, Gut Microbes, 2017 (Jul. 4), pp. 1-12, vol. 8.
Kobata et al., High levels of growth factors in human breast milk, Early Human Development, 2008, pp. 67-69, vol. 84.
Koenig et al., Succession of microbial consortia in the developing infant gut microbiome, Proceedings of the National Academy of Sciences of the United States of America, 2011, pp. 4578-4585, vol. 108 Supplement 1.
Koplin et al., Can early introduction of egg prevent egg allergy in infants? A population-based study, The Journal of Allergy and Clinical Immunology, 2010, pp. 807-813, vol. 126.
Lathrop et al., Peripheral education of the immune system by colonic commensal microbiota, Nature, 2011. pp. 250-254, vol. 478.
Lee et al., Generation and validation of mice carrying a conditional allele of the epidermal growth factor receptor, Genesis, 2009, pp. 85-92, vol. 47.
Lindquist et al., Visualizing dendritic cell network in vivo, Nature Immunology, 2004, pp. 1243-1250, vol. 5.
Lodes et al., Bacterial flagellin is a dominant antigen in Crohn Disease, Journal of Clinical Investigation, 2004, pp. 1296-1306, vol. 113.
Marjou et al., Tissue-specific and inducible Cre-mediated recombination in the gut epithelium, Genesis, 2004, pp. 186-193, vol. 39.
Marra et al., Antibiotic use in children is associated with increased risk of asthma, Pediatrics, 2009, pp. 1003-1010, vol. 123.
Matsuoka, et al., The concentration of epidermal growth factor in Japanese mother's milk, Journal of Nutritional Science and Vitaminology, 1995, pp. 241-251, vol. 41.
Mazmanian et al., An Immunomodulatory molecule of symbiotic bacteria directs maturation of the host immune system, Cell, 2005, pp. 107-118, vol. 122.
Mazmanian et al., A microbial symbiosis factor prevents intestinal inflammatory disease, Nature, 2008, pp. 620-625, vol. 453.
McCuskey et al., Effect of milk-borne epidermal growth factor on the hepatic microcirculation and Kupffer cell function in suckling rats, Biology of the neonate, 1997, pp. 202-206, vol. 71.
McDole et al., Goblet cells deliver luminal antigen to CD103+ dendritic cells in the small intestine, Nature, 2012, pp. 345-349, vol. 483.
McDonald et al., Dendritic cells produce CXCL13 and participate in the development of murine small intestine lymphoid tissues, The American Journal of Pathology, 2010, pp. 2367-2377, vol. 176.
McDonald et al., Epithelial expression of the cytosolic retinoid chaperone cellular retinol binding protein II is essential for in vivo imprinting of local gut dendritic cells by luminal retinoids, American Journal of Pathology, 2012, p. 984-997, vol. 180.
Metsala et al., Mother's and offspring's use of antibiotics and infant allergy to cow's milk, Epidemiology, 2013, pp. 303-309, vol. 24.
Mosconi et al., Breast milk immune complexes are potent inducers of oral tolerance in neonates and prevent asthma development, Mucosal Immunology 2010, pp. 461-474, vol. 3.
Nagao-Kitamoto et al., Functional Characterization of Inflammatory Bowel Disease-Associated Gut Dysbiosis in Gnotobiotic Mice, Cellular and Molecular Gastroenterology and Hepatology, 2016, pp. 468-481, vol. 2.
Nelson et al., The Neonatal CD4+ T Cell Response to a Single Epitope Varies in Genetically Identical Mice, Journal of Immunology, 2015, pp. 2115-2121, vol. 195.
Ng et al., Microbiota-liberated host sugars facilitate post-antibiotic expansion of enteric pathogens, Nature, 2013, pp. 96-99, vol. 502.
Niess et al, CX3CR1-mediated dendritic cell access to the intestinal lumen and bacterial clearance, Science, 2005, pp. 254-258, vol. 307.
Nojiri et al., Clinical significance of amphiregulin and epidermal growth factor in colostrum, Archives of Gynecology and Obstetrics, 2012, pp. 643-647, vol. 286.
Nwaru et al., Age at the introduction of solid foods during the first year and allergic sensitization at age 5 years, Pediatrics, 2010, pp. 50-59, vol. 125.
Oguchi et al., Growth factors in breast milk and their effect on gastrointestinal development, 1997, Zhonghua Min Guo Xiao Er Ke Yi Xue Hui Za Zhi, pp. 332-337, vol. 38(5).
Ohnmacht et al., The microbiota regulates type 2 immunity through RORγt+ T cells, Science, 2015, pp. 989-993, vol. 349.
Olszak et al., Microbial exposure during early life has presistent effects on natural killer T cell function, Science, 2012, pp. 489-493, vol. 336.

(56) References Cited

OTHER PUBLICATIONS

Peignon et al., Complex interplay between beta-catenin signaling and Notch effectors in intestinal tumorigenesis, Gut, 2011, pp. 166-176, vol. 60.
Perkin et al., Randomized Trial of Introduction of Allergenic Foods in Breast-Fed Infants, New England Journal of Medicine, 2016, pp. 1733-1743, vol. 374.
Platts-Mills, The allergy epidemics: 1870-2010, The Journal of Allergy and Clinical Immunology, 2015, pp. 3-13, vol. 136.
Prescott et al., Transplacental priming of the human immune system to environmental allergens: universal skewing of initial T cell responses toward the Th2 cytokine profile, Journal of Immunology, 1998, pp. 4790-4737, vol. 160.
Qin et al., A human gut microbial gene catalogue established by metagenomic sequencing, Nature, 2010, pp. 59-65, vol. 464.
Quinton et al., Anti-*Saccharomyces cerevisiae* Mannan antibodies combined with antineutrophil cytoplasmic autoantibodies in inflammatory bowel disease prevalence and diagnostic role, Gut, 1998, pp. 788-791, vol. 42.
Rose et al., Excitatory neurons of the proprioceptive, interceptive, and arousal hindbrain networks share a developmental requirement for Math1, Proceedings of the National Academy of Sciences of the United States of America, 2009, pp. 22462-22467, vol. 106.
Round et al., Inducible Foxp3+ regulatory T-cell development by a commensal bacterium of the intestinal microbiota, Proceedings of the National Academy of Sciences of the United States of America, 2010, pp. 12204-12209, vol. 107.
Sefik et al., Individual intestinal symbionts induce a distinct population of RORγ+ regulatory T cells, Science, 2015, pp. 993-997, vol. 349.
Shaw et al., Association between the use of antibiotics in the first year of life and pediatric inflammatory bowel disease, The American Journal of Gastroenterology, 2010, pp. 2687-2692, vol. 105.
Shroyer et al., Intestine-Specific Ablation of Mouse atonal homolog 1 (Math1) Reveals a Role in Cellular Homeostasis, Gastroenterology, 2007, pp. 2478-2488, vol. 132.
Spahn et al., Modulating the intestinal immune system: the role of lymphotoxin and GALT organs, Gut, 2004, pp. 456-465, vol. 53.
Strachan et al., Hay fever, hygiene, and household size, The British Medical Journal, 1989, pp. 1259-1260, vol. 299.
Subramanian et al., Persistent gut microbiota immaturity in malnourished Bangladeshi children, Nature 2014, pp. 417-421, vol. 510.
Sun et al., Small intestine lamina propria dendritic cells promote de novo generation of Foxp3 T reg cells via retinoic acid, The Journal of Experimental Medicine, 2007, pp. 1775-1785, vol. 204.
Targan et al., Defects in mucosal immunity leading to ulcerative colitis, Immunological Reviews, 2005, pp. 296-305, vol. 206.
Turnbaugh et al., The human microbiome project, Nature, 2007, pp. 804-810, vol. 449.
Vallon-Eberhard et al., Transepithelial pathogen uptake into the small intestinal lamina propria, Journal of Immunology, 2006, pp. 2465-2469, vol. 176.
Verhasselt et al., Breast milk-mediated transfer of an antigen induces tolerance and protection from allergic asthma, Nature Medicine, 2008, pp. 170-175, vol. 14.
Von Mutius et al., Allergies, infections and the hygiene hypothesis—the epidemiological evidence, Immunobiology, 2007, pp. 433-439, vol. 212.
Why Formula Milk Should Be Illegal, Waisays, copyright 2000-2006, obtained from http://www.13.waisays.com/breastfeeding.htm on Apr. 27, 2018 (10 pages).
Worbs et al., Oral tolerance originates in the intestinal immune system and relies on antigen carriage by dendritic cells, Journal or Experimental Medicine, 2006, pp. 519-527, vol. 203.
Yatsunenko et al., Human gut microbiome viewed across age and geography, Nature, 2012, pp. 222-227, vol. 486.
Zheng et al., Regulatory T-cell suppressor program co-opts transcription factor IRF4 to control T(H)2 responses, Nature, 2009, pp. 351-356, vol. 458.
Zhou et al., TGF-beta-induced Foxp3 inhibits T(H)17 cell differentiation by antagonizing RORγt function, Nature, 2008, pp. 236-240, vol. 453.

\* cited by examiner

FIG. 3M-FIG. 3S
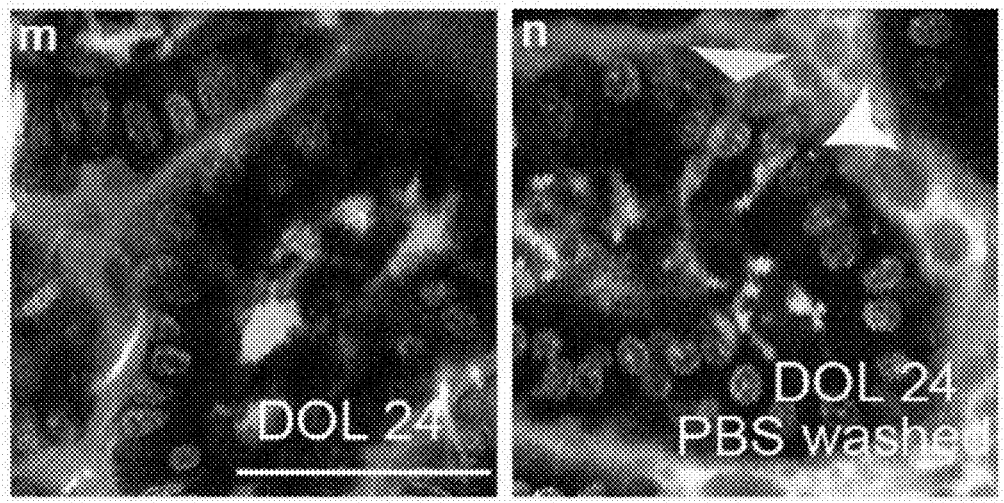
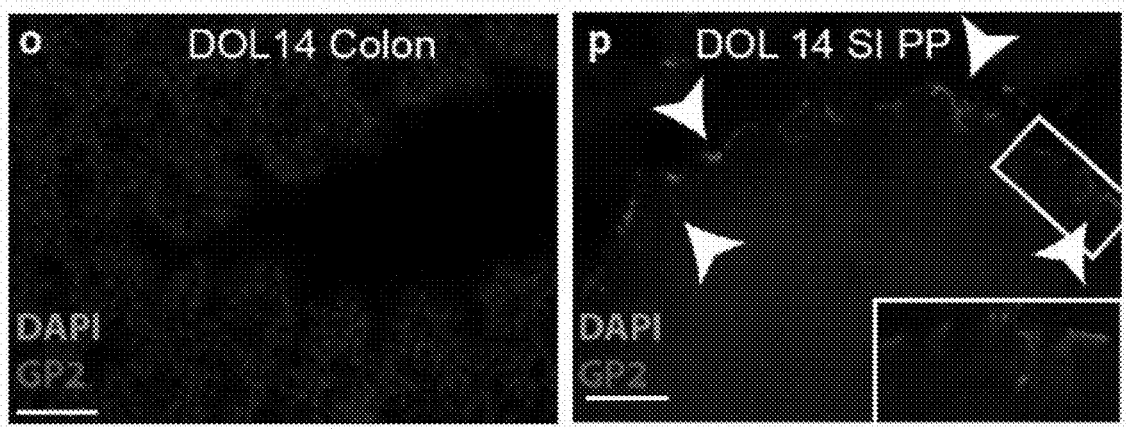
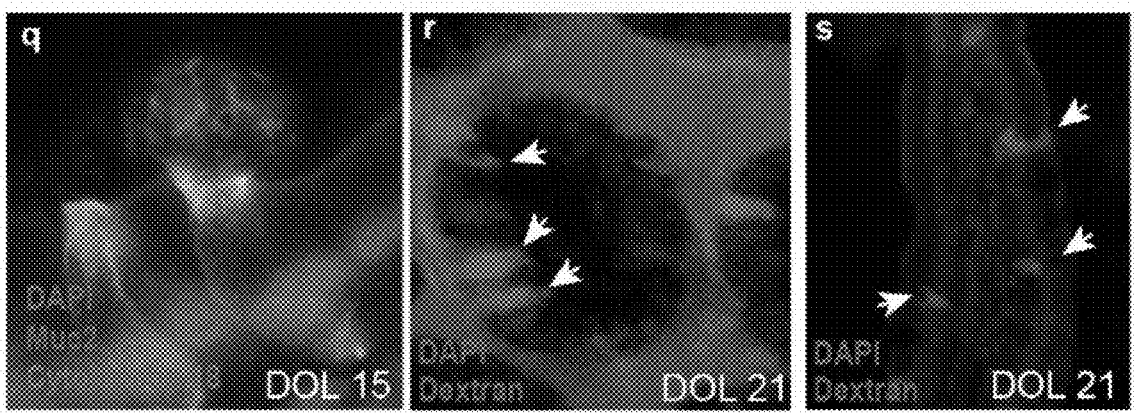

FIG. FIG. 16A-FIG. 16D
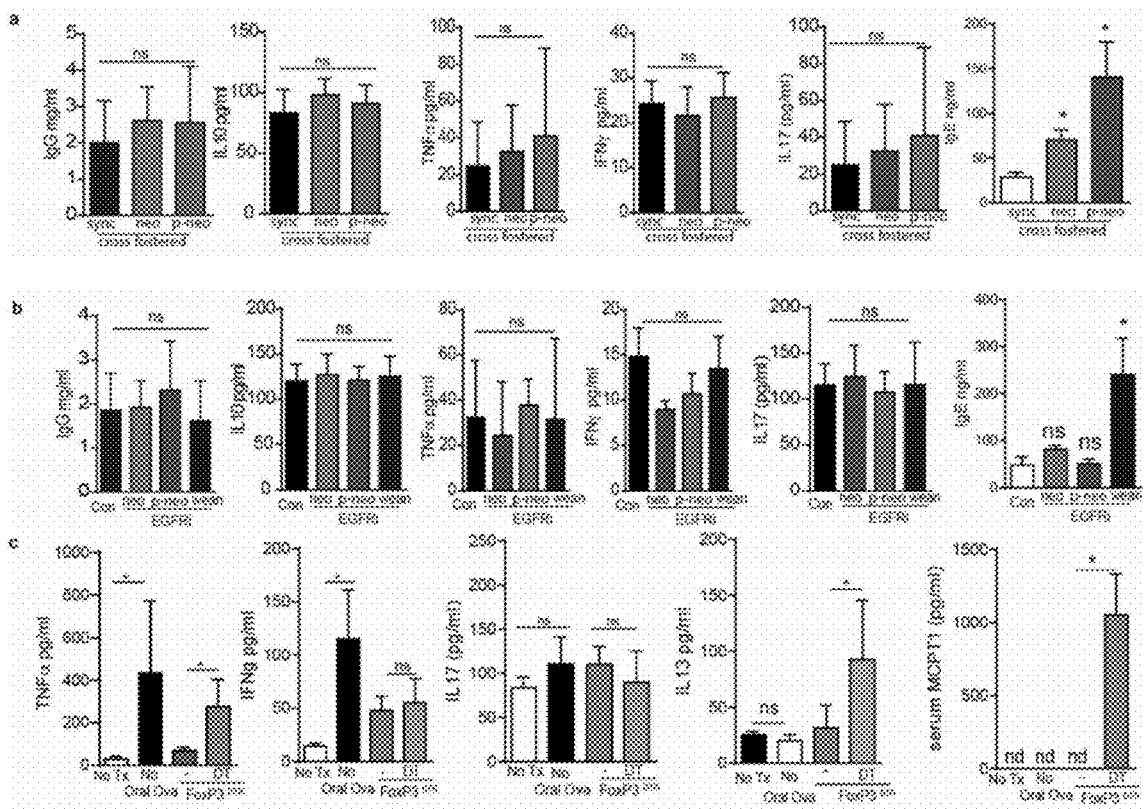

```
                          SEQUENCE LISTING

<160> NUMBER OF SEQ ID NOS: 38

<210> SEQ ID NO 1
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 1
caggtctccg agagggtact g                                             21

<210> SEQ ID NO 2
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 2
gctacggatg agccaaatga ag                                            22

<210> SEQ ID NO 3
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 3
gagcgagctg ggtaaagtag aaa                                           23

<210> SEQ ID NO 4
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 4
agccgaggca agaacaaaga                                               20

<210> SEQ ID NO 5
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 5
gtgagataca acgtagctga ctg                                           23

<210> SEQ ID NO 6
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 6
```
tcctgcatcc aagatagcaa gt                                           22

<210> SEQ ID NO 7
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 7
atggcatggc ttacaccacc                                              20

<210> SEQ ID NO 8
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 8
gaggccaatt ttgtctccac a                                            21

<210> SEQ ID NO 9
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 9
cggcctctgt tgggatgtt                                               19

<210> SEQ ID NO 10
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 10
gaccgcatgg cttcctcttc                                              20

<210> SEQ ID NO 11
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 11
tgagccaaga cagaaaaccc a                                            21

<210> SEQ ID NO 12
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 12
gggacatgag taaggttcct gtt                                          23

<210> SEQ ID NO 13
<211> LENGTH: 22
<212> TYPE: DNA

```
<213> ORGANISM: Artificial Sequence
<220> FEATURE:
<223> OTHER INFORMATION: Synthetic oligonucleotide

<400> SEQUENCE: 13
ggtaagggta agattggtgg tg                                              22

<210> SEQ ID NO 14
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 14
cgtcacaagg atagcttctg gaa                                             23

<210> SEQ ID NO 15
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 15
gaaaacatgc ccctcagtc a                                                21

<210> SEQ ID NO 16
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 16
cgtcacaagg atagcttctg gaa                                             23

<210> SEQ ID NO 17
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 17
tgccgtcctg tctacatctt tg                                              22

<210> SEQ ID NO 18
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 18
gttgctcagg ccagtcatca                                                 20

<210> SEQ ID NO 19
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 19
tcttcaagga tgtgaagtgt g                                               21
```

<210> SEQ ID NO 20
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 20
tgtacgcttt cgaacaatgt                                              20

<210> SEQ ID NO 21
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 21
agagtttgat catggctcag                                              20

<210> SEQ ID NO 22
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 22
actcctacgg gaggcagc                                                18

<210> SEQ ID NO 23
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 23
ccacccccta tgggtgccca                                              20

<210> SEQ ID NO 24
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 24
gcatgggtgg gggatcgcac                                              20

<210> SEQ ID NO 25
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 25
cactgatagt cccagggaac gcgc                                         24

<210> SEQ ID NO 26
<211> LENGTH: 24
<212> TYPE: DNA
<213> ORGANISM: Artificial Sequence
<220> FEATURE:

<223> OTHER INFORMATION: Synthetic oligonucleotide

<400> SEQUENCE: 26
atccacagcc atagccacaa gcac                                    24

<210> SEQ ID NO 27
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 27
atgcacgggc tgaacca                                            17

<210> SEQ ID NO 28
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 28
tcgttgttga aggacgggat a                                       21

<210> SEQ ID NO 29
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 29
tccagaccga gaaagagacc a                                       21

<210> SEQ ID NO 30
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 30
cccggatttt gctctccagt                                         20

<210> SEQ ID NO 31
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 31
gctgacacag gaaatcgatc g                                       21

<210> SEQ ID NO 32
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 32
gagagtatac atcacccgtc gcat                                    24

```
<210> SEQ ID NO 33
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 33
ggtgaatacg ttcccgg                                                   17

<210> SEQ ID NO 34
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 34
tacggctacc ttgttacgac tt                                             22

<210> SEQ ID NO 35
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 35
gctgacacag gaaatcgatc gt                                             22

<210> SEQ ID NO 36
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 36
gagagtatac atcacccgtc gcat                                           24

<210> SEQ ID NO 37
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 37
aagggagcgt agatggatg                                                 19

<210> SEQ ID NO 38
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 38
cgagcctcaa tgtcagttgc                                                20
```

METHODS FOR MODULATION OF DIETARY AND MICROBIAL EXPOSURE WITH COMPOSITIONS COMPRISING AN EGFR LIGAND

CROSS-REFERENCE TO RELATED APPLICATIONS

This application claims priority from U.S. Provisional Application Ser. No. 62/450,831 filed on 26 Jan. 2017, which is incorporated herein by reference in its entirety.

STATEMENT REGARDING FEDERALLY SPONSORED RESEARCH OR DEVELOPMENT

This invention was made with government support under grant number AI009550, DK097317, and DK097893 awarded by National Institutes of Health. The government has certain rights in the invention.

MATERIAL INCORPORATED-BY-REFERENCE

The Sequence Listing, which is a part of the present disclosure, includes a computer readable form comprising nucleotide and/or amino acid sequences of the present invention (016480-ORD1-1_Seq_Listing_ST25.txt created on 23 Jan. 2018, 7,833 bytes). The subject matter of the Sequence Listing is incorporated herein by reference in its entirety.

FIELD OF THE INVENTION

The present disclosure generally relates to compositions and methods for modulation of dietary and microbial exposure.

SUMMARY OF THE INVENTION

Among the various aspects of the present disclosure is the provision of compositions and methods for modulation of dietary and microbial exposure.

In one aspect, the present disclosure provides for treating, preventing, or reducing the likelihood of development of an allergic disorder in a subject including administering an effective amount of a composition comprising an epidermal growth factor receptor (EGFR) ligand.

In some embodiments, the EGFR ligand is administered to a human or other mammal to treat, prevent, or reduce the likelihood of development of an allergic disorder and an immune response is reduced. In some embodiments, the allergic disorder is a food allergy. In some embodiments, the EGFR ligand is administered to a human or other mammal to treat, prevent, or reduce the likelihood of development of necrotizing enterocolitis (NEC), sepsis (e.g., LOS or EOD), or an inflammatory disease, disorder, or condition (IBD, Crohn's disease, colitis).

In some embodiments, the method comprises oral administration of the composition comprising EGFR ligand.

In some embodiments, the subject is a human between about 0 days old (first day of life) and about 365 days old, about 18 months old (about 550 days old), about two years old, or weaning (the age at which the subject is weaned).

In some embodiments, the EGFR ligand administered to the subject decreases in concentration as the subject increases in age.

In some embodiments, the composition comprising EGFR ligand is administered to the subject at a concentration between about 0.02 µg/mL and about 0.2 µg/mL; or the subject is between about 0 days old (day of birth) and about 1 year of age, about 18 months of age, or about two years of age or between 0 days of age (first day of life) and about 140 days of age.

In some embodiments, the composition comprising EGFR ligand is administered to the subject in an oral formulation. In some embodiments, the oral formulation is selected from the group consisting of a food formulation, a powdered formulation, liquid formulation, liquid dispensed in a dropper bottle, a capsule, powdered infant formula, liquid concentrate infant formula, ready-to-use infant formula, parenteral hyperalimentation, donated breast milk, optionally with insufficient levels of EGF, supplement, powder, and drops.

In some embodiments, the EGFR ligand is selected from one or more of the group consisting of: EGF, transforming growth factor-α (TGFα), heparin-binding EGF-like growth factor (HB-EGF), amphiregulin (AR), betacellulin (BTC), epiregulin (EPR), hyaluronic acid, epigen, or other EGFR activators. In some embodiments, an effective amount of EGFR ligand: reduces immune response toward an antigen; modulates exposure to gut luminal substances; modulates colonic antigen uptake or antigen exposure; modulates luminal antigen delivery; reduces the translocation of gut bacteria; promotes development of regulatory T-cells restraining Th2 responses; promotes RORγt+ iTreg development and maintenance; or modulates Th2 related immunoglobulins and cytokines.

In another aspect, the present disclosure provides for a method of modulating dietary and microbial exposure in a subject comprising administering to the subject an effective amount of a composition comprising an EGFR ligand, wherein the subject has a disorder or may be at risk of developing a disorder selected from allergic disorder, necrotizing entercolotis, sepsis (e.g., late-onset sepsis (LOS), early-onset sepsis (EOS)), or an inflammatory disease, disorder, or condition (e.g., colitis, Crohn's disease, inflammatory bowel disease (IBD)).

In some embodiments, the EGFR ligand is administered to a human or other mammal to treat, prevent, or reduce a likelihood of developing an allergic disorder, optionally a food allergy.

In some embodiments, the composition is formulated in an oral formulation selected from the group consisting of: a food formulation, a powdered formulation, liquid formulation, liquid dispensed in a dropper bottle, a capsule, powdered infant formula, liquid concentrate infant formula, ready-to-use infant formula, donated breast milk, supplement, powder, and drops.

In some embodiments, the subject is between about 0 days old (first day of life) and about 550 days old (about 18 months old), about two years of age, weaning age (the age at which the subject is weaned), or comparable age for use in other mammals. In some embodiments, the composition comprising the EGFR ligand is administered to the subject decreases in concentration as the subject increases in age.

In some embodiments, modulating dietary and microbial exposure is in the gut.

In some embodiments, the EGFR ligand is selected from one or more of the group consisting of: EGF, transforming growth factor-α (TGFα), heparin-binding EGF-like growth factor (HB-EGF), amphiregulin (AR), betacellulin (BTC), epiregulin (EPR), hyaluronic acid, epigen, or an EGFR activator.

In some embodiments, an effective amount of EGFR ligand: reduces immune response toward an antigen; modulates exposure to gut luminal substances; reduces bacterial translocation; modulates colonic antigen uptake or antigen exposure; modulates luminal antigen delivery; promotes development of regulatory T-cells restraining Th2 responses; promotes RORγt+ iTreg development and maintenance; or modulates Th2 related immunoglobulins and cytokines.

In another aspect, the present disclosure provides for a method for treating, preventing, or reducing a likelihood of development of necrotizing enterocolitis (NEC), sepsis, or an inflammatory disease, disorder, or condition in a subject in need thereof, the method comprising: administering an effective amount of a composition comprising an EGFR ligand to the subject.

Other objects and features will be in part apparent and in part pointed out hereinafter.

DESCRIPTION OF THE DRAWINGS

The patent or application file contains at least one drawing executed in color. Copies of this patent or patent application publication with color drawing(s) will be provided by the Office upon request and payment of the necessary fee.

Those of skill in the art will understand that the drawings, described below, are for illustrative purposes only. The drawings are not intended to limit the scope of the present teachings in any way.

(FIG. 1A) Quantitative increase in footpad thickness in the DTH assay and (FIG. 1B) representative images of footpads in mice given drinking water alone or dietary Ova as on DOL 0-10, DOL 11-21, DOL 28-38 (after weaning), or as adults on DOL 42-52. (FIG. 1C) Luminal antigen presentation capacity of SI and colon APCs isolated from the LP of mice of various ages given dietary Ova as assessed by the increase in Ova specific OTI T-cells 72 after hours of culture. (FIG. 1D and FIG. 1E) Single optical section from Z-stacks during in vivo 2P imaging taken 15 μM beneath the SI villous surface or 10 μM beneath the colonic surface after administering luminal 10 kD dextran (red) and DAPI (blue). GAPs (arrows) are rare in the SI but common in the colons of mice at DOL 18 (yellow arrowheads denote GAPs on the surface epithelium, white arrowheads denote GAPs in the crypt epithelium). (FIG. 1F) Three-dimensional reconstruction from 2P imaging of the mouse colon at DOL 18 demonstrating the appearance of colonic GAPs (green; dextran) that fill from the lumen. (FIG. 1G) Fixed tissue stained after 2P imaging demonstrates the presence of dextran-filled cytokeratin 18 (cyt18$^+$) epithelial cells with GC morphology in the colon at DOL18 (inset, single channels of cyt18$^+$ and dextran+ cells). (FIG. 1H) 3D reconstruction of confocal images with single slices in the x-y-z dimensions from the colon of a DOL 18 CX$_3$CR1$^{GFP}$ reporter mouse demonstrating LP-APCs (green) interacting with a dextran (red) filled GAP; nuclei (blue). (FIG. 1I) Number of GAPs per colonic crypt or SI villus in early life as assessed by 2P imaging in specific pathogen free housed (SPF) or germfree housed (GF) mice. (FIG. 1J and FIG. 1K) Single optical section from Z-stacks during in vivo 2P imaging taken 10 μm beneath the colonic surface after administering luminal 10 kD dextran (green) and DAPI (blue) demonstrating the j) absence of GAPs in DOL 18 Math1$^{i\Delta vil}$ mice lacking goblet cells, and (FIG. 1I) their presence in Math1$^{fl/flcre-}$ littermates, which have GCs. (FIG. 1L) Luminal antigen presentation capacity of colon APCs from the LP of Math1$^{i\Delta vil}$ mice or Math1$^{fl/flCre-}$ littermates at DOL 18 following luminal PBS or luminal Ova, or when exogenous Ova was added directly to the culture as assessed by the increase in Ova specific OTI T-cells after 72 hours of culture. (FIG. 1M) Number of colonic or SI GAPs in mice on DOL 8, 15, or 28 in the presence or absence of the cholinergic agonist CCh (c) or mAChR4 blockade with tropicamide (t). Data are presented as the mean+/−SEM, *=p<0.05, ND=not detected, ns=not significant, n=4 mice or more per time point in FIG. 1A and FIG. 1I-FIG. 1M, FIG. 1B-FIG. 1E are representative of 5 or more mice in each group, FIG. 1G-FIG. 1H are representative of 3 mice, scale bar=50 μm in FIG. 1B and FIG. 1G and 25 μm in panel FIG. 1E.

FIG. 3A-FIG. 3U is a series of images showing paracellular leak, trans-epithelial dendrite (TED) extension by DCs, and villous M cells do not correlate with the temporal and regional pattern of antigen delivery across the gut epithelium in early life. (FIG. 3A-FIG. 3F) 2-photon imaging of the GI tract reveals paracellular leak (white arrowheads) of 3 kD rhodamine dextran (red) around epithelial cells (DAPI, blue) and flow into the lamina propria (white arrowheads) in the small intestine, and to a lesser extent in the colon at all time points examined. GAPs in the colon at DOL 14 are denoted by yellow arrowheads. (FIG. 3G-FIG. 3L) 2-photon imaging of CX3CR1$^{GFP/+}$ mice reveals trans-epithelial dendrites (TEDs) were very rare in the gastrointestinal tract in early life in the steady state. (FIG. 3M-FIG. 3N) TEDs (white arrow) in the SI of weaned mice become more common following removal of luminal contents with gentle washing with 5×1 mL of 37° C. PBS. (FIG. 3O-FIG. 3P) Immunofluorescence staining of the (FIG. 3O) colon and (FIG. 3P) SI Peyer's patch (PP) from DOL 14 mice demonstrates a lack of GP-2+ M cells on the colonic epithelium and their presence in the follicle associated epithelium of the PP. (FIG. 3Q) the SI of mice on DOL15 contains GCs identified as Muc2+ cytokeratin 18+ epithelial cells, however GAPs, identified as epithelial cells with a GC morphology acquiring luminal 10 kD fluorescent dextran during (FIG. 3R) in vivo 2P imaging or on (FIG. 3S) fixed tissue sections become more prevalent later in life. Fixed tissue sections following the luminal administration of fluorescent 10 kD dextran demonstrates that the (FIG. 3T) proximal colon on DOL 35 lacks GAPs, but (FIG. 3U) the most distal 2 cm of colon of adult mice contains a few GAPs as identified by epithelial cells acquiring luminal 10 kD fluorescent dextran. FIG. 3A-FIG. 3S are representative images from n=3 mice for each condition. FIG. 3T-FIG. 3U are representative images of n=4 mice. Scale bar=50 μm.

(FIG. 5A) Quantitative RTPCR analysis of sorted GCs (CD45-CD24-UEA1+CK18+) from DOL 18 mouse SI or colon reveals expression of TLRs, Myd88, and EGFR. (FIG. 5B) Number of colonic GAPs in DOL 18 SPF housed mice, DOL 18 GF mice, DOL 18 Myd88−/− mice and DOL 18 My88$^{fl/fl}$ Math 1 mice treated with RU486 to delete Myd88 in GCs, in the presence or absence of heat killed cecal contents from an adult SPF housed mouse. (FIG. 5C) Number of colonic GAPs in DOL 18 mice treated with luminal LPS in the presence or absence of inhibitors of EGFR activation (EGFRi) or p42/p44 MAPK activation (MAPKi). (FIG. 5D) number of colonic GAPs in DOL 18 Myd88−/− mouse in the presence or absence of stomach contents from a mouse at 10 DOL (SC) or 100 ng EGF (EGF). n=4 mice per group. Data is presented as mean+/−SEM, *=p<0.05, ns=not significant, nd=not detected.

(FIG. 6A) Quantitative real time PCR using universal primers for bacterial 168 rDNA demonstrates a dramatic expansion of the colonic microbial load between DOL 10-30. (FIG. 6B) 168 sequencing to characterize the cecal microbial community and (FIG. 6C) quantitative real time PCR demonstrates a bloom of Clostridia species associated with tolerance induction prior to DOL 24, which coincides with the presence of colonic GAPs. (FIG. 6D) Principal component analysis of the cecal microbial community determined by 168 sequencing throughout early life and adulthood. (FIG. 6E) Quantitative real time PCR for CBir1 antigen by DOL, red arrow indicates time of CBir1 specific T cell transfer in post-neonatal mice in FIG. 5E, green arrow indicates time of CBir1 specific T cell transfer in adults in FIG. 5E. n=4 per group. Data is presented as mean+/−8EM, *=p<0.05, nd=not detected.

(FIG. 8A) Density of colonic GAPs in mice at DOL 18 treated with PBS or luminal stomach contents (SC) obtained from mice at DOL 10 in the presence or absence of inhibitors of EGFR (EGFRi) or p42/p44 MAPK (MAPKi). (FIG. 8B) Density of colonic GAPs 10 days after CF of newborn mice to dams 15 day post-partum (pp) or mice at DOL 15 CF to dams 1 day pp. (FIG. 8C and FIG. 8D) Number of GAPs per GC and luminal concentration of EGF in the (FIG. 8C) SI or (FIG. 8D) colon through early life. (FIG. 8E) EGF concentration in stools obtained from healthy formula fed or healthy breast fed humans through the first year of life. (FIG. 8F and FIG. 8G) Immunohistochemistry of GAPs (red) in the colon of mice at DOL 19 in the (FIG. 8F) absence or (FIG. 8G) presence of luminal EGF. (FIG. 8H) Density of colonic GAPs at DOL 18 15 minutes after administering luminal EGF. (FIG. 8I-FIG. 8K) Immunohistochemistry of phosphorylated EGFR (red) and cyt18 (green) in the colons on (FIG. 8I) DOL 8, (FIG. 8J) DOL 18, or (FIG. 8K) DOL 28 after weaning. (FIG. 8L) Luminal antigen presentation capacity of colon LP-APCs from DOL 18 mice following intrarectal PBS or Ova in the presence or absence of concurrent luminal EGF or systemic mAChR$_4$ blockade (tropicamide; trop) as assessed by the increase in Ova specific OTI T-cells following 72 hours of culture. (FIG. 8M) Number of GAPs in the SI or colon at DOL 8, DOL 18, or DOL 28, in the presence or absence of EGFRi. Data are presented as the mean+/−SEM, *=p<0.05, ND=not detected, ns=not significant, n=5 per group for panel a, n=4 mice or more per time point for FIG. 8B-FIG. 8D. FIG. 8E represents data from 42 stool specimens from 6 breast fed children and 53 stool specimens from 7 formula fed children. FIG. 8F and FIG. 8G are representative of 3 independent experiments with 2 or more mice in each group. n=4 mice per group for FIG. 8H-FIG. 8M. Scale bar=50 μm for panels FIG. 8F and FIG. 8I.

(FIG. 9A) ELISAs on stomach, SI, and colon contents through early life demonstrates a proximal to distal gradient of EGF that declines in early life. (FIG. 9B) DTH responses as measured by increase in footpad thickness in mice given Ova enemas every other day from DOL 14-22 (post-neonatal phase; p-neo) or from DOL 56-64 (adult) with or without EGF demonstrates that luminal EGF attenuates tolerance to a luminal antigen when given in the colonic lumen during the post-neonatal phase. n=4 mice per group in FIG. 9A, n=5 per group in FIG. 9B. Data is presented as mean+/−SEM, *=p<0.05, ns=not significant.

(FIG. 10A) Colonic naïve (CD62L+) T-cell and Treg (FoxP3$^+$) populations in early life assessed by flow cytometry, inset demonstrates the majority of Tregs at DOL 24 are Helios− iTregs with a large RORγt+ population. (FIG. 10B) The number of Tregs (Foxp3$^+$ IL-10$^+$) and Th17 (IL17$^+$ IL10$^−$) Ova specific CD4$^+$ OTII T-cells following 6 days of culture with Ova and cellular populations isolated from the intestines of mice at DOL 18. (FIG. 10C-FIG. 10D) Ova specific OTII T-cells adoptively transferred on DOL15 or DOL 56 were (FIG. 10C) preferentially localized to the colon of post-neonatal phase (p-neo) mice receiving dietary Ova (FIG. 10D) and differentiated into FoxP3+ IL-10+ cells. (FIG. 10E) CBir1 transgenic T-cells specific for a commensal bacterial antigen localized to the colon and differentiated into FoxP3+ when adoptively transferred in post-neonatal phase (DOL 21) but not when transferred in adult mice (DOL 56). (FIG. 10F) Colonic FoxP3 T-cell population through early life in mice after CF DOL 1 pups to dams 14 days pp (neonatal phase; neo CF), DOL 14 pups to dams one day pp (post-neonatal phase; p-neo CF), and DOL 1 pups to dams one day pp (synchronous; sync CF). (FIG. 10G) Colonic FoxP3 T-cell population through early life in and (FIG. 10H) ratio of iTregs (Helios−) to nTregs (Helios+) in the colonic LP at DOL 28 in mice given EGFR inhibition (EGFRi) during the neonatal phase (DOL 6 and 8; neo), post-neonatal phase (DOL 14 and 16; p-neo), or weaning phase (DOL 24 and 26; wean). Expression of RORγt or Helios in FoxP3+ cells and the ratio of iTregs (Helios−) to nTregs (Helios+) in the colon LP of mice at 8 months of age following (FIG. 10I and FIG. 10J) synchronous CF or asynchronous CF during the neonatal or post-neonatal phases as outlined in FIG. 10F, or FIG. 10K and FIG. 10L following EGFRi during the neonatal, post-neonatal, or weaning phases as outlined in FIG. 10G. Data are presented as the mean+/−SEM, *=p<0.05, ND=not detected, ns=not significant, n=4 mice per time point or group in FIG. 10A, FIG. 10C, FIG. 10F, and FIG. 10G, FIG. 10B is representative of 2 independent experiments with n=3 for each condition, FIG. 10D -FIG. 10E is representative of 2 independent experiments with n=4 for each group; n=5 or more mice per group in FIG. 10I-FIG. 10L.

(FIG. 11A) Flow cytometry of the colonic LP cellular population at DOL 14 demonstrates a significant population of CD62L+CD69− CD44− naive CD4 T cells, which become rare in adulthood. (FIG. 11B) The colon contains a prominent population of CD4+FoxP3+ Tregs that are Helios− and RORγt+ on DOL 24, which persists but becomes smaller in adulthood. (FIG. 11C) Three dimensional reconstructions of Z-stacks taken from the surface of the colonic epithelium extending SO µm into the lamina propria of DOL18 (post-neonatal phase; p-neo) and DOL 28 (weaning phase; wean) $CD11c^{YFP}$ reporter mice demonstrate that $CD11c^{YFP+}$ cells associate with the epithelium during the post-neonatal phase. (FIG. 11D) quantitation of the number of $CD11c^{YFP+}$ cells near the epithelium in FIG. 11C. (FIG. 11E) flow cytometry analysis of the CD11c+ MHCII+ population isolated with the colonic LP or epithelial fraction on DOL 18 in $Math^{iΔil}$ mice treated with tamoxifen to delete GCs or littermate controls demonstrates a reduction in the CD11c+ MHCII+ population preferentially affecting epithelial associated (EA) CD11c+ MHCII+ cells. (FIG. 11F) flow cytometry analysis of Aldefluor+ (ALDH activity) CD11c+ MHCII+ cells in the colonic LP of DOL 8 (neonatal phase;neo), DOL 18 (post-neonatal phase; p-neo), or DOL 28 (weaning phase; wean) mice demonstrates an increase in Aldeflour+ cells in the post-neonatal phase coinciding with the presence of colonic GAPs. Plots in FIG. 11A and FIG. 11B are representative of n=4 mice per group. Images in FIG. 11C are representative from n=3 mice. n=3 or more mice per group in FIG. 11D-FIG. 11F. Data is presented as mean+/−SEM, *=p<0.05.

(FIG. 12A) naive CDS+ T cells traffic to the colon in the post-neonatal phase in response to oral antigen and (FIG. 12B) CSFE labelled OTI T cells can be visualized near the colonic epithelium in the post-neonatal phase in mice receiving dietary Ova. (FIG. 12C) Intracellular cytokine staining of adoptively transferred Ova specific OTII T cells in mice given dietary Ova demonstrates that they preferentially become Foxp3+ IL-10 producing Tregs in the colon in the post-neonatal phase. (FIG. 12D) Adoptively transferred CBir1 T cells preferentially localize to the colon and (FIG. 12E) become Foxp3+ in the post-neonatal phase. n=4 mice per group, images are representative of n=4 mice. Data is presented as mean+/−SEM, *=p<0.05, ns=not significant.

(FIG. 13A-FIG. 13D) Mice synchronously CF or asynchronously CF in the neonatal (neo) or post neonatal (p-neo) phases as in FIG. 8F or FIG. 8E-FIG. 8H. Mice receiving EGFRi in the neonatal (neo; DOL 6 and 8), post-neonatal (p-neo; DOL 14 and 16) or weaning (wean; DOL 24 and 26) phases were given Ova in drinking water on DOL 0-30 and immunized parenterally against Ova as adults. (FIG. 13A and FIG. 13E) Quantitative increase in footpad thickness following rechallenge with Ova four months later. (FIG. 13B and FIG. 13F) Serum Ova specific IgE, (FIG. 13C and FIG. 13G) serum IL-13, and (FIG. 13D and FIG. 13H) serum eotaxin as measured by ELISA three months after footpad challenge. (FIG. 13I-FIG. 13K) $FoxP3^{DTR}$ mice were given Ova in drinking water on DOL 0-30 mice, injected with PBS or diphtheria toxin (DT) on DOL 21 and 23 to delete Tregs, immunized parenterally against Ova as adults, and rechallenged with Ova in the footpad. (FIG. 13I) Increase in footpad thickness following rechallenge with Ova. (FIG. 13J) Absolute number of FoxP3+CD4 T-cells and (FIG. 13K) ratio of iTregs to nTregs in colon LP of $FoxP3^{DTR}$ mice 5 days and 3 months after DT treatment. (FIG. 13L-FIG. 13M) Mice were treated with EGFRi during the neonatal, post-neonatal, or weaning phases as above, or treated with PBS in the post-neonatal phase, or $FoxP3^{DTR}$ mice were injected with DT at DOLs 21 and 23 to delete Tregs, given Ova in drinking water as adults (DOL 40-50), immunized parenterally with Ova, and rechallenged with Ova in the footpad. (FIG. 13L) Increase in footpad thickness following rechallenge with Ova. (FIG. 13M) Change in body temperature following footpad challenge with Ova. (FIG. 13N) Serum IL-13 and (FIG. 13O) serum mast cell protease 1 (MCPT1) 48 hours after rechallenge as measured by ELISA. Data are presented as the mean+/−SEM, *=p<0.05, ns=not significant, FIG. 13A -FIG. 13H is representative of one of two independent experiments with n=5 or more mice per group, n=5 mice in each group for data in FIG. 13I-FIG. 13O.

(FIG. 15A and FIG. 15B) Mice were given Ova in drinking water from days 0-30 of life and underwent a DTH assay with rechallenge as adults. (FIG. 15A) Mice with colonic GAPs manipulated in early life by injection with an inhibitor of EGFR activation during the neonatal phase (neo; DOL 6 and 8) or the weaning phase (wean; DOL 24 and 26), but not during the post-neonatal phase (p-neo; DOL 14 and 16, which does not alter colonic GAPs) developed hypothermia upon rechallenge with subcutaneous sterile Ova in the DTH model. (FIG. 15B) Mice with colonic GAPs manipulated by asynchronous cross fostering (CF) as outlined in FIG. 8F, but not mice without colonic GAP manipulation (synchronous CF) nor mice without colonic GAP manipulation not exposed to dietary Ova, developed hypothermia upon rechallenge with subcutaneous sterile Ova in DTH model. Control mice in (FIG. 15A) received dietary Ova from days 0-30 of life and an injection of PBS on DOL 14 and 16. (FIG. 15C) Mice were given drinking water alone or drinking water with Ova with and without antibiotics (ABX; ampicillin, metronidazole, neomycin, and vancomycin) between DOL 10-20 and challenged with a DTH assay as adults. Mice given antibiotics showed an impaired ability to be tolerized to dietary Ova as evidenced by enhanced footpad swelling upon rechallenge. (FIG. 15A-FIG. 15F) Mice given Ova in drinking water from DOL 0-30 without (control; con) or with antibiotics in drinking water DOL 0-10 (neo), DOL 10-20 (p-neo), or DOL 20-30 (wean), were immunized as adults and challenge with subcutaneous Ova in the footpad. Mice receiving antibiotics between DOL 10-20 and DOL 20-30 had (FIG. 15D) increased footpad swelling, indicative of impaired oral tolerance, (FIG. 15E) hypothermia upon challenge with subcutaneous Ova, (FIG. 15F) and persistent decreases in the colonic iTreg population at 8 months of age. n=4 or more mice per group. Data is presented as mean+/−SEM, *=p<0.05 when compared with controls. ns=not significant.

FIG. 16A-FIG. 16D is a series of bar graphs showing altering the timing of colonic GAP opening in early life leads to selective elevations of Th2 related immunoglobulins and cytokines. Serum IgG, IgE, and non-Th2 cytokine levels in 8 month old mice with alterations in colonic GAPs by (FIG. 15A) cross fostering, as outlined in FIG. 8F, or (FIG. 15B) by inhibiting EGFR activation in early life, as outlined in FIG. 8G. (FIG. 15C) Serum cytokine levels in 4 month old mice with no treatment (no tx), never orally tolerized to ova but immunized against ova (no oral ova), or FoxP3° rn mice treated or not treated with DT on day 21, 23 of life given Ova in drinking water on DOL 0-30 followed by systemic immunization against Ova. (FIG. 15D) Multiplex cytokine analysis on serum from 8 month old mice with alterations in colonic GAPs by cross fostering or inhibition of EGFR activation as outlined in FIG. 8F and FIG. 8G. Pattern of differences between the groups is as shown in FIG. 13C, FIG. 13D, FIG. 13G, and FIG. 13H. n=3 or more mice per group. Data is presented as mean+/−SEM, *=p<0.05, ns=not significant.

(FIG. 23A) Fold increase in CBir1 T cells after ex vivo culture with LP-MNPs isolated from the SI or colon on DOL7, 14, 21, or 28. (FIG. 23B) Percent of (CD45.1+) CBir1 T cells of total CD4+ T cells or (FIG. 23C) percent of proliferating CBir1 T cells of the total CD45.1+ CBir1 T cells within the SI or colon draining MLNs three days following transfer into recipient CD45.2 mice on DOL 7,17, or 27. (FIG. 23D) Percent of (CD45.1+) DP1 T cells of CD4+ T cells within the MLNs three days following transfer. (FIG. 23E) Percent of CD45.1 cells of the total CD4+CD3+ T cell population or (FIG. 23F) percentage of Foxp3+ cells of the CD45.1+ cells in the colon LP seven days following transfer of CD45.1+ CBir1, DP1 or OTII T cells into recipient mice not receiving ovalbumin; DOL represents day of transfer. (FIG. 23G) Percentage of LP-MPNs staining for luminally administered Ova-647 on DOL7, 14, 21, or 28. (FIG. 23H) 4 kD FITC dextran in serum following gavage in DOL18 GC knockout and littermate control mice. (FIG. 23I) Percentage of LP-MNPs staining for luminally administered Ova-647 in DOL18 GC knockout and littermate control mice (FIG. 23J) Percent of CD45.1+ CBir1 cells of CD4+ T cells within the MLNs three days following transfer into DOL18 GC knockout and littermate control mice. (FIG. 23M) Ratio of GAPs per GC in the SI and colon from DOL7-60. *=p<0.001, ns=not significant, n=4 mice per group. Experiments in FIG. 23B, FIG. 23C, FIG. 23G, FIG. 23H, and FIG. 23K were repeated two independent times.

(FIG. 23A) Representative flow plots identifying transferred and proliferating CBir1 T cells in the colon draining MLN in DOL20 mice. (FIG. 23B) representative flow cytometry plots identifying Foxp3 expression by transferred CBir1 T cells in the colon LP on DOLE, 18, and 28. (FIG. 23C) Representative flow cytometry plots for identifying LP-MNPs (CD45+ MHCII+CD11c+) containing Ova-647 post intraluminal administration. (FIG. 23D) Absolute number of CD45.1 CBir T cells in the colon draining MLN three days following transfer. *P 0.05, n=4 for panel D.

(FIG. 23A) Primers specific for the CBir1 flagellin epitope produced by the Lachnospiracea bacteria A4 and COE1 and (FIG. 23B) primers specific for *B. vulgatus* were used to quantitate the number of organisms by performing quantitative real time PCR on DNA isolated from colonic contents. n=3 for each time point.

(FIG. 27A) Two-photon imaging for trans-epithelial dendrites in the intestine imaging of SI or colon of DOL18 CD11cYFP mice 20 minutes after administration of fluorescent dextran (red) to delineate the lumen and DAPI (blue) to stain epithelial nuclei. Dotted line indicates luminal surface. Vacuolated fetal enterocytes in the SI take up fluorescent dextran top panel. (FIG. 27B) Number of trans-epithelial dendrites (TEDs) per small intestinal villus or colonic crypt in the jejunum (J), proximal ileum (PI), distal ileum (DI), or colon (C) measured by two-photon imaging in a DOL18 and DOL42 mice. DOL18 mice were evaluated in the presence and absence of removal of the mucous barrier by washing with PBS. No TEDs were seen in the SI or colon of DOL18 mice, however consistent with prior reports, TEDs were observed in the distal ileum of DOL42 mice following removal of mucus by washing with PBS. Scale bar=50 µm.

(FIG. 28A) Absolute number of CD11c+MHCII+ cells in the colon LP or epithelial fraction (EA). (FIG. 28B) Percentage of colonic LP-MNPs capturing intravenously administered fluorescent Ova, and (FIG. 28C) fold increase in CBir1 T cells following co-culture of colonic LP-MNPs with exogenous flagellin in LP-MNPs isolated from DOL18 GC deficient mice or littermate controls. (FIG. 28D) Absolute number of CD11c+MHCII+ cells in the colon LP (left) or epithelial fraction (EA) (right) on DOL 8, 18, or 28 with or without EGFRi treatment. (FIG. 28E) Percent of CD11c+MHCII+ cells containing fluorescently labeled OVA-647 following intravenous administration on DOL 18 or 28, following GAP manipulation. (FIG. 28F) Fold increase in CBir1 T cells following in vitro culture with LP-MNP cells and 10 μg flagellin. n=4 mice per group panels A and D, n=3 mice per group panels FIG. 28B, FIG. 28C, FIG. 28E and FIG. 28F. ns=not significant, *P<0.05.

(FIG. 29A-FIG. 29B) Infraluminal fluorescent dextran (red) was could be seen within epithelial cells of goblet cell morphology (FIG. 29A) and colocalized with goblet cell marker CK18 (FIG. 29B) in DOL18 mice. Red arrow denotes CK18+ goblet cell with dextran, or a GAP, white arrow denotes a CK18+ cell not containing dextran. (FIG. 29C) Number of goblet cells per colonic crypt is unaffected by GAP manipulations. Colon tissue was isolated on day of life (DOL) 18, or 28, following GAP manipulations and sections were stained for CK-18. n=15 crypts from 3 mice per group in panel C. Scale bar=10 μm.

(FIG. 30A) Expression of TLRs 1-9 (labeled by the number), Myd88 (M), and EGFR (E) on FACS-sorted GCs from the SI (blue) or colon (red) of DOL18 mice. (FIG. 30B) Ratio of GAPs per GCs in the colon of DOL18 specific pathogen free (SPF) housed mice, germ-free (GF) housed mice, SPF housed Myd88−/− mice or SPF housed mice lacking Myd88 in GCs, with or without luminal heat-killed cecal contents from a DOL56 SPF housed mice. (FIG. 30C) Ratio of GAPs per GC in the colon of DOL18 mice following luminal LPS with or without inhibition of EGFR (EGFRi) or p42/p44 MAPK (MAPKi) activation. (FIG. 30D) Quantification of 16s rRNA in the cecal contents from DOL7-60 (FIG. 30E) Number of 16s rRNA sequences grouped by bacteria class across the first 28 days of life. Ratio of GAPs per GC in the (FIG. 30F) SI and (FIG. 30G) colon of Myd88$^{f/f}$Math1$^{PGRCre}$ mice lacking Myd88 in GCs, or cre negative littermates on DOLE, 18, or 28. nd=not detected, *=p<0.05, ns=not significant, n=4 mice per group. Experiments in FIG. 30A were repeated three independent times, FIG. 30B, FIG. 30C, FIG. 30F, and FIG. 30G were repeated two independent times.

(FIG. 31A) GAPs per crypt or villius cross section in the SI (blue) or colon (red) of SPF housed mice in the presence of tropicamide (t), or carbamycholine (CCh) treatment on DOL8, 18, or 28. (FIG. 31B) Immunofluorescent staining of phosphorylated EGFR (red; pEGFR) and cytokeratin 18 (green; CK18) in colon sections from DOL8, DOL18, and DOL28 mice; DAPI nuclear stain (blue). (FIG. 31C) amount of phosphorylated EGFR in the colon epithelium colon of DOL8,18, or 28 mice measured by ELISA. (FIG. 31D) GAPs per crypt (colon) or villus (SI) cross section in DOL8, 18, or 28 SPF housed mice in the presence or absence of EGFR inhibition (EGFRi). (FIG. 31E) Ratio of GAPs per GC and (FIG. 31F) percentage of LP-MNPs cells staining with luminal ova-647 in the SI and colon of DOL7, 14, 21, or 28 mice lacking EGFR in GCs or Cre negative littermate controls. (FIG. 31G-FIG. 31J) Mice were treated with vehicle or inhibition of EGFR activation (EGFRi) on DOL14 and 16 or 24 and 26 and LP-MNPs isolated or TCR transgenic T cells adoptively transferred on DOL18 or 28 respectively. (FIG. 31G) Fold increase in CBir1 transgenic T cells after ex vivo culture with LP-MNPs from colon isolated on DOL18 or DOL28. (FIG. 31H) Percent of CD45.1+ CBir1 or DP1 cells of total CD4+ T cells in the MLNs three days following transfer into recipient mice on DOL18 or DOL 28. (FIG. 31I) Percent of naïve (CD62L+) CBir1 or DP1 cells in the MLNs three days following transfer into recipient mice on DOL18 or DOL28. (FIG. 31J) Percent of Foxp3+ CBir1 or DP1 cells in the colon LP seven days following transfer into recipient mice on DOL18 or DOL 28. *=p<0.05, ns=not significant, n=4 mice per group. Experiments in A-D, and H were repeated three independent times, FIG. 31E-FIG. 31G, and FIG. 31I-FIG. 31J were repeated two independent times.

(FIG. 32A) Images of colon sections from DOL14 wildtype or GFR$^{f/f}$Math1$^{PGRCre}$ mice following luminal 10 kD fluorescent dextran (red) and luminal vehicle or EGF. (FIG. 32A) Images demonstrate that uptake of dextran by colonic epithelial cells on DOL14 is inhibited by luminal EGF in wildtype mice, but not in mice lacking EGFR in GCs. Blue=DAPI nuclear stain, scale bar=50 μm. n=4 mice per group panel FIG. 32B. *P <0.05.

(FIG. 33A) Concentration of EGF in the luminal contents of the stomach, SI, or colon in on DOL7, 14, or 21. (FIG. 33B) Concentration of EGF in the luminal contents, (FIG. 33C) amount of phosphorylated EGFR in the epithelium or (FIG. 33D) amount of phosphorylated p42/p44 MAPK in the epithelium of SI segments or colon of DOL14 mice measured by ELISA; SI segments, 1=0-6 cm, 2=6-12 cm, 3=12-18 cm, 4=18-24 cm measured from the pylorus. (FIG. 33E) Ratio of GAPs per GC following incubation with stomach contents (SC) from DOL10 mice, or recombinant EGF (EGF) in the presence or absence of EGFR inhibition (EGFRi) or p42/p44MAPK inhibition (MAPKi). (FIG. 33F) Fold increase in Ova specific OTI T cells after culture with colonic LP-MNPs isolated from DOL18 mice lacking EGFR in GCs or Cre negative littermate controls given luminal Ova or PBS and treated with intracolonic EGF, i.p. tropicamide (Trop), or untreated (Control). (FIG. 33G) Percentage of CBir1 T cells of total CD4+ T cells in the MLNs three days following cell transfer into DOL18 in mice that received intracolonic EGF (1 μg) or PBS daily from DOL10-21. *=p <0.05, ns=not significant, n=4 mice per group. Experiments in FIG. 33A-FIG. 33D, FIG. 33F, and FIG. 33G were repeated two independent times. FIG. 33E was repeated three independent times.

(FIG. 34A) percentage of CD45.1+ CBir1 T cells of total colon LP CD4+ T cells or (FIG. 34B) percentage of Foxp3+ or (FIG. 34C) IL-17+, TNFα+, or IFNγ+ CBir1 T cells among all CBir1 T cells in the colon LP following transfer on DOL16 and analysis on DOL30 in mice treated with intracolonic (ic) vehicle (PBS), or EGF on DOL10-21. (FIG. 34D) percentage of CD45.1+ CBir1 T cells of total colon LP CD4+ T cells or (FIG. 34E) percentage of Foxp3+ or (FIG. 34F) IL-17+, TNFα+, or IFNγ+ CBir1 T cells among all CBir1 T cells in the colon LP following transfer on DOL16 and analysis on DOL30 in mice treated with inhibition of EGFR activation (EGFRi) on DOL14 and 16, or on DOL24 and 26. *=p<0.05, ns=not significant, n=4 mice per group.

(FIG. 36A-FIG. 36C) Cytokine levels in the supernatant after three days of culture of MLNs from DOL35 mice that were untreated or treated with EGFRi on DOL14 and 16, or DOL24 and 26. (FIG. 36D) Cellular populations isolated from the colonic MLN of DOL35 mice treated as in A were evaluated for Foxp3+ expression by CD4+ T cells by flow cytometry. (FIG. 36E) H/E sections of colon from DOL35 mice treated as in A or receiving intracolonic PBS or EGF from DOL10-21 show no overt pathology. Scale bar=100 μm. n=3 mice per group performed in duplicate panels FIG. 36A-FIG. 36D. *P<0.05.

(FIG. 37A-FIG. 37F) Mice were given intracolonic PBS or EGF on DOL10-21 or G-L) inhibition of EGFR activation (EGFRi) on DOL 14 and 16 or 24 and 26, adoptively transferred CBir1 T cells on DOL 16, given dextran sodium sulfate (DSS) in drinking water from DOL30-38. FIG. 37A) and FIG. 37G) Weight loss, FIG. 37B) and FIG. 37H) histology score FIG. 37C) and FIG. 37I) colon length, FIG. 37D) and FIG. 37J) percentage of CBir1 T cells in the colon LP and percentage of FIG. 37E) and FIG. 37K) Foxp3+ and FIG. 37F) and FIG. 37L) percentage of IL-17+, TNFα+, or IFNγ+CBir1 T cells following 8 days of DSS treatment. *=p<0.05, ns=not significant, n=4 mice per group.

(FIG. 38A) H/E stained sections of colons after 8 days on 3% DSS in mice receiving intracolonic PBS or EGF from DOL10-21, or mice receiving EGFRi on DOL14 and 16, or DOL24 and 26. Black arrows denote ulceration, white arrow denotes infiltrates, and red line indicates edema. (FIG. 38B and FIG. 38C) Mice treated with intracolonic PBS or EGF on DOL10-21 adoptively transferred with CBir1 T cells on DOL16 and given 3% DSS for 8 days beginning on DOL30 FIG. 38B) Representative flow plots of colonic LP CD45.1+ CD3+CD4+ CBir1 T cells and FIG. 38C) expression of Foxp3 or intracellular IL17, IFNγ, or TNFα by colonic LP CBir1 T cells following DSS treatment. Scale bar=100 μm.

(FIG. 39A) Enumeration of GCs and GAPs per colonic crypt in DOL18 GC deficient mice or mice with mAChR4 deleted from GCs and their littermate controls. (FIG. 39A-FIG. 39F) GCs were deleted beginning on DOL12 or FIG. 39G-FIG. 39K) mAChR4 was deleted from GCs between DOL10-21, CBir1 T cells adoptively transferred on DOL16, and mice placed on DSS from DOL30-38. FIG. 39B and FIG. 39G) Weight loss FIG. 39C) and FIG. 39H) histology score FIG. 39D) and FIG. 39I) colon length, FIG. 39E) and FIG. 39J) percentage of CBir1 T cells expressing Foxp3, and FIG. 39F) and FIG. 39K) percentage of CBir1 T cells expressing IL17, TNFα, or IFNγ in the colon LP following 8 days of DSS treatment. *=p<0.05, ns=not significant, n=4 mice per group A-F, n=3 mice per group FIG. 39G-FIG. 39K.

DETAILED DESCRIPTION OF THE INVENTION

Figures 1A, 1B, 1C, 1D, 1E, 1F, 1G, 1H, 1I, 1J, 1K, 1L, 1M:
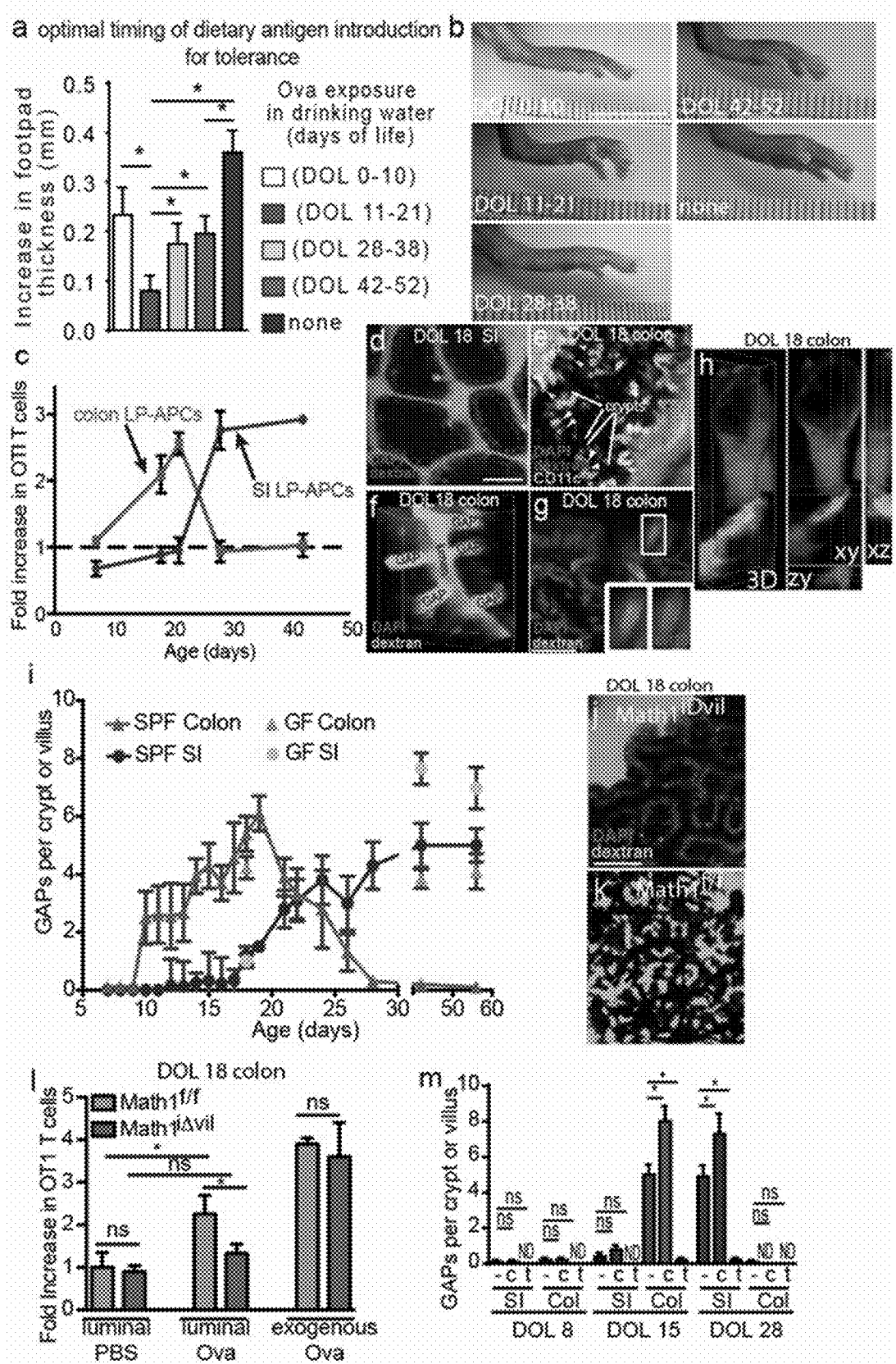
FIG. 1A-FIG. 1M is a series of graphs and images showing dietary antigen is delivered to the colonic immune system via goblet cell associated antigen passages (GAPs) and induces enhanced tolerance during a specific time in early life.

The present disclosure is based, at least in part, on the discovery that luminal EGF in the breast milk controls a regional and temporal of pattern of antigen exposure by the offspring's immune system and that disrupting this tight control results in persistent allergic responses. As shown herein, altering maternal control of antigen delivery results in persistent skewing of the offspring's immune response toward allergy. As such, this forms the biological basis as to why formula feeding is associated with allergic outcomes and indicates that supplementing formulas (or donor breast milk with low levels of EGFR ligands) with EGFR ligands in a pattern and concentration mimicking the normal pattern in breast milk will reduce allergic outcomes in children (see e.g., Example 1).

EGF and other EGFR ligands are naturally occurring substances in human breast milk. Experimental results disclosed herein (see e.g., Example 1) show that EGF and other EGFR ligands can prevent development of allergies (e.g., food allergies) in infants through multiple signaling pathways. It was shown that manipulation of maternal milk EGFR ligands mitigates the allergenic response in infant mice. The EGFR ligands act by modulating the formation of goblet cell-associated antigen passages, which permits antigens to travel from the lumen of the small intestines and encounter innate immune cells. This allows immune cells to access antigens presented by allergenic foods in the intestine. Exposure of the immune cells to these antigens can lead the body to recognize the suspected allergenic components from food items as non-threatening and prevents the allergic response.

The present disclosure relates generally to controlling microbial exposure. More particularly, the present disclosure is directed to methods for reducing allergic disorders in children by providing formulations having epidermal growth factor receptor (EGFR) ligands. The present disclosure is also directed to a dosage regimen for providing EGFR ligands in desired temporal patterns and specific concentrations. The present disclosure is further directed to methods for reducing late onset sepsis by administering epidermal growth factor. The present disclosure is further directed to methods for treating necrotizing enterocolitis by administering epidermal growth factor.

While previous studies have documented that gut bacteria can affect the outcome of T cell responses, few have examined how T cells encounter and respond to gut commensal bacterial antigens. Furthermore, results from the few studies examining this topic indicate that T cell responses to gut bacteria are dominated by a relatively small number of taxa that are closely adherent to the epithelium, such as segmented filamentous bacteria (SFB) or *Helicobacter*, while in contrast antigens from other bacteria, such as *Bacteriodes vulgatus* and the Lachnospiraceae bacterium A4, do not elicit responses from antigen specific T cells in the absence of inflammation. A limitation of the few previous studies, overcome in the present disclosure, is that the previous examined adult mice or gnotobiotic mice, which may not reflect the physiologic interactions of the developing immune system with the microbiota in early life. To overcome this limitation, lamina propria (LP) CD11c+ MHCII+ populations were isolated, referred to as mononuclear phagocytes (MNPs), from the SI and colon of conventionally housed mice during early life and evaluated their ability to stimulate CBir1 CD4+ TCR transgenic T cells specific for a flagellin epitope produced by the Lachnospiraceae bacterium, A4, and COE1 (see e.g., Example 3).

Allergic Disorder

The present disclosure provides for methods and compositions for treating or preventing allergic disorders by administering a composition comprising an EGFR ligand (e.g., epidermal growth factor). For example, the present disclosure provides for methods for reducing allergic disorders in children by administering a composition comprising an EGFR ligand.

In one aspect, the present disclosure is directed to methods for reducing allergic disorders in children by providing formulations having epidermal growth factor receptor (EGFR) ligands.

An allergic disorder or condition can be an allergy or allergic disease. An allergenic disorder can be caused by hypersensitivity of the immune system to something in the environment that usually causes little or no problem in most people. These diseases can include hay fever, food allergies, atopic dermatitis, allergic asthma, and anaphylaxis. Treatment of the allergenic disease can include alleviation of allergy symptoms including red eyes, a rash, an itchy rash, sneezing, a runny nose, shortness of breath, or swelling.

Common allergens can include pollen, certain food, metals, insect stings, medications. Allergenic disease can be due to both genetic and environmental factors. The underlying mechanism involves immunoglobulin E antibodies (IgE), part of the body's immune system, binding to an allergen and then to a receptor on mast cells or basophils where it triggers the release of inflammatory chemicals such as histamine.

Allergic disorders, manifested by T helper (Th2) type immune responses to environmental antigens, are rapidly increasing in children in Western societies. Decades of observational studies and interventional trials indicate that breast feeding with complementary introduction of food allergens around 4-6 months of age, combined with limited oral antibiotic exposure in the first year of life, reduce allergic outcomes in at-risk children. However, the biologic basis for these recommendations and the processes restricting these benefits to this specific time in early life are largely unknown.

As described herein, a pre-weaning interval was identified during which luminal antigens bypass the small intestine (SI) immune system and are assimilated by the colonic immune system. This interval coincided with a bloom of tolerance-inducing gut bacterial taxa, and was followed by the expansion of a long-lived population of RORγt+ inducible regulatory T-cells (iTregs). These iTregs can be directed towards dietary and microbial antigens, promote immune tolerance, and control Th2 responses.

Surprisingly, it was discovered that the timing and orchestration of these events are under maternal control via chronological changes in breast milk epidermal growth factor (EGF), which act on the offspring's gut to control the immune system's exposure to luminal substances.

Moreover, stools from breastfed, but not formula fed, children displayed a similar chronological pattern of EGF levels indicating this window initiates around 20 weeks of life in breastfed children. Manipulations altering maternal control and the timing of colonic antigen uptake, or manipulations of the gut microbiota during this specific interval produce durable (life-long) deficits in RORγt+ iTregs, impaired tolerance induction, and persistent Th2 responses to antigens encountered throughout life. These findings provide a biological basis for current childhood feeding recommendations and demonstrate a critical role for maternal control of exposure to microbial substances and dietary antigens in the balanced development of the immune system.

Manipulations altering the timing of colonic antigen uptake/exposure such as exposure to lower levels of luminal EGF as would be seen in formula feeding or exposure to inappropriately high levels of luminal EGF which would inhibit antigen/microbial exposure, as might be seen with the use of donor breast milk, resulted in persistent Th2 responses characteristic of allergy. These observations support the hypothesis that the dramatic increase in allergies in children results from feeding regimens that alter the normal timing of antigen exposure and suggest that formula feedings with the chronologically appropriate levels of EGFR ligands could mitigate the risk of allergy in children who cannot be breast fed by their mother.

Necrotizing Enterocolitis (NEC)

The present disclosure provides for methods and compositions for treating, preventing, or reducing necrotizing enterocolitis by administering an EGFR ligand (e.g., epidermal growth factor).

Necrotizing enterocolitis (NEC) is a disease that affects mostly the intestine of premature infants. Patients develop NEC as a result of bacteria invading the wall of the intestine, which causes local infection and inflammation that can ultimately destroy the intestinal wall of the intestine.

Accordingly, there exists a need in the art for methods to control dietary antigen and microbial exposures early in life.

Sepsis

In one aspect, the present disclosure is directed to methods and compositions for treating, preventing, or reducing late onset sepsis by administering an epidermal growth factor receptor (EGFR) ligand.

Further, oral EGF, mimicking the concentration in breast milk of mothers can reduce incidents of late onset sepsis. Late onset sepsis is a condition that affects low birth weight babies in the neonatal intensive care unit that are generally not breast fed. When these low birth weight babies are given breast milk, it is typically from donors who are usually near the end of lactation and contains low levels of EGF.

Neonatal sepsis is a bloodstream infection and a leading cause of death in newly born babies accounting for 26% of all neonatal deaths. Late onset sepsis results from causative organisms acquired after delivery.

Neonatal sepsis, a bloodstream infection and a leading cause of death in newly born babies accounting for 26% of all neonatal deaths, can be divided into early-onset sepsis (EOS) and late-onset sepsis (LOS). EOS can be caused by transplacental or ascending infections from the maternal genital tract, while the organisms causative of LOS can be acquired after delivery. Patients most at risk of LOS can be those born with very low birth weight, and often placed in intensive care units without access to breast milk. In a substantial portion of LOS, the pathogen can be found as a resident of the neonatal gut microbial community prior to disease. Currently it is hypothesized that an immature gut barrier is to blame for the translocation of resident gut bacteria resulting in LOS, yet the mechanisms allowing or inhibiting translocation of the gut microbiota in early life have remained enigmatic.

Inflammatory Disease, Disorder, or Condition

In one aspect, the present disclosure is directed to methods and compositions for treating, preventing, or reducing inflammatory diseases, disorders, or conditions (see e.g., Example 3) by administering epidermal growth factor receptor (EGFR) ligand. Damage from inappropriate inflammatory responses is not limited to the host cells, but also induces dysbiosis of the gut microbiota, which has been associated with multiple disorders and in turn promotes host inflammatory responses.

For example, the methods and compositions as described herein can be used to treat a chronic inflammatory condition of the GI tract, such as inflammatory bowel disease (IBD), colitis, or Crohn's disease.

In some embodiments, the inflammatory disease, disorder, or condition can be an inflammatory disease, disorder, or condition affecting the small intestine or colon. As another example, the inflammatory disease, disorder, or condition can include inflammation of both (or either of) the colon (e.g., ulcerative colitis), the ileum also called ileitis, or Crohn's disease. As such, the methods as described herein are of impact to methods of treatment, diagnosis, and screening for drugs for colitis and ileitis.

In some embodiments, inflammatory disease, disorder, or condition can be colitis, ileitis, inflammatory bowel disease, Crohn's disease, ulcerative colitis, ischemic colitis, colitis from allergic reactions, or microscopic colitis. For example, colitis and ileitis can refer to inflammation of the inner lining of the colon or the ileum, respectively.

Causes of colitis or ileitis can include infection, inflammatory bowel disease (e.g., Crohn's disease, ulcerative colitis), ischemic colitis, allergic reactions, or microscopic colitis.

Subjects

The subject can be an animal subject, including a mammal, such as horses, cows, dogs, cats, sheep, pigs, mice, rats, monkeys, hamsters, guinea pigs, and chickens, and humans. For example, the subject can be a human subject.

For example, the human subject can include adults, children, or infants. The subject may be a newborn, neonatal, low birth weight, or premature infant. The subject may be any child from birth to about 1 year, birth to about 18 months old, birth to about two years old, or birth to about weaning age (the age at which the subject is weaned). Other suitable subjects include animals such as companion pets and laboratory animals such as mice.

For the studies performed in mice (see Examples 1-3), it is notable that individuals with Crohn's disease make systemic immune responses to the CBir1 antigen, and it was observed that pTregs specific for CBir1 antigen were largely induced during the post-neonatal phase of life in mice. This indicates that the events identified in pre-weaning mice have relevance and can be translated to humans and combined with observations that antibiotic use in the first year of life is associated with an increased incidence of asthma, allergy, and inflammatory bowel disease, strongly suggests that altering microbial antigen encounters during specific intervals in pre-weaning children increases the risk of disease.

Figures 30A, 30B, 30C, 30D, 30E, 30F, 30G:
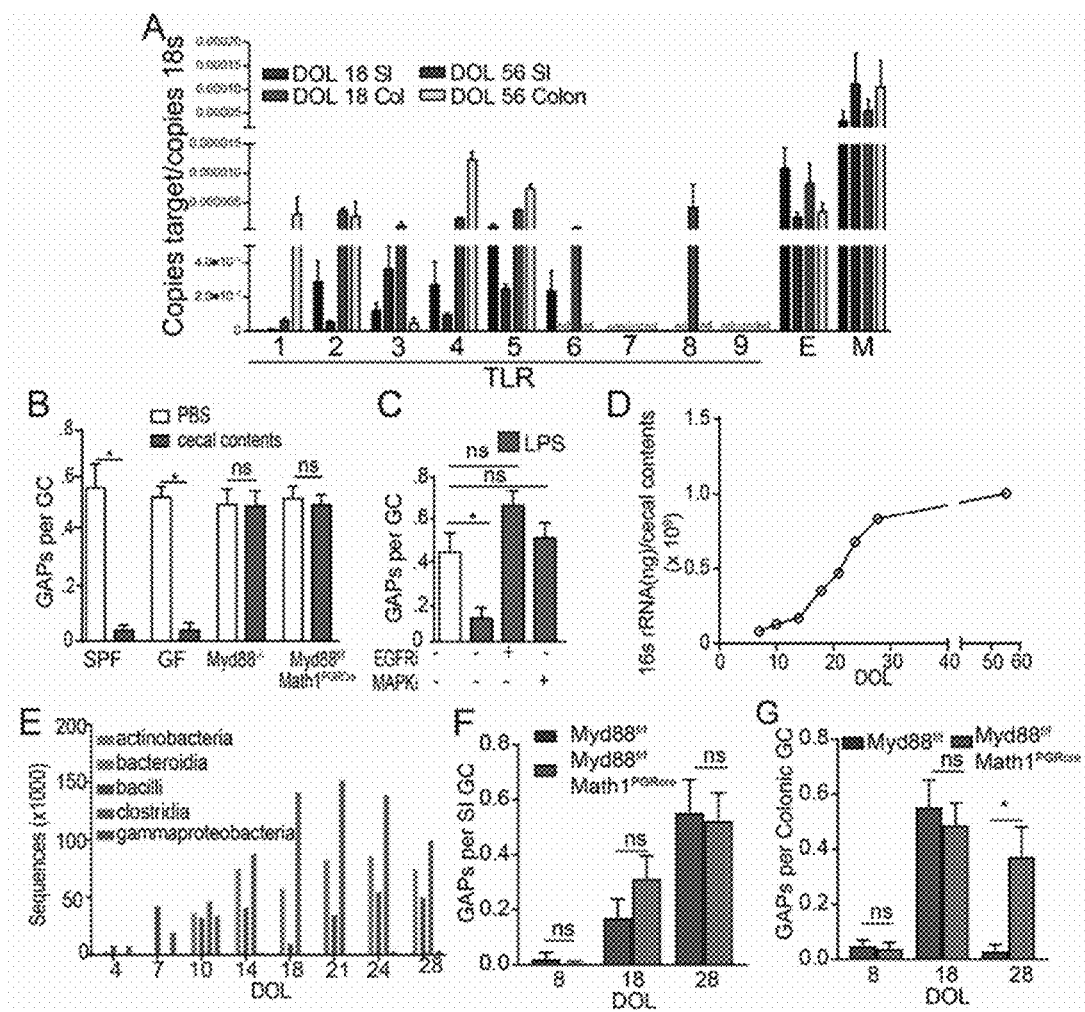
FIG. 30A-FIG. 30G is a series of graphs showing the microbiota inhibits colonic GAPs and antigen delivery post-weaning.

Further, additional evidence was discovered that the studies performed in mice can be readily translated to humans. GCs in the colon of adult mice are largely unable to form GAPs due to Myd88 dependent GC intrinsic sensing of the abundant colonic microbes and microbial products. GC microbial sensing activates the epidermal growth factor receptor (EGFR) and p42/p44 mitogen activated protein kinase (MAPK), inhibiting GC responses to acetylcholine (ACh), the stimulus inducing spontaneous GAP formation. Like intestinal GCs from adults, GCs from pre-weaning DOL18 mice expressed TLRs, Myd88, and EGFR (see e.g., FIG. 30A), suggesting that they would respond similarly to microbial products.

EGFR Ligand

As described herein, compositions comprising an EGFR ligand can be used to can modulate colonic antigen uptake or exposure by modulating the formation of goblet cell-associated antigen passages (GAP), which permits antigens to travel from the lumen of the small intestines and encounter innate immune cells. EGFR is also known as HER1 or Erb-B1.

EGFR ligand can allow for luminal antigens to bypass the small intestine (SI) immune system and be assimilated by the colonic immune system, allowing for a bloom of tolerance-inducing gut bacterial taxa, and is followed by the expansion of a long-lived population of RORγt+ inducible regulatory T-cells (iTregs). These iTregs can be directed towards dietary and microbial antigens, promote immune tolerance, and control Th2 responses.

EGFR ligands are well known; see e.g. Harris R. EGF receptor ligands. Experimental Cell Research 2003; 284(1): 2-13. Except as otherwise noted herein, therefore, the compositions of the present disclosure can be in accordance with such compositions. For example, an EGFR ligand can be EGF, transforming growth factor-α (TGFα), heparin-binding EGF-like growth factor (HB-EGF), amphiregulin (AR), betacellulin (BTC), epiregulin (EPR), hyaluronic acid, epigen, or other EGFR activators.

Suitable epidermal growth factor receptor (EGFR) ligands include epidermal growth factor. Epidermal growth factor receptor (EGFR) ligands can be provided as oral forms, liquid forms, powder forms, and other forms known to those skilled in the art. Suitable forms include supplements to donated breast milk or infant formulas such as liquid formulas and powdered formulas that are mixed with a liquid to prior to use. Other suitable forms include infant formulas such as liquid formulas and powdered formulas that are mixed with a liquid to prior to use.

The EGFR ligand can be administered in a dose similar to that found in breast milk (see e.g., Oguchi S, Shinohara K, Yamashiro Y, Walker W, Sanderson Growth factors in breast milk and their effect on gastrointestinal development. Zhonghua Min Guo Xiao Er Ke Yi Xue Hui Za Zhi. 1997; 38(5):332-3371). Growth factors in breast milk have been shown to have an effect on gastrointestinal development (Zhonghua et al.1997; 38(5):332-337). In some embodiments, the EGFR ligand concentration to be administered (e.g., in an infant supplement or formulation) can be between about 0.02 µg/mL and about 0.2 µg/mL. For example, the EGFR ligand concentration can be administered at a concentration of about 0.01 µg/mL; about 0.02 µg/mL; about 0.03 µg/mL; about 0.04 µg/mL; about 0.05 µg/mL; about 0.06 µg/mL; about 0.07 µg/mL; about 0.08 µg/mL; about 0.09 µg/mL; about 0.10 µg/mL; about 0.11 µg/mL; about 0.12 µg/mL; about 0.13 µg/mL; about 0.14 µg/mL; about 0.15 µg/mL; about 0.16 µg/mL; about 0.17 µg/mL; about 0.18 µg/mL; about 0.19 µg/mL; or about 0.2

µg/mL. Recitation of each of these discrete values is understood to include ranges between each value. Recitation of each range is understood to include discrete values within the range.

The amount of EGFR ligand added to the infant formula can be based on the age of the subject (e.g., infant or child). The EGFR ligand concentration can vary depending on the age of the subject or the day after delivery or birth. For example, the dose of EGFR ligand delivered to the subject through an oral formulation (e.g., infant formula) can be between about 0.02 µg/mL and about 0.2 µg/mL for an infant between about 0 days old (day of birth) and about 1 year of age, about 18 months of age, about two years of age, or age the child is weaned (i.e., weaning age), or between 0 days old and about 140 days old. For example, the EGFR ligand concentration can be administered at a concentration of about 0.02 µg/mL; about 0.03 µg/mL; about 0.04 µg/mL; about 0.05 µg/mL; about 0.06 µg/mL; about 0.07 µg/mL; about 0.08 µg/mL; about 0.09 µg/mL; about 0.10 µg/mL; about 0.11 µg/mL; about 0.12 µg/mL; about 0.13 µg/mL; about 0.14 µg/mL; about 0.15 µg/mL; about 0.16 µg/mL; about 0.17 µg/mL; about 0.18 µg/mL; about 0.19 µg/mL; or about 0.2 µg/mL. As another example, the subject can be about 0 days old; about 1 day old; about 2 days old; about 3 days old; about 4 days old; about 5 days old; about 6 days old; about 7 days old; about 8 days old; about 9 days old; about 10 days old; about 11 days old; about 12 days old; about 13 days old; about 14 days old; about 15 days old; about 16 days old; about 17 days old; about 18 days old; about 19 days old; about 20 days old; about 21 days old; about 22 days old; about 23 days old; about 24 days old; about 25 days old; about 26 days old; about 27 days old; about 28 days old; about 29 days old; about 30 days old; about 31 days old; about 32 days old; about 33 days old; about 34 days old; about 35 days old; about 36 days old; about 37 days old; about 38 days old; about 39 days old; about 40 days old; about 41 days old; about 42 days old; about 43 days old; about 44 days old; about 45 days old; about 46 days old; about 47 days old; about 48 days old; about 49 days old; about 50 days old; about 51 days old; about 52 days old; about 53 days old; about 54 days old; about 55 days old; about 56 days old; about 57 days old; about 58 days old; about 59 days old; about 60 days old; about 61 days old; about 62 days old; about 63 days old; about 64 days old; about 65 days old; about 66 days old; about 67 days old; about 68 days old; about 69 days old; about 70 days old; about 71 days old; about 72 days old; about 73 days old; about 74 days old; about 75 days old; about 76 days old; about 77 days old; about 78 days old; about 79 days old; about 80 days old; about 81 days old; about 82 days old; about 83 days old; about 84 days old; about 85 days old; about 86 days old; about 87 days old; about 88 days old; about 89 days old; about 90 days old; about 91 days old; about 92 days old; about 93 days old; about 94 days old; about 95 days old; about 96 days old; about 97 days old; about 98 days old; about 99 days old; about 100 days old; about 101 days old; about 102 days old; about 103 days old; about 104 days old; about 105 days old; about 106 days old; about 107 days old; about 108 days old; about 109 days old; about 110 days old; about 111 days old; about 112 days old; about 113 days old; about 114 days old; about 115 days old; about 116 days old; about 117 days old; about 118 days old; about 119 days old; about 120 days old; about 121 days old; about 122 days old; about 123 days old; about 124 days old; about 125 days old; about 126 days old; about 127 days old; about 128 days old; about 129 days old; about 130 days old; about 131 days old; about 132 days old; about 133 days old; about 134 days old; about 135 days old; about 136 days old; about 137 days old; about 138 days old; about 139 days old; about 140 days old; about 141 days old; about 142 days old; about 143 days old; about 144 days old; about 145 days old; about 146 days old; about 147 days old; about 148 days old; about 149 days old; about 150 days old; about 151 days old; about 152 days old; about 153 days old; about 154 days old; about 155 days old; about 156 days old; about 157 days old; about 158 days old; about 159 days old; about 160 days old; about 161 days old; about 162 days old; about 163 days old; about 164 days old; about 165 days old; about 166 days old; about 167 days old; about 168 days old; about 169 days old; about 170 days old; about 171 days old; about 172 days old; about 173 days old; about 174 days old; about 175 days old; about 176 days old; about 177 days old; about 178 days old; about 179 days old; about 180 days old; about 181 days old; about 182 days old; about 183 days old; about 184 days old; about 185 days old; about 186 days old; about 187 days old; about 188 days old; about 189 days old; about 190 days old; about 191 days old; about 192 days old; about 193 days old; about 194 days old; about 195 days old; about 196 days old; about 197 days old; about 198 days old; about 199 days old; about 200 days old; about 201 days old; about 202 days old; about 203 days old; about 204 days old; about 205 days old; about 206 days old; about 207 days old; about 208 days old; about 209 days old; about 210 days old; about 211 days old; about 212 days old; about 213 days old; about 214 days old; about 215 days old; about 216 days old; about 217 days old; about 218 days old; about 219 days old; about 220 days old; about 221 days old; about 222 days old; about 223 days old; about 224 days old; about 225 days old; about 226 days old; about 227 days old; about 228 days old; about 229 days old; about 230 days old; about 231 days old; about 232 days old; about 233 days old; about 234 days old; about 235 days old; about 236 days old; about 237 days old; about 238 days old; about 239 days old; about 240 days old; about 241 days old; about 242 days old; about 243 days old; about 244 days old; about 245 days old; about 246 days old; about 247 days old; about 248 days old; about 249 days old; about 250 days old; about 251 days old; about 252 days old; about 253 days old; about 254 days old; about 255 days old; about 256 days old; about 257 days old; about 258 days old; about 259 days old; about 260 days old; about 261 days old; about 262 days old; about 263 days old; about 264 days old; about 265 days old; about 266 days old; about 267 days old; about 268 days old; about 269 days old; about 270 days old; about 271 days old; about 272 days old; about 273 days old; about 274 days old; about 275 days old; about 276 days old; about 277 days old; about 278 days old; about 279 days old; about 280 days old; about 281 days old; about 282 days old; about 283 days old; about 284 days old; about 285 days old; about 286 days old; about 287 days old; about 288 days old; about 289 days old; about 290 days old; about 291 days old; about 292 days old; about 293 days old; about 294 days old; about 295 days old; about 296 days old; about 297 days old; about 298 days old; about 299 days old; about 300 days old; about 301 days old; about 302 days old; about 303 days old; about 304 days old; about 305 days old; about 306 days old; about 307 days old; about 308 days old; about 309 days old; about 310 days old; about 311 days old; about 312 days old; about 313 days old; about 314 days old; about 315 days old; about 316 days old; about 317 days old; about 318 days old; about 319 days old; about 320 days old; about 321 days old; about 322 days old; about 323 days old; about 324 days old; about 325 days old; about 326 days old; about 327 days old; about 328 days old; about 329 days old; about 330 days old; about 331 days old; about 332 days old; about 333 days old;

about 334 days old; about 335 days old; about 336 days old; about 337 days old; about 338 days old; about 339 days old; about 340 days old; about 341 days old; about 342 days old; about 343 days old; about 344 days old; about 345 days old; about 346 days old; about 347 days old; about 348 days old; about 349 days old; about 350 days old; about 351 days old; about 352 days old; about 353 days old; about 354 days old; about 355 days old; about 356 days old; about 357 days old; about 358 days old; about 359 days old; about 360 days old; about 361 days old; about 362 days old; about 363 days old; about 364 days old; about 365 days old; 366 days old; about 367 days old; about 368 days old; about 369 days old; about 370 days old; about 371 days old; about 372 days old; about 373 days old; about 374 days old; about 375 days old; about 376 days old; about 377 days old; about 378 days old; about 379 days old; about 380 days old; about 381 days old; about 382 days old; about 383 days old; about 384 days old; about 385 days old; about 386 days old; about 387 days old; about 388 days old; about 389 days old; about 390 days old; about 391 days old; about 392 days old; about 393 days old; about 394 days old; about 395 days old; about 396 days old; about 397 days old; about 398 days old; about 399 days old; about 400 days old; about 401 days old; about 402 days old; about 403 days old; about 404 days old; about 405 days old; about 406 days old; about 407 days old; about 408 days old; about 409 days old; about 410 days old; about 411 days old; about 412 days old; about 413 days old; about 414 days old; about 415 days old; about 416 days old; about 417 days old; about 418 days old; about 419 days old; about 420 days old; about 421 days old; about 422 days old; about 423 days old; about 424 days old; about 425 days old; about 426 days old; about 427 days old; about 428 days old; about 429 days old; about 430 days old; about 431 days old; about 432 days old; about 433 days old; about 434 days old; about 435 days old; about 436 days old; about 437 days old; about 438 days old; about 439 days old; about 440 days old; about 441 days old; about 442 days old; about 443 days old; about 444 days old; about 445 days old; about 446 days old; about 447 days old; about 448 days old; about 449 days old; about 450 days old; about 451 days old; about 452 days old; about 453 days old; about 454 days old; about 455 days old; about 456 days old; about 457 days old; about 458 days old; about 459 days old; about 460 days old; about 461 days old; about 462 days old; about 463 days old; about 464 days old; about 465 days old; about 466 days old; about 467 days old; about 468 days old; about 469 days old; about 470 days old; about 471 days old; about 472 days old; about 473 days old; about 474 days old; about 475 days old; about 476 days old; about 477 days old; about 478 days old; about 479 days old; about 480 days old; about 481 days old; about 482 days old; about 483 days old; about 484 days old; about 485 days old; about 486 days old; about 487 days old; about 488 days old; about 489 days old; about 490 days old; about 491 days old; about 492 days old; about 493 days old; about 494 days old; about 495 days old; about 496 days old; about 497 days old; about 498 days old; about 499 days old; about 500 days old; about 501 days old; about 502 days old; about 503 days old; about 504 days old; about 505 days old; about 506 days old; about 507 days old; about 508 days old; about 509 days old; about 510 days old; about 511 days old; about 512 days old; about 513 days old; about 514 days old; about 515 days old; about 516 days old; about 517 days old; about 518 days old; about 519 days old; about 520 days old; about 521 days old; about 522 days old; about 523 days old; about 524 days old; about 525 days old; about 526 days old; about 527 days old; about 528 days old; about 529 days old; about 530 days old; about 531 days old; about 532 days old; about 533 days old; about 534 days old; about 535 days old; about 536 days old; about 537 days old; about 538 days old; about 539 days old; about 540 days old; about 541 days old; about 542 days old; about 543 days old; about 544 days old; about 545 days old; about 546 days old; about 547 days old; about 548 days old; about 549 days old; or about 550 days old. Recitation of each of these discrete values is understood to include ranges between each value. Recitation of each range is understood to include discrete values within the range.

In some embodiments, administration of and EGFR ligand to a subject between about 1 day old and about 10 days old can be between about 0.10 µg/mL and about 0.20 µg/mL. The concentration of EGFR ligand can administered to the subject in a low volume high concentration of EGFR ligand or higher volume lower concentration of EGFR ligand in, for example, a formula. For example, the EGFR ligand concentration can be administered at a concentration of about 0.10 µg/mL; about 0.11 µg/mL; about 0.12 µg/mL; about 0.13 µg/mL; about 0.14 µg/mL; about 0.15 µg/mL; about 0.16 µg/mL; about 0.17 µg/mL; about 0.18 µg/mL; about 0.19 µg/mL; or about 0.2 µg/mL. Recitation of each of these discrete values is understood to include ranges between each value. Recitation of each range is understood to include discrete values within the range.

In some embodiments, administration of and EGFR ligand to a subject between birth and about 18 months, about 1 year, or weaning, can be between about 0.01 µg/mL and about 100 µg/mL. The concentration of EGFR ligand can administered to the subject in a low volume high concentration of EGFR ligand or higher volume lower concentration of EGFR ligand in, for example, a formula. For example, the EGFR ligand concentration can be administered at a concentration of about 0.01 µg/mL; about 0.02 µg/mL; about 0.03 µg/mL; about 0.04 µg/mL; about 0.05 µg/mL; about 0.06 µg/mL; about 0.07 µg/mL; about 0.08 µg/mL; about 0.09 µg/mL; about 0.1 µg/mL; about 0.2 µg/mL; about 0.3 µg/mL; about 0.4 µg/mL, about 0.5 µg/mL, about 0.6 µg/mL, about 0.7 µg/mL, about 0.8 µg/mL; about 0.9 µg/mL; about 1 µg/mL; about 1.5 µg/mL; about 2 µg/mL; about 2.5 µg/mL; about 3 µg/mL; about 3.5 µg/mL; about 4 µg/mL; about 4.5 µg/mL; about 5 µg/mL; about 5.5 µg/mL; about 6 µg/mL; about 6.5 µg/mL; about 7 µg/mL; about 7.5 µg/mL; about 8 µg/mL; about 8.5 µg/mL; about 9 µg/mL; about 9.5 µg/mL; about 10 µg/mL; about 10.5 µg/mL; about 11 µg/mL; about 11.5 µg/mL; about 12 µg/mL; about 12.5 µg/mL; about 13 µg/mL; about 13.5 µg/mL; about 14 µg/mL; about 14.5 µg/mL; about 15 µg/mL; about 15.5 µg/mL; about 16 µg/mL; about 16.5 µg/mL; about 17 µg/mL; about 17.5 µg/mL; about 18 µg/mL; about 18.5 µg/mL; about 19 µg/mL; about 19.5 µg/mL; about 20 µg/mL; about 20.5 µg/mL; about 21 µg/mL; about 21.5 µg/mL; about 22 µg/mL; about 22.5 µg/mL; about 23 µg/mL; about 23.5 µg/mL; about 24 µg/mL; about 24.5 µg/mL; about 25 µg/mL; about 25.5 µg/mL; about 26 µg/mL; about 26.5 µg/mL; about 27 µg/mL; about 27.5 µg/mL; about 28 µg/mL; about 28.5 µg/mL; about 29 µg/mL; about 29.5 µg/mL; about 30 µg/mL; about 30.5 µg/mL; about 31 µg/mL; about 31.5 µg/mL; about 32 µg/mL; about 32.5 µg/mL; about 33 µg/mL; about 33.5 µg/mL; about 34 µg/mL; about 34.5 µg/mL; about 35 µg/mL; about 35.5 µg/mL; about 36 µg/mL; about 36.5 µg/mL; about 37 µg/mL; about 37.5 µg/mL; about 38 µg/mL; about 38.5 µg/mL; about 39 µg/mL; about 39.5 µg/mL; about 40 µg/mL; about 40.5 µg/mL; about 41 µg/mL; about 41.5 µg/mL; about 42 µg/mL; about 42.5 µg/mL; about 43 µg/mL; about 43.5 µg/mL; about 44 µg/mL; about 44.5 µg/mL; about 45 µg/mL; about 45.5 µg/mL; about 46 µg/mL; about 46.5 µg/mL; about 47 µg/mL; about 47.5 µg/mL;

about 48 µg/mL; about 48.5 µg/mL; about 49 µg/mL; about 49.5 µg/mL; about 50 µg/mL; about 50.5 µg/mL; about 51 µg/mL; about 51.5 µg/mL; about 52 µg/mL; about 52.5 µg/mL; about 53 µg/mL; about 53.5 µg/mL; about 54 µg/mL; about 54.5 µg/mL; about 55 µg/mL; about 55.5 µg/mL; about 56 µg/mL; about 56.5 µg/mL; about 57 µg/mL; about 57.5 µg/mL; about 58 µg/mL; about 58.5 µg/mL; about 59 µg/mL; about 59.5 µg/mL; about 60 µg/mL; about 60.5 µg/mL; about 61 µg/mL; about 61.5 µg/mL; about 62 µg/mL; about 62.5 µg/mL; about 63 µg/mL; about 63.5 µg/mL; about 64 µg/mL; about 64.5 µg/mL; about 65 µg/mL; about 65.5 µg/mL; about 66 µg/mL; about 66.5 µg/mL; about 67 µg/mL; about 67.5 µg/mL; about 68 µg/mL; about 68.5 µg/mL; about 69 µg/mL; about 69.5 µg/mL; about 70 µg/mL; about 70.5 µg/mL; about 71 µg/mL; about 71.5 µg/mL; about 72 µg/mL; about 72.5 µg/mL; about 73 µg/mL; about 73.5 µg/mL; about 74 µg/mL; about 74.5 µg/mL; about 75 µg/mL; about 75.5 µg/mL; about 76 µg/mL; about 76.5 µg/mL; about 77 µg/mL; about 77.5 µg/mL; about 78 µg/mL; about 78.5 µg/mL; about 79 µg/mL; about 79.5 µg/mL; about 80 µg/mL; about 80.5 µg/mL; about 81 µg/mL; about 81.5 µg/mL; about 82 µg/mL; about 82.5 µg/mL; about 83 µg/mL; about 83.5 µg/mL; about 84 µg/mL; about 84.5 µg/mL; about 85 µg/mL; about 85.5 µg/mL; about 86 µg/mL; about 86.5 µg/mL; about 87 µg/mL; about 87.5 µg/mL; about 88 µg/mL; about 88.5 µg/mL; about 89 µg/mL; about 89.5 µg/mL; about 90 µg/mL; about 90.5 µg/mL; about 91 µg/mL; about 91.5 µg/mL; about 92 µg/mL; about 92.5 µg/mL; about 93 µg/mL; about 93.5 µg/mL; about 94 µg/mL; about 94.5 µg/mL; about 95 µg/mL; about 95.5 µg/mL; about 96 µg/mL; about 96.5 µg/mL; about 97 µg/mL; about 97.5 µg/mL; about 98 µg/mL; about 98.5 µg/mL; about 99 µg/mL; about 99.5 µg/mL; or about 100 µg/mL. Recitation of each of these discrete values is understood to include ranges between each value. Recitation of each range is understood to include discrete values within the range.

In some embodiments, administration of an EGFR ligand to a subject between about 10 days old and about 30 days old can be between about 0.04 µg/mL and about 0.12 µg/mL. Recitation of each of these discrete values is understood to include ranges between each value. Recitation of each range is understood to include discrete values within the range.

In some embodiments, administration of and EGFR ligand to a subject between about 30 days old and about 365 days old can be between about 0.03 µg/mL and about 0.12 µg/mL. Recitation of each of these discrete values is understood to include ranges between each value. Recitation of each range is understood to include discrete values within the range.

Concentrations of EGFR ligands administered to a subject can be adjusted to mimic the natural temporal pattern of EGFR ligands in breast milk post-delivery in humans or other mammals. The concentration of EGFR ligand can be determined by calculating the daily amount of EGFR ligand to be given to the subject in one single dose or in several doses given throughout the day at each feeding.

In some embodiments, a typical serving size of formula for an infant is between about 2 oz (about 59 mL) and about 8 oz (about 237 mL). As such, for every ounce (about 30 mL) of formula, the EGFR ligand can be at a concentration between about 0.06 µg and about 6 µg (e.g., between about 0.06 µg/oz and about 6 µg/oz EGFR ligand). For example, the EGFR ligand can be at a concentration of about 0.06 µg/oz; about 0.07 µg/oz; about 0.08 µg/oz; about 0.09 µg/oz; about 0.1 µg/oz; about 0.11 µg/oz; about 0.12 µg/oz; about 0.13 µg/oz; about 0.14 µg/oz; about 0.15 µg/oz; about 0.16 µg/oz; about 0.17 µg/oz; about 0.18 µg/oz; about 0.19 µg/oz; about 0.2 µg/oz; about 0.21 µg/oz; about 0.22 µg/oz; about 0.23 µg/oz; about 0.24 µg/oz; about 0.25 µg/oz; about 0.26 µg/oz; about 0.27 µg/oz; about 0.28 µg/oz; about 0.29 µg/oz; about 0.3 µg/oz; about 0.31 µg/oz; about 0.32 µg/oz; about 0.33 µg/oz; about 0.34 µg/oz; about 0.35 µg/oz; about 0.36 µg/oz; about 0.37 µg/oz; about 0.38 µg/oz; about 0.39 µg/oz; about 0.4 µg/oz; about 0.41 µg/oz; about 0.42 µg/oz; about 0.43 µg/oz; about 0.44 µg/oz; about 0.45 µg/oz; about 0.46 µg/oz; about 0.47 µg/oz; about 0.48 µg/oz; about 0.49 µg/oz; about 0.5 µg/oz; about 0.51 µg/oz; about 0.52 µg/oz; about 0.53 µg/oz; about 0.54 µg/oz; about 0.55 µg/oz; about 0.56 µg/oz; about 0.57 µg/oz; about 0.58 µg/oz; about 0.59 µg/oz; or about 0.6 µg/oz. Recitation of each of these discrete values is understood to include ranges between each value. Recitation of each range is understood to include discrete values within the range.

A human infant can be fed between about 5 oz a day to about 32 oz a day, depending on the age of the human subject. As such, a single daily dose of an EGFR ligand can be between about 0.06 µg EGFR ligand and about 20 µg EGFR ligand. For example, the EGFR ligand can be administered at a single daily dose of about 0.06 µg; about 0.07 µg; about 0.08 µg; about 0.09 µg; about 0.1 µg; about 0.2 µg; about 0.3 µg; about 0.4 µg; about 0.5 µg; about 0.6 µg; about 0.7 µg; about 0.8 µg; about 0.9 µg; about 1 µg; about 1.5 µg; about 2 µg; about 2.5 µg; about 3 µg; about 3.5 µg; about 4 µg; about 4.5 µg; about 5 µg; about 5.5 µg; about 6 µg; about 6.5 µg; about 7 µg; about 7.5 µg; about 8 µg; about 8.5 µg; about 9 µg; about 9.5 µg; about 10 µg; about 10.5 µg; about 11 µg; about 11.5 µg; about 12 µg; about 12.5 µg; about 13 µg; about 13.5 µg; about 14 µg; about 14.5 µg; about 15 µg; about 15.5 µg; about 16 µg; about 16.5 µg; about 17 µg; about 17.5 µg; about 18 µg; about 18.5 µg; about 19 µg; about 19.5 µg; or about 20 µg. Recitation of each of these discrete values is understood to include ranges between each value. Recitation of each range is understood to include discrete values within the range.

Formulation

The agents and compositions described herein can be formulated by any conventional manner using one or more pharmaceutically acceptable carriers or excipients as described in, for example, Remington's Pharmaceutical Sciences (A. R. Gennaro, Ed.), 21st edition, ISBN: 0781746736 (2005), incorporated herein by reference in its entirety. Such formulations will contain a therapeutically effective amount of a biologically active agent described herein, which can be in purified form, together with a suitable amount of carrier so as to provide the form for proper administration to the subject.

The compositions and methods herein can be used as a supplement to infant formula, parenteral hyperalimentation, donated breast milk, donated breast milk with insufficient levels of EGFR ligand, a food formulation, a powdered formulation, liquid formulation, liquid dispensed in a dropper bottle, a capsule, powdered infant formula, liquid concentrate infant formula, ready-to-use infant formula, parenteral hyperalimentation, supplement, powder, and drops.

Methods of tailoring infant formulas to individual nutritional needs prior to use are well known; see e.g. US20070243290 and is incorporated herein by reference in its entirety. Except as otherwise noted herein, therefore, the process of the present disclosure can be carried out in accordance with such processes.

The term "formulation" refers to preparing a drug in a form suitable for administration to a subject, such as a human. Thus, a "formulation" can include pharmaceutically acceptable excipients, including diluents or carriers.

The term "pharmaceutically acceptable" as used herein can describe substances or components that do not cause unacceptable losses of pharmacological activity or unacceptable adverse side effects. Examples of pharmaceutically acceptable ingredients can be those having monographs in United States Pharmacopeia (USP 29) and National Formulary (NF 24), United States Pharmacopeial Convention, Inc, Rockville, Md., 2005 ("USP/NF"), or a more recent edition, and the components listed in the continuously updated Inactive Ingredient Search online database of the FDA. Other useful components that are not described in the USP/NF, etc. may also be used.

The term "pharmaceutically acceptable excipient," as used herein, can include any and all solvents, dispersion media, coatings, antibacterial and antifungal agents, isotonic, or absorption delaying agents. The use of such media and agents for pharmaceutical active substances is well known in the art (see generally Remington's Pharmaceutical Sciences (A. R. Gennaro, Ed.), 21st edition, ISBN: 0781746736 (2005)). Except insofar as any conventional media or agent is incompatible with an active ingredient, its use in the therapeutic compositions is contemplated. Supplementary active ingredients can also be incorporated into the compositions.

A "stable" formulation or composition can refer to a composition having sufficient stability to allow storage at a convenient temperature, such as between about 0° C. and about 60° C., for a commercially reasonable period of time, such as at least about one day, at least about one week, at least about one month, at least about three months, at least about six months, at least about one year, or at least about two years.

The formulation should suit the mode of administration. The agents of use with the current disclosure can be formulated by known methods for administration to a subject using several routes which include, but are not limited to oral, parenteral, pulmonary, topical, intradermal, intramuscular, intraperitoneal, intravenous, subcutaneous, intranasal, epidural, ophthalmic, buccal, and rectal. The individual agents may also be administered in combination with one or more additional agents or together with other biologically active or biologically inert agents. Such biologically active or inert agents may be in fluid or mechanical communication with the agent(s) or attached to the agent(s) by ionic, covalent, Van der Waals, hydrophobic, hydrophilic or other physical forces.

Controlled-release (or sustained-release) preparations may be formulated to extend the activity of the agent(s) and reduce dosage frequency. Controlled-release preparations can also be used to effect the time of onset of action or other characteristics, such as blood levels of the agent, and consequently affect the occurrence of side effects. Controlled-release preparations may be designed to initially release an amount of an agent(s) that produces the desired therapeutic effect, and gradually and continually release other amounts of the agent to maintain the level of therapeutic effect over an extended period of time. In order to maintain a near-constant level of an agent in the body, the agent can be released from the dosage form at a rate that will replace the amount of agent being metabolized or excreted from the body. The controlled-release of an agent may be stimulated by various inducers, e.g., change in pH, change in temperature, enzymes, water, or other physiological conditions or molecules.

Agents or compositions described herein can also be used in combination with other therapeutic modalities, as described further below. Thus, in addition to the therapies described herein, one may also provide to the subject other therapies known to be efficacious for treatment of the disease, disorder, or condition.

Therapeutic Methods

Also provided is a process of treating preventing, or reducing an allergic disorder, treating sepsis (e.g., late onset sepsis); or treating necrotizing in a subject in need of administration of a therapeutically effective amount of an EGFR ligand, so as to modulate colonic antigen uptake or exposure comprising administering an effective amount of an EGFR ligand, regulate antigen exposure, promote RORγt+iTreg development and maintenance, or modulate Th2 related immunoglobulins and cytokines.

Methods described herein are generally performed on a subject in need thereof. A subject in need of the therapeutic methods described herein can be a subject having, diagnosed with, suspected of having, or at risk for developing allergic disorder, sepsis, or necrotizing enterocolitis (NEC). A determination of the need for treatment will typically be assessed by a history and physical exam consistent with the disease or condition at issue. Diagnosis of the various conditions treatable by the methods described herein is within the skill of the art.

Generally, a safe and effective amount of an EGFR ligand is, for example, that amount that would cause the desired therapeutic effect in a subject while minimizing undesired side effects. In various embodiments, an effective amount of an EGFR ligand described herein can substantially inhibit allergic disorder, sepsis, or necrotizing enterocolitis (NEC), slow the progress of allergic disorder, sepsis, or necrotizing enterocolitis (NEC), or limit the development of allergic disorder, sepsis, or necrotizing enterocolitis (NEC).

According to the methods described herein, administration can be parenteral, pulmonary, oral, topical, intradermal, intramuscular, intraperitoneal, intravenous, subcutaneous, intranasal, epidural, ophthalmic, buccal, or rectal administration.

The composition comprising the EGFR ligand can be administered one or more times a day, optionally with one or more feedings. For example, the EGFR ligand can be administered to the subject once per day, twice per day, three times per day, four times per day, five times per day, six times per day, etc.

When used in the treatments described herein, a therapeutically effective amount of an EGFR ligand can be employed in pure form or, where such forms exist, in pharmaceutically acceptable salt form and with or without a pharmaceutically acceptable excipient. For example, the compounds of the so as to modulate colonic antigen uptake or exposure comprising administering an effective amount of an EGFR ligand, regulate antigen exposure, promote RORγt+iTreg development and maintenance, or modulate Th2 related immunoglobulins and cytokines.

The amount of a composition described herein that can be combined with a pharmaceutically acceptable carrier to produce a single dosage form will vary depending upon the host treated and the particular mode of administration. It will be appreciated by those skilled in the art that the unit content of agent contained in an individual dose of each dosage form need not in itself constitute a therapeutically effective amount, as the necessary therapeutically effective amount could be reached by administration of a number of individual doses.

Toxicity and therapeutic efficacy of compositions described herein can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$, where larger therapeutic indices are generally understood in the art to be optimal.

The specific therapeutically effective dose level for any particular subject will depend upon a variety of factors including the disorder being treated and the severity of the disorder; activity of the specific compound employed; the specific composition employed; the age, body weight, general health, sex and diet of the subject; the time of administration; the route of administration; the rate of excretion of the composition employed; the duration of the treatment; drugs used in combination or coincidental with the specific compound employed; and like factors well known in the medical arts (see e.g., Koda-Kimble et al. (2004) Applied Therapeutics: The Clinical Use of Drugs, Lippincott Williams & Wilkins, ISBN 0781748453; Winter (2003) Basic Clinical Pharmacokinetics, $4^{th}$ ed., Lippincott Williams & Wilkins, ISBN 0781741475; Sharqel (2004) Applied Biopharmaceutics & Pharmacokinetics, McGraw-Hill/Appleton & Lange, ISBN 0071375503). For example, it is well within the skill of the art to start doses of the composition at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose. It will be understood, however, that the total daily usage of the compounds and compositions of the present disclosure will be decided by an attending physician within the scope of sound medical judgment.

Again, each of the states, diseases, disorders, and conditions, described herein, as well as others, can benefit from compositions and methods described herein. Generally, treating a state, disease, disorder, or condition includes preventing or delaying the appearance of clinical symptoms in a mammal that may be afflicted with or predisposed to the state, disease, disorder, or condition but does not yet experience or display clinical or subclinical symptoms thereof. Treating can also include inhibiting the state, disease, disorder, or condition, e.g., arresting or reducing the development of the disease or at least one clinical or subclinical symptom thereof. Furthermore, treating can include relieving the disease, e.g., causing regression of the state, disease, disorder, or condition or at least one of its clinical or subclinical symptoms. A benefit to a subject to be treated can be either statistically significant or at least perceptible to the subject or to a physician.

Administration of an EGFR ligand can occur as a single event or over a time course of treatment. For example, an EGFR ligand can be administered daily, weekly, bi-weekly, or monthly. For treatment of acute conditions, the time course of treatment will usually be at least several days. Certain conditions could extend treatment from several days to several weeks. For example, treatment could extend over one week, two weeks, or three weeks. For more chronic conditions, treatment could extend from several weeks to several months or even a year or more.

Treatment in accord with the methods described herein can be performed prior to, concurrent with, or after conventional treatment modalities for allergic disorder, sepsis, or necrotizing enterocolitis (NEC).

The methods and compositions as described herein can be used with conventional treatments for allergic disorders. Conventional treatments for allergies can include avoiding known allergens and the use of medications such as steroids and antihistamines. Early exposure to potential allergens may be protective. In severe reactions injectable adrenaline (epinephrine) is recommended. Allergen immunotherapy, which gradually exposes people to larger and larger amounts of allergen, is useful for some types of allergies such as hay fever and reactions to insect bites. Conventional therapy for food allergies can include oral immunotherapy (OIT), which presents significant risks and challenges because it must be tailored to each individual and requires regular exposure to allergenic foods to maintain tolerance. Furthermore, while OIT has been successful for milk, egg, and peanut allergies, there is limited information on its efficacy for other allergies (e.g., fish, wheat).

An EGFR ligand can be administered simultaneously or sequentially with another agent, such as an antibiotic, an anti-inflammatory, a probiotic, a prebiotic, or another agent. For example, an EGFR ligand can be administered simultaneously with another agent, such as a probiotic, a prebiotic, an antibiotic, or an anti-inflammatory. Simultaneous administration can occur through administration of separate compositions, each containing one or more of an EGFR ligand, a probiotic, a prebiotic, an antibiotic, an anti-inflammatory, or another agent. Simultaneous administration can occur through administration of one composition containing two or more of an EGFR ligand, a probiotic, a prebiotic, an antibiotic, an anti-inflammatory, or another agent. An EGFR ligand can be administered sequentially with a probiotic, a prebiotic, an antibiotic, an anti-inflammatory, or another agent. For example, an EGFR ligand can be administered before or after administration of a probiotic, a prebiotic, an antibiotic, an anti-inflammatory, or another agent.

Administration

Agents and compositions described herein can be administered according to methods described herein in a variety of means known to the art. The agents and composition can be used therapeutically either as exogenous materials or as endogenous materials. Exogenous agents are those produced or manufactured outside of the body and administered to the body. Endogenous agents are those produced or manufactured inside the body by some type of device (biologic or other) for delivery within or to other organs in the body.

As discussed above, administration can be parenteral, pulmonary, oral, topical, intradermal, intramuscular, intraperitoneal, intravenous, subcutaneous, intranasal, epidural, ophthalmic, buccal, or rectal administration.

Agents and compositions described herein can be administered in a variety of methods well known in the arts. Administration can include, for example, methods involving oral ingestion, direct injection (e.g., systemic or stereotactic), implantation of cells engineered to secrete the factor of interest, drug-releasing biomaterials, polymer matrices, gels, permeable membranes, osmotic systems, multilayer coatings, microparticles, implantable matrix devices, mini-osmotic pumps, implantable pumps, injectable gels and hydrogels, liposomes, micelles (e.g., up to 30 µm), nanospheres (e.g., less than 1 µm), microspheres (e.g., 1-100 µm), reservoir devices, a combination of any of the above, or other suitable delivery vehicles to provide the desired release profile in varying proportions. Other methods of controlled-release delivery of agents or compositions will be known to the skilled artisan and are within the scope of the present disclosure.

Delivery systems may include, for example, an infusion pump which may be used to administer the agent or composition in a manner similar to that used for delivering insulin or chemotherapy to specific organs or tumors. Typically, using such a system, an agent or composition can be administered in combination with a biodegradable, biocompatible polymeric implant that releases the agent over a controlled period of time at a selected site. Examples of polymeric materials include polyanhydrides, polyorthoesters, polyglycolic acid, polylactic acid, polyethylene vinyl acetate, and copolymers and combinations thereof. In addition, a controlled release system can be placed in proximity of a therapeutic target, thus requiring only a fraction of a systemic dosage.

Agents can be encapsulated and administered in a variety of carrier delivery systems. Examples of carrier delivery systems include microspheres, hydrogels, polymeric implants, smart polymeric carriers, and liposomes (see generally, Uchegbu and Schatzlein, eds. (2006) Polymers in Drug Delivery, CRC, ISBN-10: 0849325331). Carrier-based systems for molecular or biomolecular agent delivery can: provide for intracellular delivery; tailor biomolecule/agent release rates; increase the proportion of biomolecule that reaches its site of action; improve the transport of the drug to its site of action; allow colocalized deposition with other agents or excipients; improve the stability of the agent in vivo; prolong the residence time of the agent at its site of action by reducing clearance; decrease the nonspecific delivery of the agent to nontarget tissues; decrease irritation caused by the agent; decrease toxicity due to high initial doses of the agent; alter the immunogenicity of the agent; decrease dosage frequency, improve taste of the product; or improve shelf life of the product.

Kits

Also provided are kits. Such kits can include an agent or composition described herein and, in certain embodiments, instructions for administration. Such kits can facilitate performance of the methods described herein. When supplied as a kit, the different components of the composition can be packaged in separate containers and admixed immediately before use. Components include, but are not limited to an EGFR ligand, pharmaceutical compositions comprising an EGFR ligand, or food or infant formula comprising an EGFR ligand. Such packaging of the components separately can, if desired, be presented in a pack, dropper bottle, or dispenser device which may contain one or more unit dosage forms containing the composition. The pack may, for example, comprise a dropper bottle or metal or plastic foil such as a blister pack. Such packaging of the components separately can also, in certain instances, permit long-term storage without losing activity of the components.

Kits may also include reagents in separate containers such as, for example, sterile water or saline to be added to a lyophilized active component packaged separately. For example, sealed glass ampules may contain a lyophilized component and in a separate ampule, sterile water, sterile saline or sterile each of which has been packaged under a neutral non-reacting gas, such as nitrogen. Ampules may consist of any suitable material, such as glass, organic polymers, such as polycarbonate, polystyrene, ceramic, metal or any other material typically employed to hold reagents. Other examples of suitable containers include bottles that may be fabricated from similar substances as ampules, and envelopes that may consist of foil-lined interiors, such as aluminum or an alloy. Other containers include canister optionally with a scoop, dropper bottles, test tubes, vials, flasks, bottles, syringes, and the like. Containers may have a food grade access, such as a bottle having a dropper that can be used to measure a dose in drops. Other containers may have a food formulation comprising the composition.

In certain embodiments, kits can be supplied with instructional materials. Instructions may be printed on paper or other substrate, and/or may be supplied as an electronic-readable medium, such as a floppy disc, mini-CD-ROM, CD-ROM, DVD-ROM, Zip disc, videotape, audio tape, and the like. Detailed instructions may not be physically associated with the kit; instead, a user may be directed to an Internet web site specified by the manufacturer or distributor of the kit.

Compositions and methods described herein utilizing molecular biology protocols can be according to a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754; Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including in the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

All publications, patents, patent applications, and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1

Regulatory T-Cells Restraining Allergic Responses Develop Under Maternal Control The following example describes the discovery that temporal compositional changes in breast milk (1) control exposure to gut luminal substances and (2) support the development of regulatory T-cells restraining Th2 responses in the offspring.

Initial exposure to dietary and microbial antigens via the GI tract prior to weaning is associated with immune tolerance and a reduced risk for developing allergy. A delayed type hypersensitivity (DTH) assay was used to determine the optimal time to introduce oral antigens to generate tolerance to the food allergen chicken egg ovalbumin (Ova). Ova is effectively delivered to nursing mice via breast milk, and mice receiving dietary Ova on days of life (DOL) 11-21, had significantly less robust DTH response to Ova 15 weeks later than mice not receiving Ova, or mice receiving dietary Ova on DOL 0-10, or after weaning on DOL 28-38, or as adults on DOL 42-52 (see e.g., FIG. 1A-FIG. 1B). The non-Peyer's Patch or non-colonic patch-bearing epithelium is where luminal antigens are captured by lamina propria (LP) antigen presenting cells (APCs) to promote tolerance. The inquires of where and when dietary antigen is effectively delivered to the immune system during early life was explored by assessing the ability of APCs from the intestines of mice receiving dietary Ova to stimulate Ova specific T-cells. Dietary antigen is not effectively delivered to the small intestine (SI) LP-APCs or colonic LP-APCs in very early life, but is, instead, delivered to the colonic LP-APCs until the time of weaning, and subsequently delivered almost exclusively to the SI LP-APCs (see e.g., FIG. 1C). Antigen directly introduced into the lumen of the SI or colon of mice on DOL 18 demonstrated that only colonic LP-APCs could induce T-cell proliferation in response to luminal antigen, even though both SI and colon LP-APCs induced T-cell proliferation when supplied exogenous Ova in the culture, indicating they are functional APCs (see e.g., FIG. 2). Therefore the regional and temporal pattern of effective dietary antigen acquisition by LP-APCs results from antigen crossing the intestinal epithelium to be acquired by LP-APCs as opposed to antigen acquisition and APCs and migration to distant sites, or opposed to APC defects. Thus the period in early life optimal to introduce antigens via the GI tract for the induction of tolerance coincides with antigen uptake across the colonic epithelium and effective acquisition by LP-APCs in a manner capable of stimulating immune responses.

Figure 4:
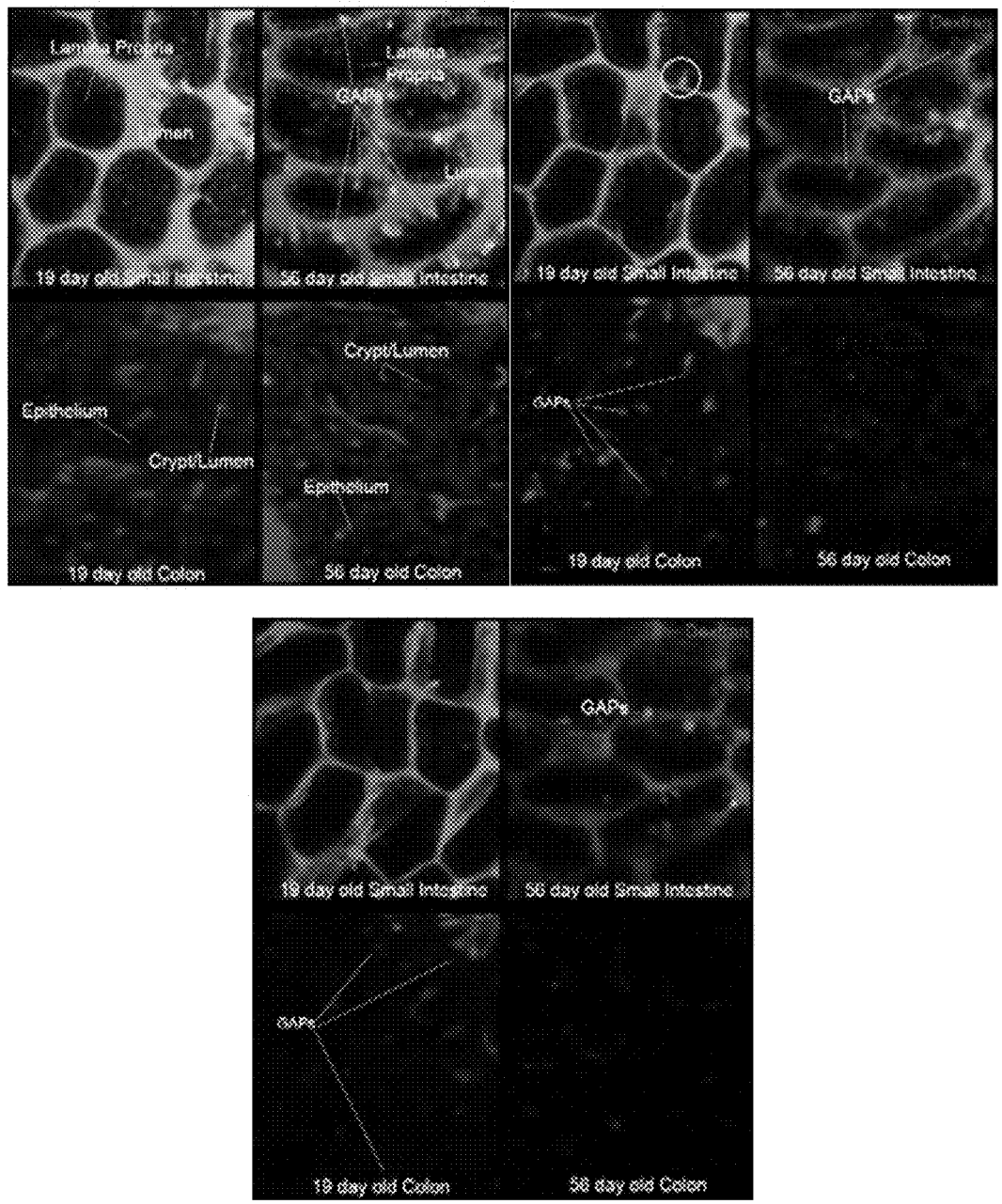
FIG. 4 is a series of still images from a movie showing a montage of z-stacks showing the presence or 284 absence trans-epithelial dextran (red) columns crossing the DAPI stained epithelial nuclei (blue), or GAPs, in the small intestine and colon of adult and infant SPF housed mice.

It was then asked how luminal antigens were acquired by colonic LP-APCs, to better understand this time-limited pattern of antigen uptake in early life. Villous microfold (M) cells in the colon was not observed and paracellular leak did not correlate with the pattern of antigen uptake through early life (see e.g., FIG. 3A-F, FIG. 3O, and FIG. 3P compare with FIG. 1C). Further, the extension of trans-epithelial dendrites (TEDs) by LP-APCs occurred rarely, and was not synchronous with the pattern of dietary antigen uptake in early life (see e.g., FIG. 3G-FIG. 3N compare with FIG. 1C). In contrast, goblet cell associated antigen passages (GAPs) appear in a temporal and regional pattern mirroring the uptake of antigen by LP-APCs throughout early life (see e.g., FIG. 1D-FIG. 1I and FIG. 3R and FIG. 3S). GAPs form in the colon starting at approximately DOL 10 (see e.g., FIG. 1I), are found throughout the colon on the surface of the epithelium and in the crypts (see e.g., FIG. 4), and LP-APCs are physically associated with these GAPs (see e.g., FIG. 1E and FIG. 1H).

Movie 1 (movie not shown, see FIG. 4 for still images of movie), is a montage of z-stacks showing the presence or absence of trans-epithelial dextran (red) columns crossing the DAPI stained epithelial nuclei (blue), or GAPs, in the small intestine and colon of adult and infant SPF housed mice.

Figures 2A, 2B:
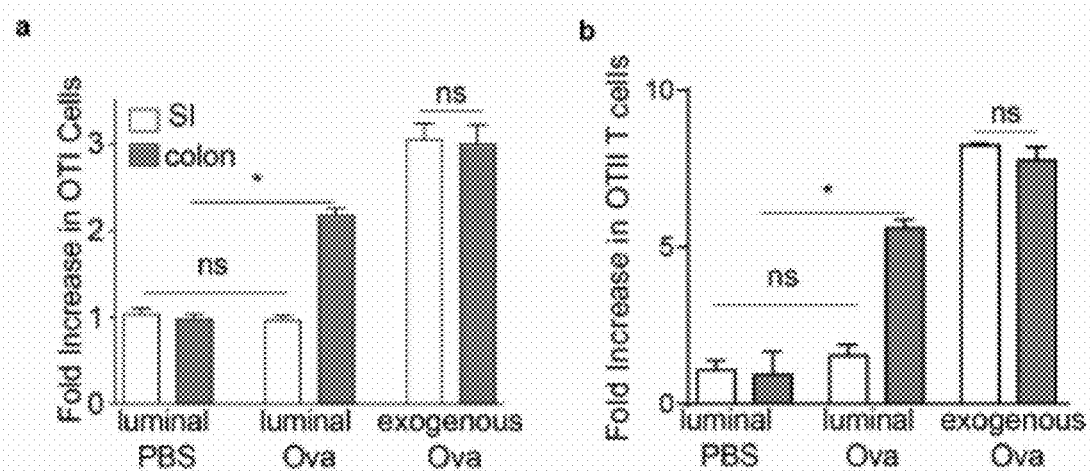
FIG. 2A-FIG. 2B is a series of bar graphs showing functional luminal antigen is delivered to APCs across the colonic but not the small intestine epithelium on DOL 18. Antigen presentation capacity of SI and colon APCs isolated from the LP of 18 day old mice following luminal PBS or Ova as assessed by the increase in Ova specific (FIG. 2A) OTI or (FIG. 2B) OTII T cells following 72 hours of co-culture. n=4 mice per group. Data is presented as mean+/−SEM, *=p<0.05, ns=not significant.
Figures 3A, 3B, 3C, 3D, 3E, 3F, 3G, 3H, 3I, 3J, 3K, 3L:
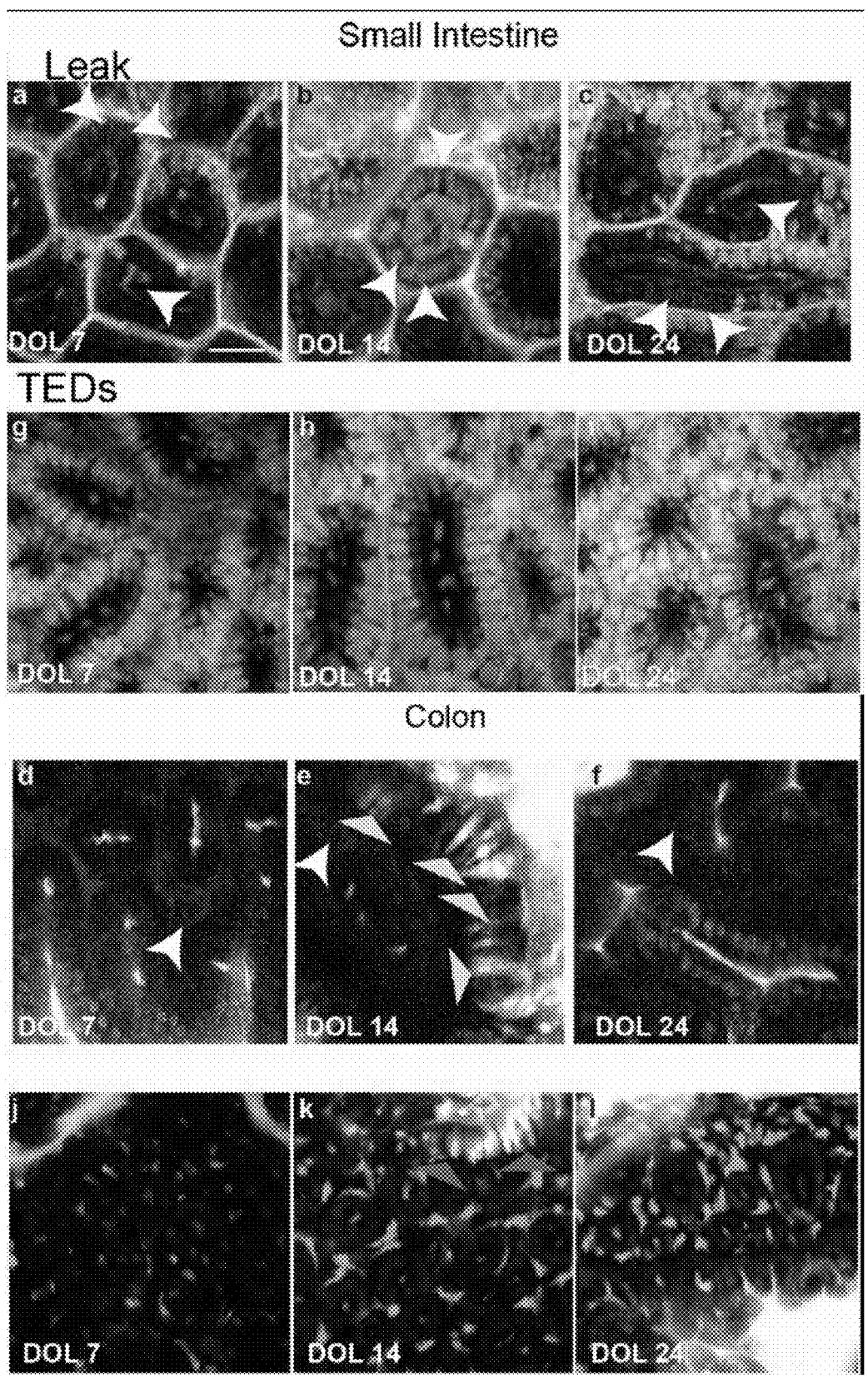
Figures 3T, 3U:
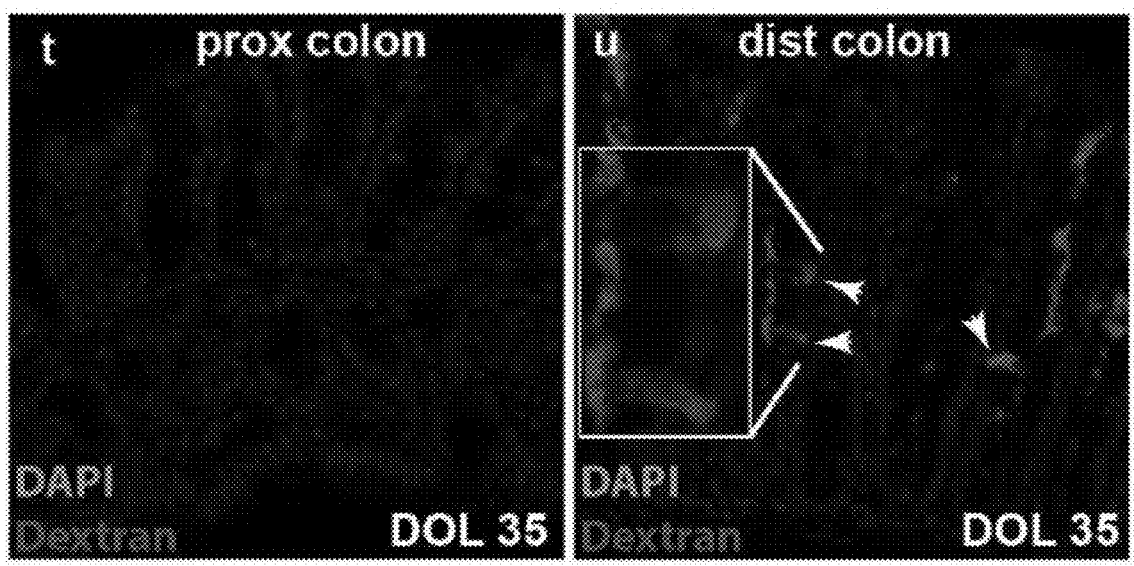

Colonic GAPs were present until weaning, and became sparse around DOL 26 (see e.g., FIG. 1I), with only a few persisting in the distal-most colon (see e.g., FIG. 3T, FIG. 3U). While induction of SI and colonic GAPs did not depend upon the microbiota, as evidenced by the normal timing of SI and colonic GAP formation in germ free mice, colonic GAP inhibition around weaning was microbiota dependent, as colonic GAPs persisted after weaning in germ free mice (see e.g., FIG. 1I). Colonic GAPs were absent in DOL 18 mice lacking goblet cells (GCs; see e.g., FIG. 1J, FIG. 1K), and the effective uptake of luminal antigen by colonic LP-APCs in DOL 18 mice, evidenced by the ability to induce antigen specific T-cell expansion, was abolished in mice lacking GCs (see e.g., FIG. 1L). Small intestine GAPs did not consistently appear until DOL ~18, despite the presence of GCs (see e.g., FIG. 3Q), and effective uptake of luminal antigen by SI APCs occurred after DOL 20 (see e.g., FIG. 1C and FIG. 2). This timing and sequence indicate that the window of optimal tolerance induction coincides with the presence of colonic GAPs, and the GC-dependent uptake of luminal antigen by colonic LP-APCs.

Figures 5A, 5B, 5C, 5D:
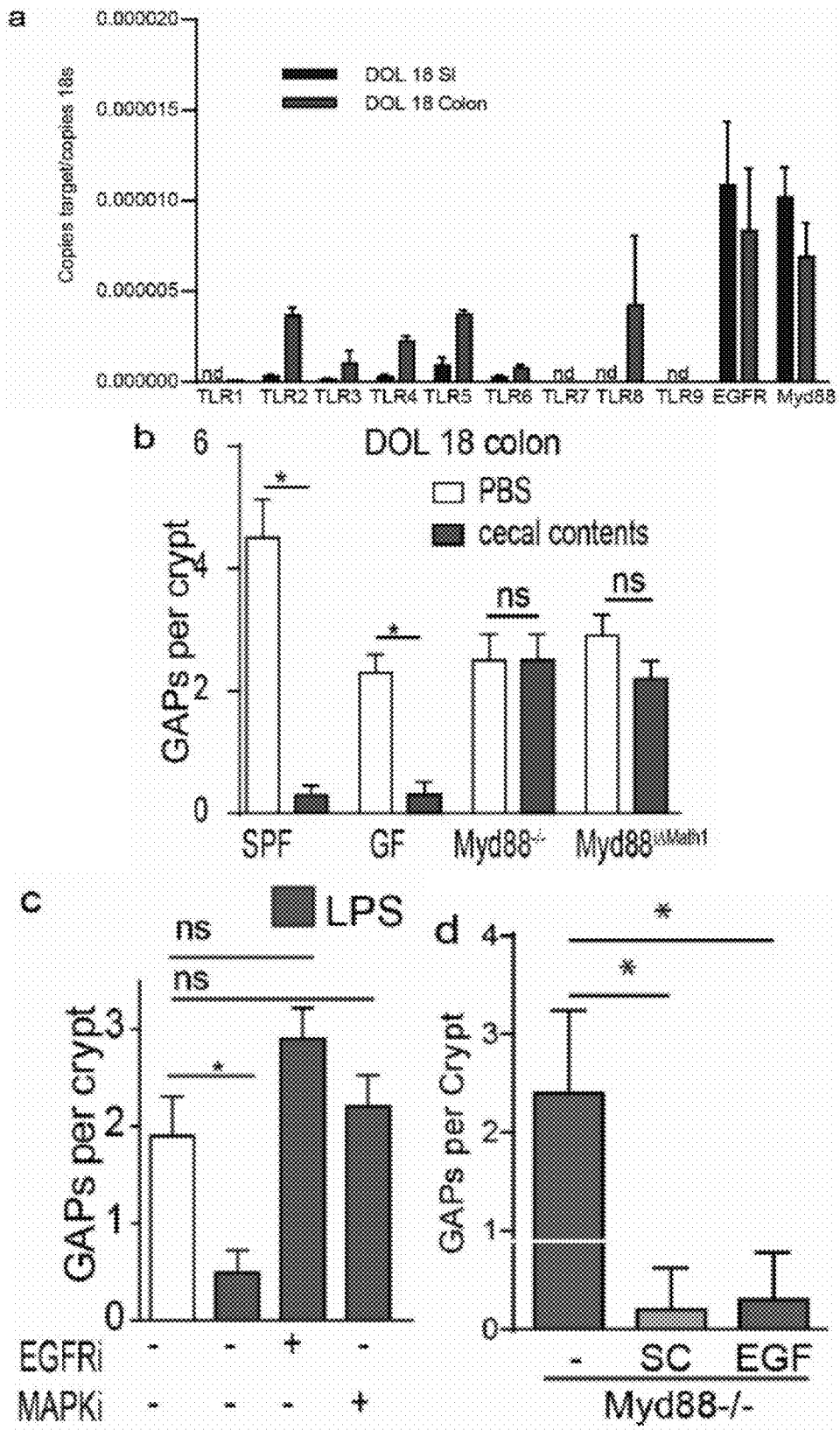
FIG. 5A-FIG. 5D are a series of bar graphs showing goblet cells in the gut in early life express TLRs, Myd88, and the EGFR, and GAPs in the colon at DOL 18 are inhibited by microbial products in a manner dependent upon the EGFR and p42/p44 MAPK activation and by stomach contents from a nursing mouse (breast milk) in a Myd88 independent manner.
Figures 6A, 6B, 6C, 6D, 6E:
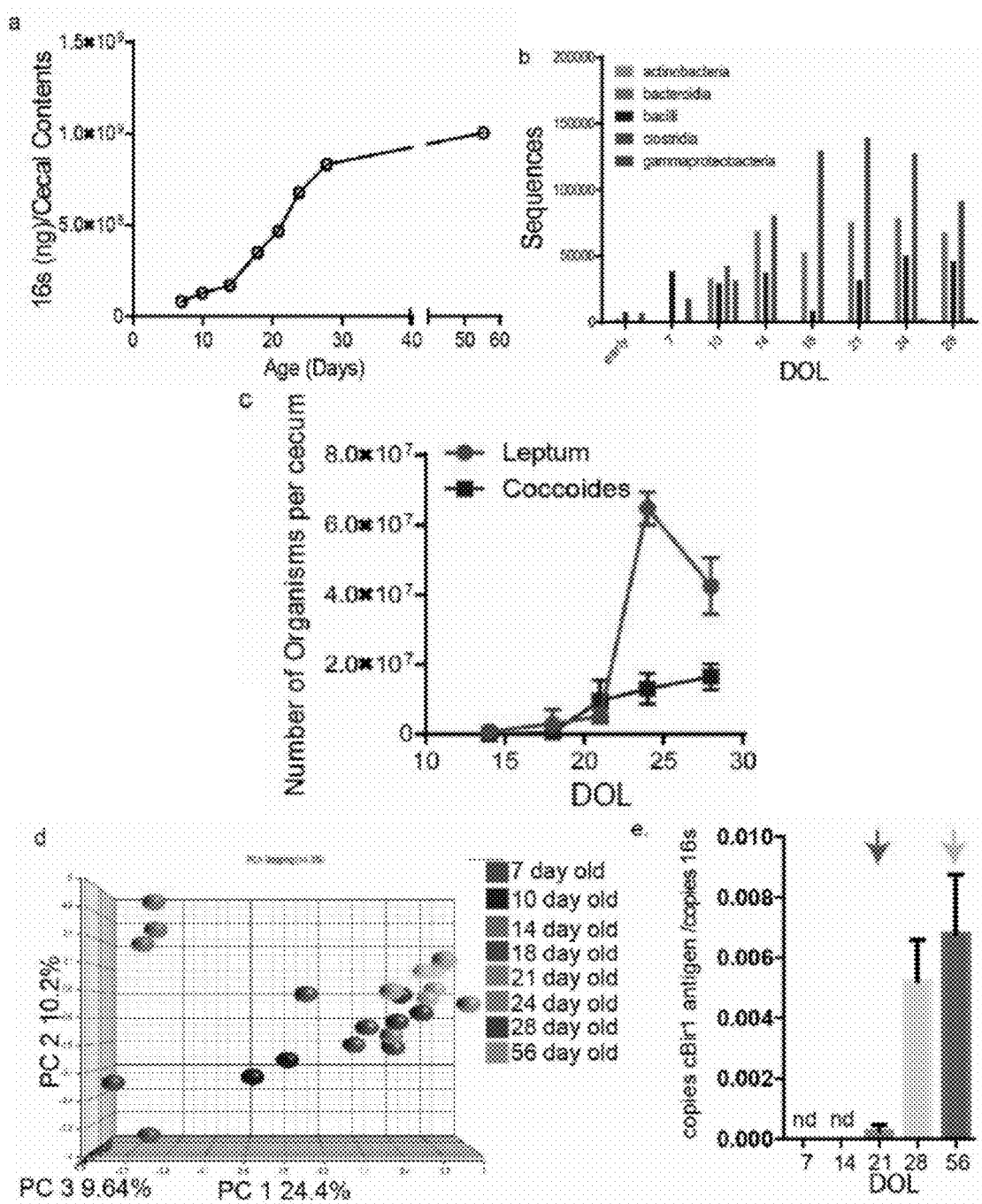
FIG. 6A-FIG. 6E is a series of graphs showing quantitative and qualitative changes in the colonic luminal microbiota during early life.
Figure 7:
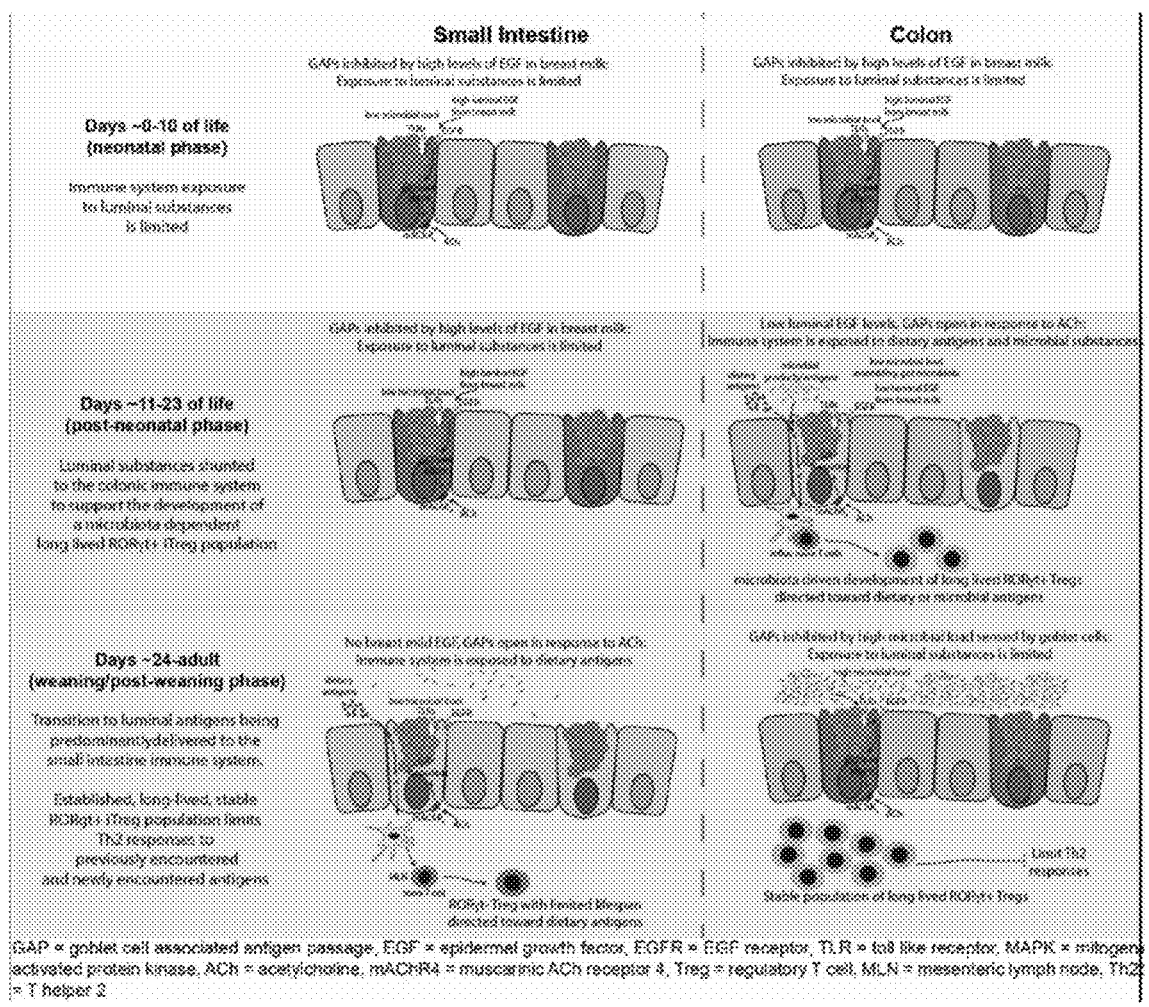
FIG. 7 is a schematic illustrating GAP formation in early life is driven by the same stimuli and regulation pathways as in adults, but the GC responsiveness to ACh alters throughout the phases in early life; termed here as the neonatal phase, DOL ~0-10 when luminal antigens are not effectively delivered to the gut immune system, the post-neonatal phase, DOL ~11-23, when antigens are delivered predominantly to the colonic immune system, and the weaning/post weaning phase, after DOL ~24 to adulthood, when antigen delivery switches to favor the SI immune system.

In adults, GAPs are formed by acetylcholine (ACh) action on the muscarinic ACh receptor 4 ($mAChR_4$) expressed by GCs, and are inhibited by trans-activation of the epidermal growth factor receptor (EGFR) via GC-intrinsic Myd88-dependent sensing of the microbiota or by direct activation of the EGFR by luminal EGF. The ACh analogue carbamylcholine (CCh) does not induce SI or colonic GAPs at DOL 8 (see e.g., FIG. 1M). At DOL 15 SI GCs were relatively unresponsive to CCh, while at DOL 15 colonic GAPs formed robustly in response to CCh. Moreover, spontaneously forming colonic GAPs at DOL 15 were suppressed by $mAChR_4$ antagonist (see e.g., FIG. 1M). In contrast, at DOL 28, post weaning, GCs responded similarly to that reported in adults with SI GCs responding to CCh to spontaneously form GAPs via $mAChR_4$ signals, and colonic GCs not forming GAPS and being unresponsive to CCh (see e.g., FIG. 1M). Additional data support that the same pathways regulate GAP formation in early life and in adulthood: Cecal contents from adult specific pathogen free (SPF) mice inhibit colonic GAPs at DOL 18 in a Myd88-dependent manner, as does LPS via activation of the epidermal growth factor receptor (EGFR) and downstream activation of p42/p44 mitogen activated protein kinase (MAPK; FIG. 5B, FIG. 5C). Moreover, the expression of TLRs, Myd88 and EGFR by GCs in early life is comparable to that of adult GCs (see e.g., FIG. 5A) and inhibition of colonic GAPs correlates with quantitative and qualitative changes in the gut microbial community (compare FIG. 1I and FIG. 6A-FIG. 6D). Thus GAP formation in early life is driven by the same stimuli and regulation pathways as in adults, but the GC responsiveness to ACh alters throughout the phases in early life; termed here as the neonatal phase, DOL ~0-10 when luminal antigens are not effectively delivered to the gut immune system, the post-neonatal phase, DOL ~11-23, when antigens are delivered predominantly to the colonic immune system, and the weaning/post weaning phase, after DOL ~24 to adulthood, when antigen delivery switches to favor the SI immune system (see e.g., FIG. 7). These alterations in GC responsiveness allow a choreographed pattern of antigen delivery to the developing gut immune system.

Figures 8A, 8B, 8C, 8D, 8E, 8F, 8G, 8H, 8I, 8J, 8K, 8L, 8M:
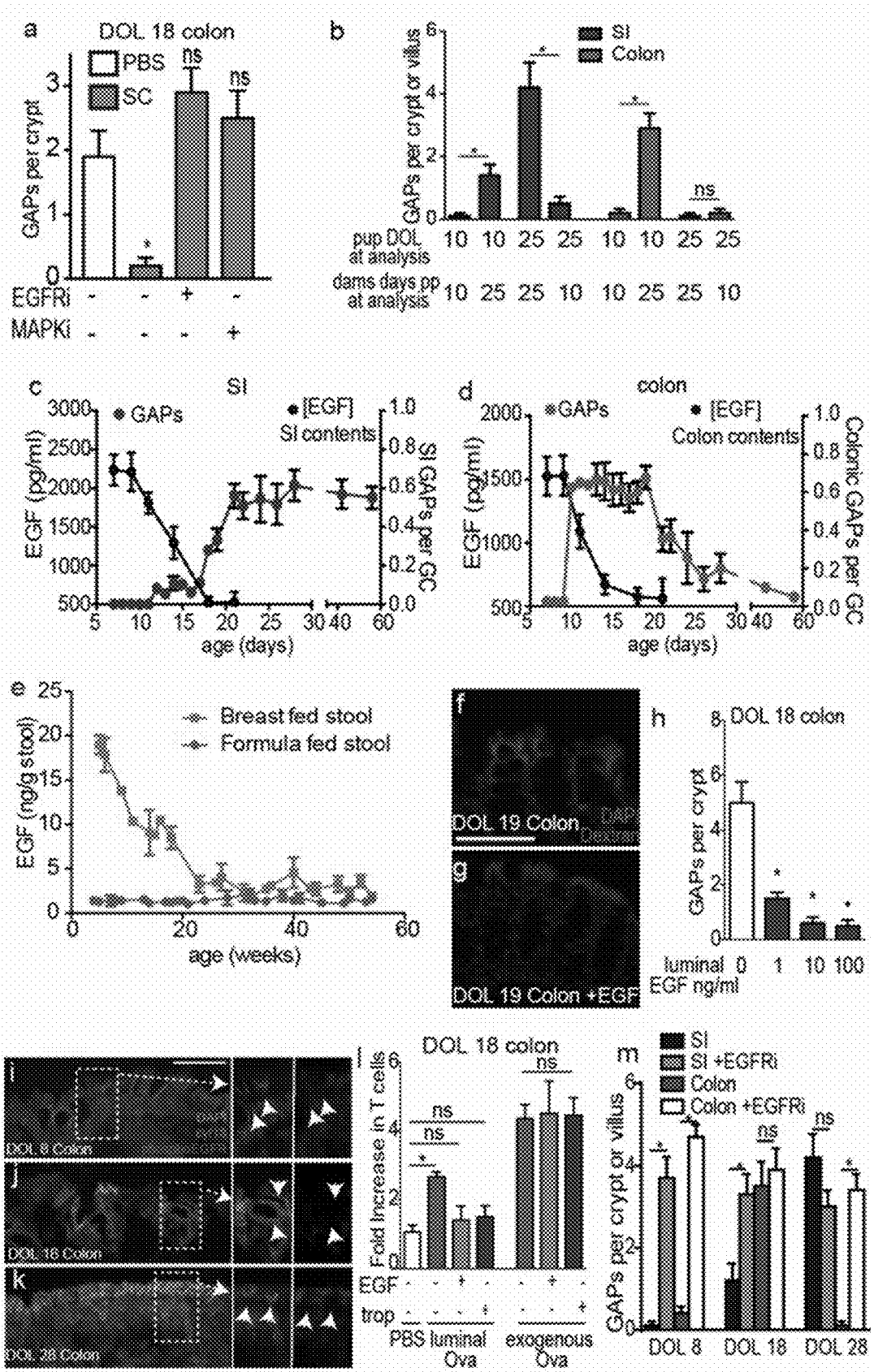
FIG. 8A-FIG. 8M are a series of graphs and images showing maternal control of GAP formation and luminal antigen delivery in the offspring occurs via a temporal pattern of EGF delivered in breast milk.

Breast milk promotes oral tolerance. Therefore it was hypothesized that breast milk might control luminal antigen delivery in nursing offspring. It was found that stomach contents obtained on DOL 10, i.e., largely breast milk, inhibits GAPs in the post-neonatal phase DOL 18 colon in an EGFR and p42/p44 MAPK-dependent, but Myd88-independent, manner (see e.g., FIG. 8 and FIG. 5D). To recapitulate GAP formation in offspring in the observed regional and temporal pattern, breast milk would need varying effects throughout lactation, i.e., inhibiting GAP formation in the neonatal phase before DOL 10, and then allowing GAPs to form sequentially in the colon and the SI. This prediction was evaluated by synchronously and asynchronously cross-fostering (CF) mice and assessing GAP formation in offspring 10 days later. Newborn mice asynchronously CF to dams two weeks post-partum (pp) had increased GAP density in the SI and colon at DOL 10. Conversely, SI gaps in DOL 15 mice asynchronously CF to dams one day pp were suppressed at DOL 25 when compared to synchronous CF controls (see e.g., FIG. 8B). These data support that breast milk from recently-delivered dams contains factors that can suppress GAPs, and that the milk loses these factors over the first few weeks pp. There was no significant difference in the number of colonic GAPs between the groups of CF mice at DOL 25 indicating that colonic GAPs are not under maternal control at this time (values were low in both groups, as expected in mice of this age; see e.g., FIG. 8B compare with FIG. 1I). Thus the pathway delivering enteric antigens to the offsprings' immune system in this window for enhanced tolerance is under maternal control, indicating that mothers and their offspring are synchronized to promote the proper immune development.

Figures 9A, 9B:
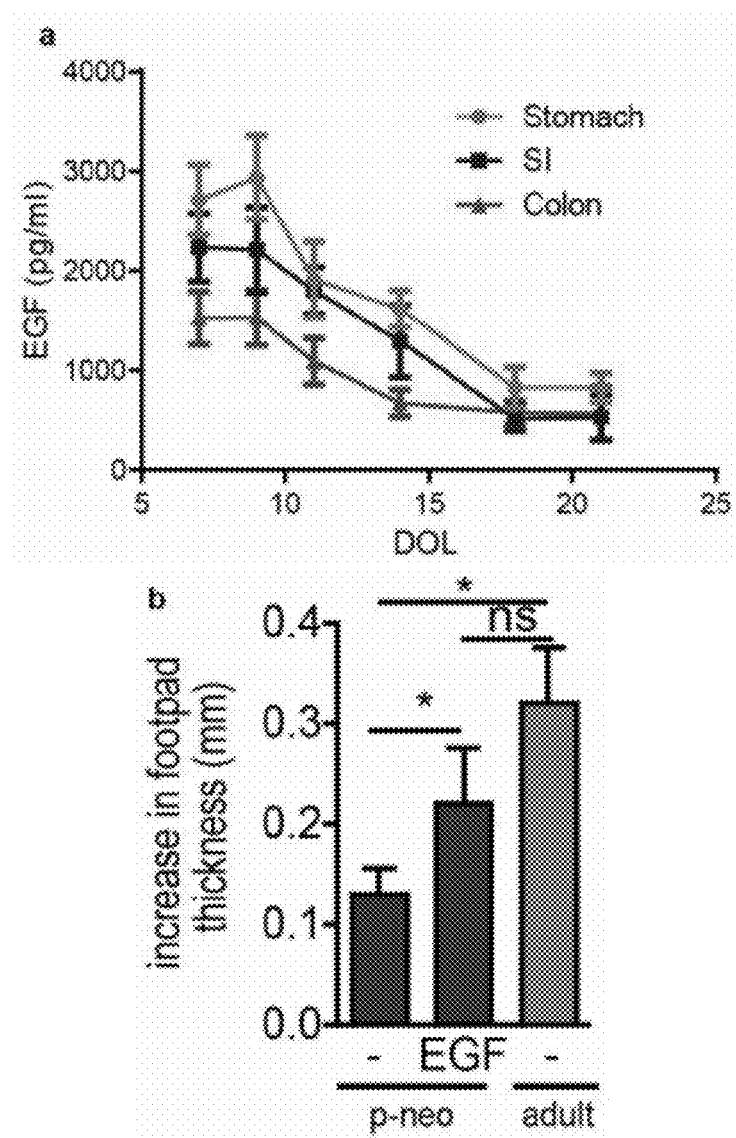
FIG. 9A-FIG. 9B is a series of graphs showing EGF is present in the gut lumen in a proximal to distal gradient and decreases with time through early life and luminal EGF abrogates tolerance to luminal antigen in the colon in the post-neonatal phase.
Figures 10A, 10B, 10C, 10D, 10E, 10F, 10G, 10H, 10I, 10J, 10K, 10L:
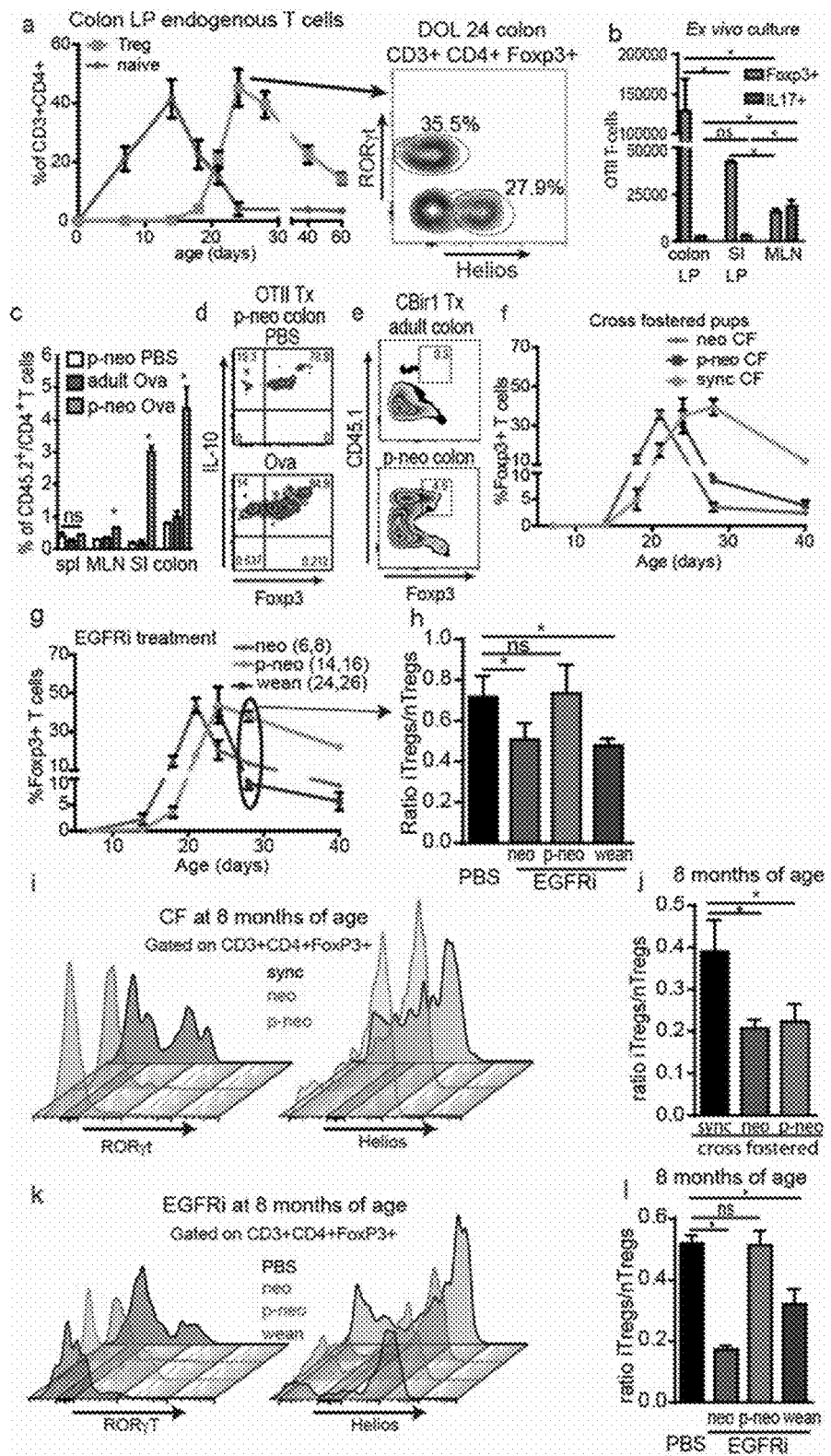
FIG. 10A-FIG. 10L are a series of graphs and maps showing colonic RORγt+ iTreg development and maintenance occurs during a critical window of time in early life and is under maternal control.
Figures 11A, 11B, 11C, 11D, 11E, 11F:
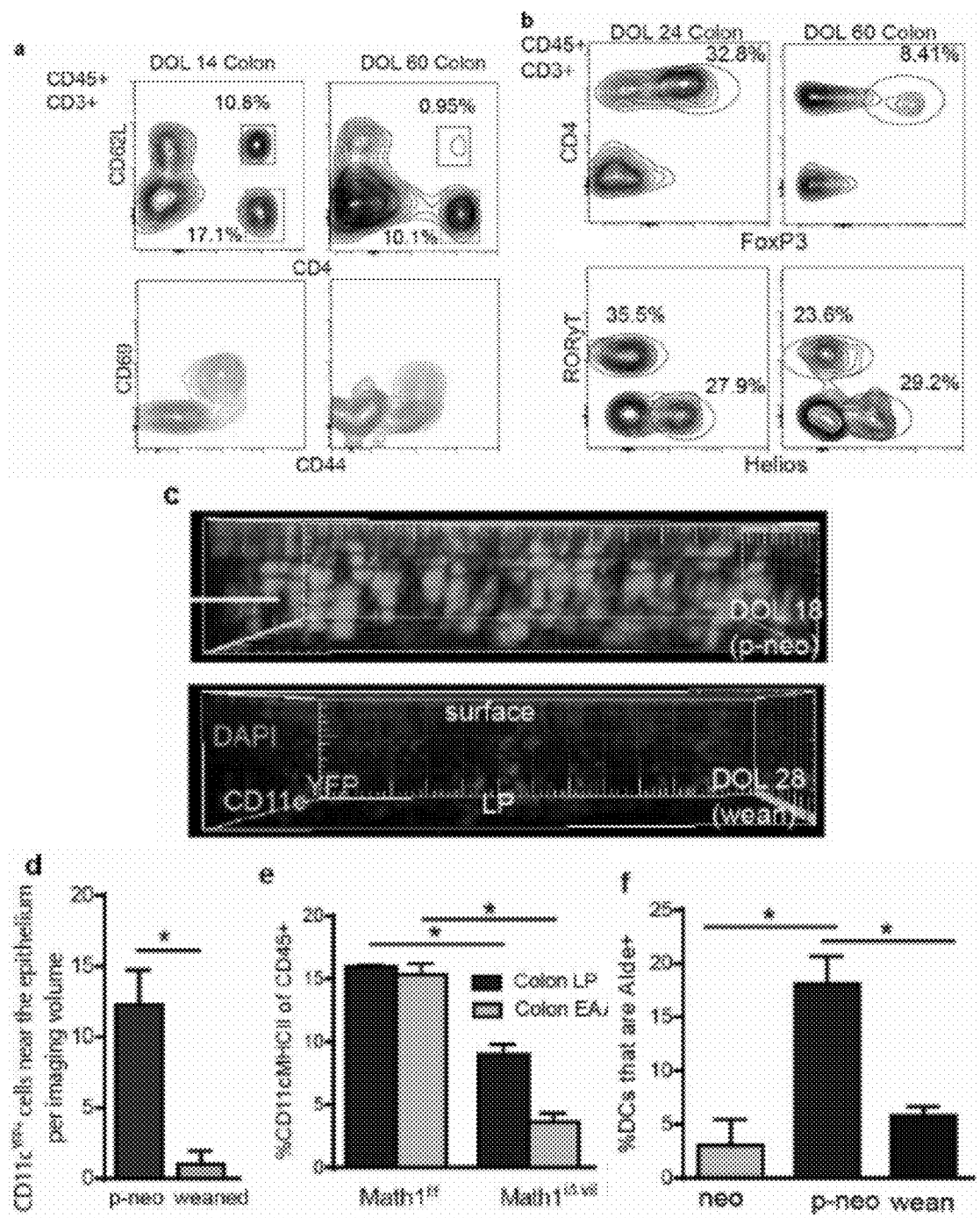
FIG. 11A-FIG. 11F is a series of maps, images, and bar graphs showing the characteristics of T cells and APCs in the colon in early life.
Figures 12A, 12B, 12C, 12D, 12E:
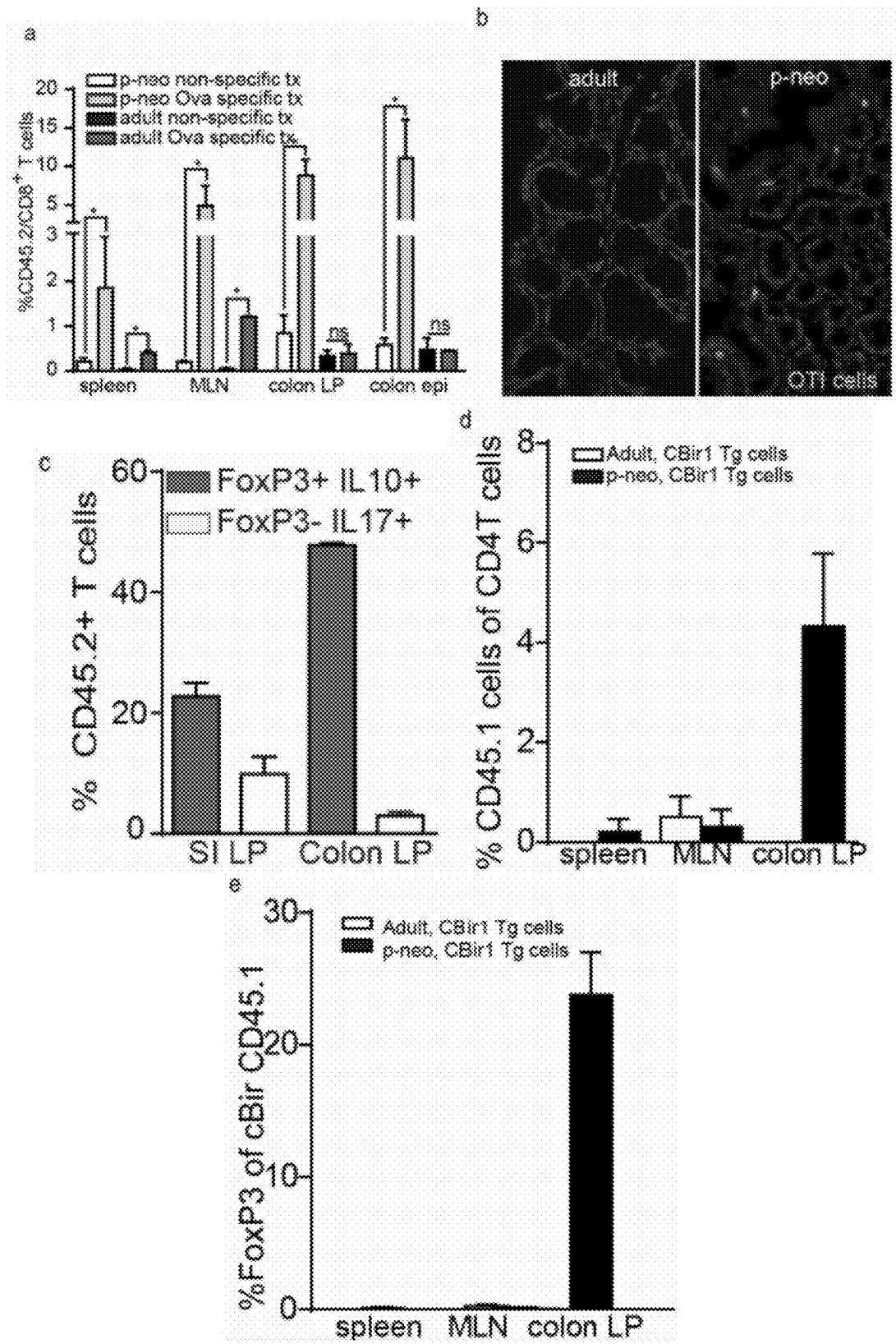
FIG. 12A-FIG. 12E is a series of bar graphs and images showing T cells specific for dietary and commensal antigens localize to the colon during the post-neonatal phase. Naive Ova specific splenic CDS+ OTI T cells, naive Ova specific splenic CD4+ OTII T cells, naive splenic T cells from wildtype mice, or commensal flagellin specific splenic CD4+ CBir1 T cells were adoptively into mice during the post-neonatal phase (p-neo) or adult mice and then given Ova in drinking water, for OTI and OTII adoptive transfers, or drinking water alone.

EGFR ligands, particularly EGF, are abundant in immediate pp breast milk, and then decrease throughout lactation. Furthermore, breast milk EGF reaches the infant GI tract in a biologically active form. In support of the prediction that breast milk is the source of EGF in the offspring's GI tract, and consistent with the temporal and regional pattern of GAP formation, the highest EGF levels in the lumen of the proximal GI tract were found immediately after birth with EGF levels progressively decreasing in the distal GI tract and decreasing throughout lactation (see e.g., FIG. 8C-FIG. 8D and FIG. 9A). Furthermore, stools obtained from breast fed children, but not from formula fed children, had greater EGF levels that decreased throughout the first 30 weeks of life (see e.g., FIG. 8E), similar to the pattern seen in the colonic contents of nursing mice (see e.g., FIG. 8D), suggesting that this window opens in humans around week of life 20. Colonic and SI GCs formed GAPs when the luminal EGF concentration decreased to <~1000 µg/ml on DOL ~10 (colon) and DOL ~18 (SI) (see e.g., FIG. 8C and FIG. 8D), a concentration that inhibits GAPs on short term exposure (see e.g., FIG. 8F-FIG. 8H). Furthermore GC EGFR phosphorylation inversely correlates with the presence of colonic GAPs in early life (see e.g., FIG. 8I-FIG. 8K). Colonic APCs from DOL 18 mice given luminal EGF or $mAChR_4$ blockade concurrent with luminal Ova were impaired at expanding Ova-specific T-cells, but were able to expand T-cells when given exogenous Ova in the culture (see e.g., FIG. 8L), indicating that EGF and $mAChR_4$ antagonist inhibit effective antigen uptake by colonic APCs in vivo. Moreover inhibition of colonic GAPs by luminal EGF abrogated tolerance to luminal Ova in the post-neonatal phase colon (see e.g., FIG. 9), demonstrating that luminal EGF alone could inhibit antigen uptake and subsequent immune outcomes in vivo. EGFR inhibition (EGFRi) induced colonic and SI GAPs in DOL 8 mice, SI GAPs in DOL 18 mice, and colonic GAPs in DOL 28 mice (see e.g., FIG. 8M). This indicates that EGFR activation either via EGF in breast milk in the SI from DOL ~0-18 or colon from DOL ~0-10 or EGFR trans-activation via colonic GCs microbial sensing around weaning, suppress GAPs and control antigen exposure. Therefore exposure of the offspring's intestinal immune system to luminal substances prior to weaning is under maternal control and guided by a temporal pattern of breast milk EGF.

iTregs mediate tolerance to environmental antigens, and the loss or dysfunction of these cells can be associated with exaggerated Th2 responses. iTreg induction requires antigen, naïve T-cells, and APCs with tolerogenic properties and/or a tolerogenic environment. It was observed that the appearance of naïve T-cells within the colonic LP temporally coincides with the presence of colonic GAPs and the timing of luminal antigen uptake by colonic LP-APCs (see e.g., FIG. 10A and FIG. 11A, compare with FIG. 1C and FIG. 1I). The colonic LP naïve T-cell population regressed at weaning, and approximately one week following the peak of naïve T cells an abundance of iTregs expressing RORγt appeared in the colonic LP (see e.g., FIG. 10A and FIG. 11B). The kinetics of the naïve T-cell and Treg populations in colonic LP are consistent with the timing of the conversion of naïve T-cells to iTregs, suggesting that antigens and/or other substances delivered via colonic GAPs during this interval drive iTreg formation. Colonic LP cell populations from DOL 18 mice significantly promoted Treg development, but not the differentiation of all T helper cell subsets, when compared to cellular populations from the infant SI LP and infant MLN (see e.g., FIG. 10B). Further, adoptively transferred naïve Ova specific T-cells preferentially localized to the colonic LP during post-neonatal phase in response to dietary Ova (see e.g., FIG. 10C and FIG. 12). In addition, CD11c+ APCs were found near the colonic epithelium during the post-neonatal phase when GAPs were present. At this specific time in life, these cells were enriched for retinaldehyde dehydrogenase (ALDH) activity (see e.g., FIG. 11C-FIG. 11F), which catalyzes the production of all-trans retinoic acid (ATRA), which in turn supports iTreg generation. Further, naïve CD4+ T-cells specific for dietary or commensal antigens adoptively transferred in the post-neonatal phase when colonic GAPs were present in early life, localized to the colon and became Tregs in response to luminal antigen (see e.g., FIG. 10D-FIG. 3F, FIG. 6E, and FIG. 12A-FIG. 12D), demonstrating an enhanced capacity for antigen specific iTreg accumulation in the colon at this specific time in early life.

The effect of early life alterations of colonic GAPs on the colonic iTreg population was examined. Mice in which colonic GAPs were relatively unaltered, synchronously CF mice, and mice receiving EGFRi in the post-neonatal phase, DOL 14 and 16 when colonic GAPs are present, each had a pattern and timing of colonic LP Treg populations that resembled the endogenous Treg population of non-manipulated animals (compare FIG. 10A with FIG. 10F and FIG. 10G). Mice in which colonic GAPs were opened prematurely, neonatal phase DOL 1 pups CF to dams 10 days pp, and mice receiving EGFRi in the neonatal phase, DOL 6 and 8, each had early peaks in colonic LP Tregs; these peaks rapidly decreased and were not maintained (see e.g., FIG. 10F, FIG. 10G). Mice in which colonic GAPs were inhibited during post-neonatal phase, DOL 10 pups CF to dams that had just delivered, and mice with colonic GAPs opened inappropriately beyond weaning by EGFRi on DOL 24 and 26, rapidly lost the colonic Treg population (see e.g., FIG. 10F, FIG. 10G). The diminished iTreg population (see e.g., FIG. 10H) persisted for at least 8 months, and affected the RORγt+ iTregs (see e.g., FIG. 10I-FIG. 10L), whose development occurs predominantly in the colon and is dependent upon the microbiota, indicating that disrupting these early-life events causes long-lasting defects that are not easily corrected.

Figure 14:
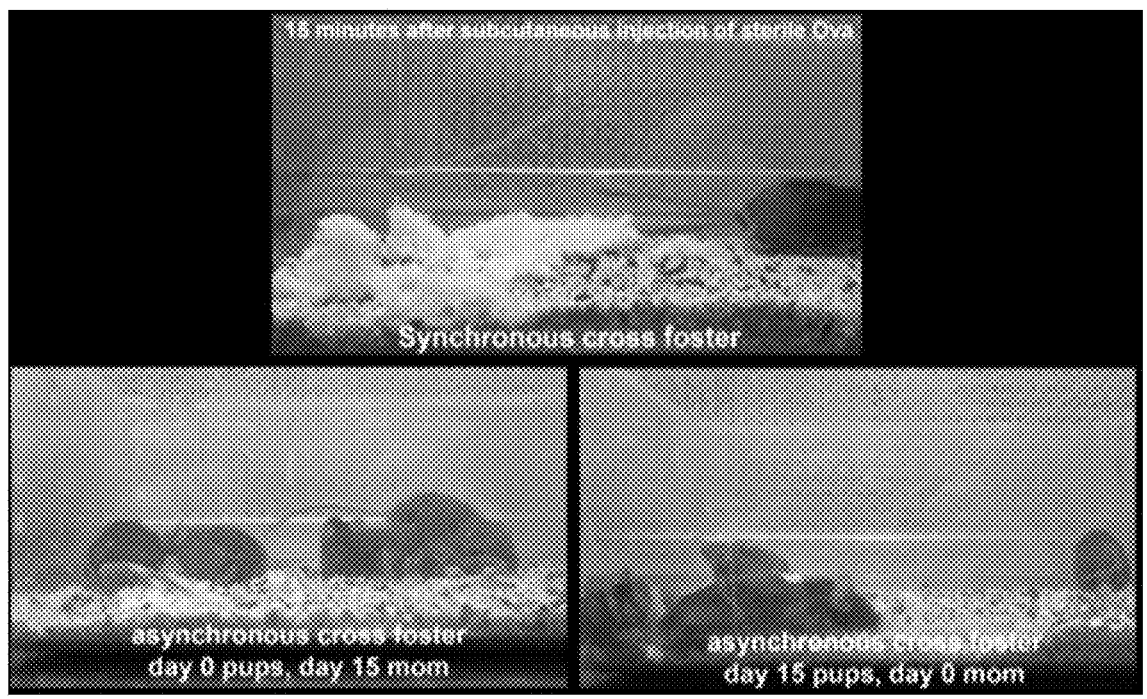
FIG. 14 is a still image of a montage of videos taken 15 minutes after challenge with Ova in the footpad of cross fostered mice that were given Ova in drinking water days 0-30 of life and immunized to Ova as adults.
Figures 15A, 15B, 15C, 15D, 15E, 15F:
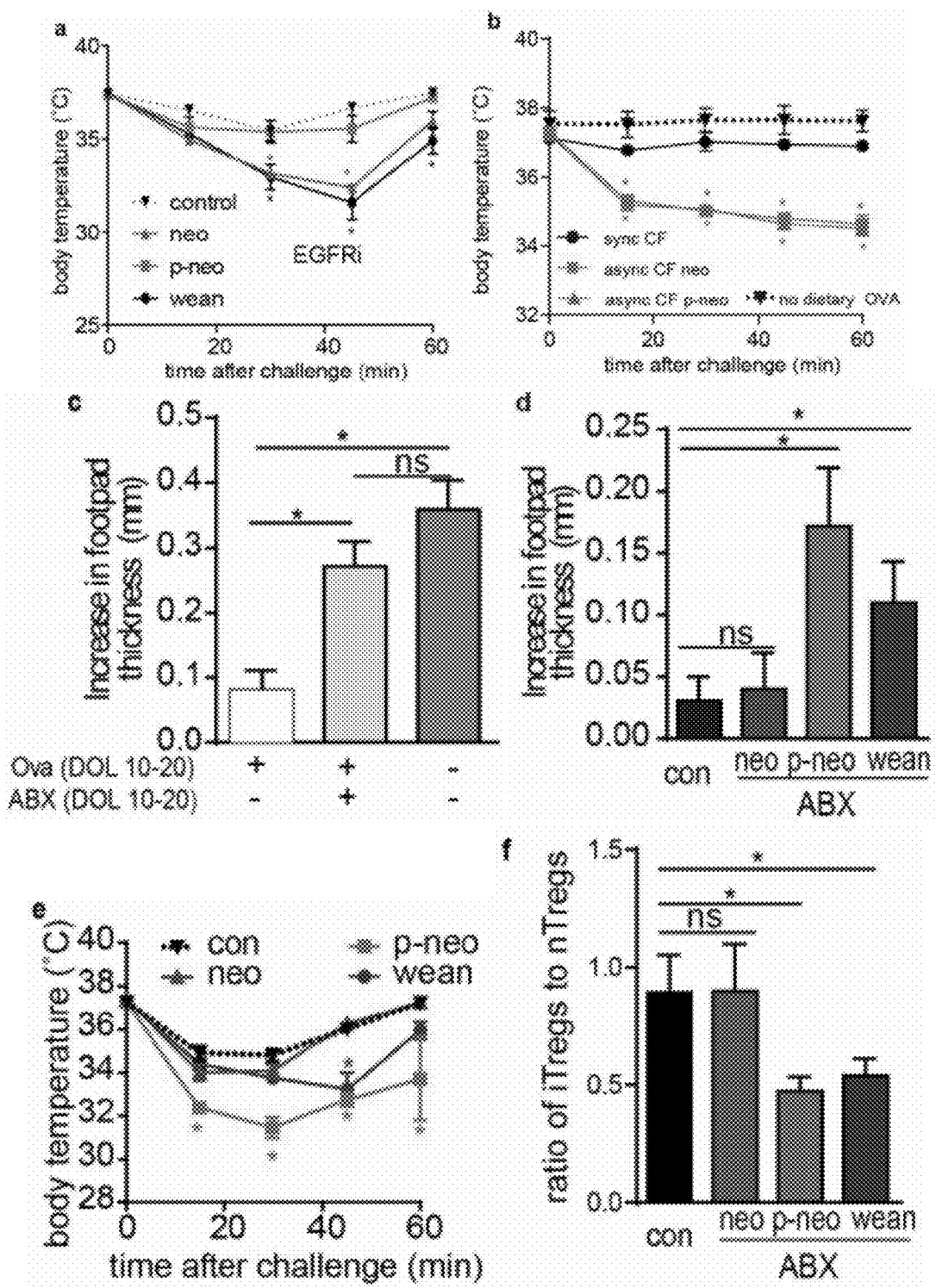
FIG. 15A-FIG. 15F is a series of plots and bar graphs showing effects of altering colonic GAPs in early life or altering the microbiota when colonic GAPs are present on tolerance induction.

The effects of early-life alterations of antigen uptake by colonic LP-APCs on subsequent immune responses were measured. Asynchronously CF mice or mice treated with EGFRi either in the neonatal phase, DOL 6 and 8, or in the weaning phase, DOL 24 and 26, and their respective controls, synchronously CF mice and mice receiving EGFRi in the post-neonatal phase, DOL 14 and 16, were given dietary Ova on DOL 0-30 and assessed for tolerance induction using a DTH assay as adults. Oral tolerance was significantly abrogated, as evidenced by increased footpad swelling upon Ova rechallenge, by each manipulation that changed the normal timing of antigen uptake by colonic LP-APCs (see e.g., FIG. 13A and FIG. 13E). Moreover, mice in which the timing of antigen uptake by colonic LP-APCs was altered, were lethargic and hypothermic when rechallenged with sterile Ova in the footpad, recapitulating anaphylaxis (see e.g., FIG. 14, movie not shown and FIG. 15A-FIG. 15B). These mice had markedly elevated serum levels of Th2 mediators, and global and antigen-specific IgE, but did not have elevations in other immunoglobulins or prototypic Th1 or Th17 cytokines (see e.g., FIG. 13B-FIG. 13D, FIG. 13F-FIG. 13H and FIG. 16A-FIG. 16D). This phenotype persisted for months, indicating that altering antigen uptake by colonic LP-APCs causes a long-term bias toward Th2 responses. FIG. 14 (movie not shown) is a series of stills of a video taken 15 minutes after challenge with Ova in the footpad of cross fostered mice that were given Ova in drinking water days 0-30 of life and immunized to Ova as adults.

Figures 13A, 13O:
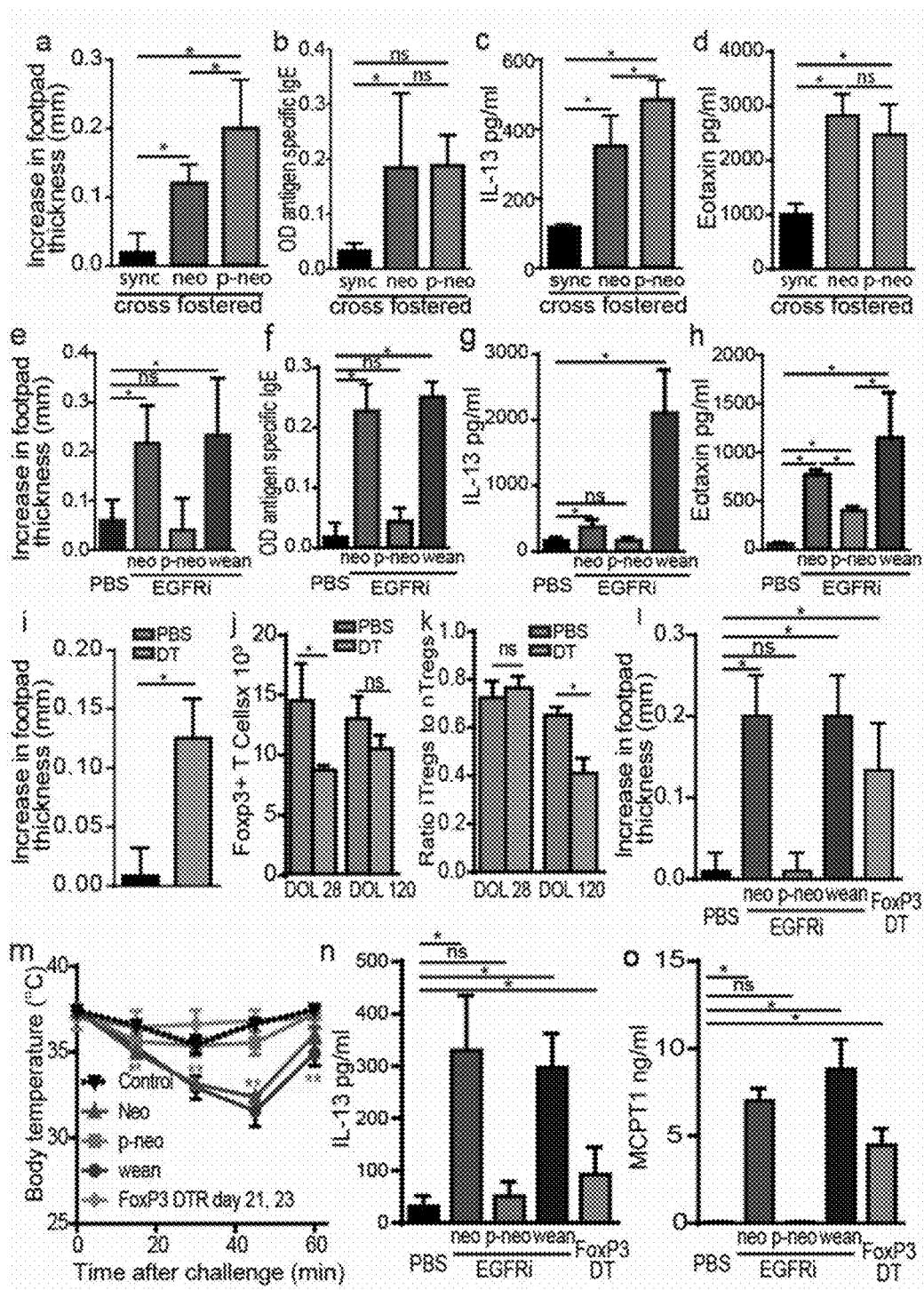
FIG. 13A-FIG. 13O is a series of graphs showing altering the maternal control of the colonic immune system's exposure to luminal substances impairs the ability to induce tolerance and causes long-term skewing of immune responses to a Th2 phenotype.

Non-manipulated mice not receiving dietary Ova do not develop hypothermia, lethargy, or skewed Th2 cytokine production following Ova rechallenge in the DTH assay (see e.g., FIG. 15B and FIG. 16C), despite sustaining increased footpad swelling (compare FIG. 1A and FIG. 13A and FIG. 13E). Therefore anaphylaxis and Th2 skewing following manipulation of colonic GAPs and antigen uptake in early life were not solely attributable to the absence of uptake and tolerance induction to the specific antigen (Ova) used in the DTH, but might also be attributed to alterations in the exposure/uptake of other luminal substances, such as gut microbes and their products, during this interval. Alterations in these exposures could change the colonic iTreg population, and may not easily be corrected in later life. In support of this, deletion of the Treg population at DOL 23 abrogated tolerance to dietary Ova given from 0-30 DOL and resulted in persistent deficits in the iTreg, but not the natural Treg (nTreg), population (see e.g., FIG. 13I-FIG. 13K). The bloom of gut *Clostridia* that can induce Tregs coincides with the interval when colonic GAPs are normally open and antigens are acquired by colonic immune cells (see e.g., FIG. 6 compare with FIG. 1C and FIG. 1I). Indeed, oral antibiotics given during the post-neonatal phase in which antigen is normally delivered to the colon were particularly effective at abrogating oral tolerance, inducing hypothermia upon Ova rechallenge, and producing a sustained reduction in the iTreg population (see e.g., FIG. 15C-FIG. 15F). Moreover, altering the normal window of antigen uptake by the colonic immune system in early life, or deleting the Tregs that developed after this interval in early life, abrogated the ability to induce tolerance to dietary antigens encountered for the first time in adulthood (see e.g., FIG. 13I). Mice in which colonic antigen uptake was altered had Th2 skewing of immune responses and developed lethargy and hypothermia upon rechallenge with antigens initially encountered in adulthood (see e.g., FIG. 13M-FIG. 13O), thus demonstrating the importance of these events and their timing for mounting balanced immune responses to antigens encountered throughout life.

These observations give insight into recent studies identifying the benefit of breastfeeding, with the complimentary introduction of dietary allergens and exposure to gut microbes prior to weaning, but not later, for reducing allergy in at-risk individuals. These time-limited benefits are directly linked to maternal control, via breast milk, of the temporal and regional pattern of luminal antigen uptake in early life. The iTregs induced to solid foods after weaning, a time in which antigen is predominantly delivered to the SI immune system, are short lived, continuously generated in the SI, and recede when food antigens are removed. In comparison the RORγt+ iTregs generated when breast milk shunts antigen to the colonic immune system in the post-neonatal phase prior to weaning are long-lived, generated during a specific period of time in the colon, and have capacities to control Th2 responses. Hence, introducing a food allergen during this specific time during breastfeeding generates long-lived antigen specific Tregs, thereby conferring a sustained and enhanced tolerance to a dietary allergen, and may tip the balance away from a food allergy phenotype in at-risk children. Moreover the development of these RORγt+ iTregs generated during this specific time prior to weaning is dependent upon the microbiota and they may be directed at dietary or microbial antigens. This dependence and the inability to restore the RORγt+ iTreg population later in life, if not properly established, explains why antibiotic therapy during this specific period prior to weaning increases the risk of allergy and why exposure to the microbiota before, but not after, weaning, reduces allergies. Historically, delayed introduction of food allergens may have occurred because of seasonal and regional variation in the availability of food. These observations support that while delayed food allergen introduction does not reduce, and may, in fact, increase food allergy in at-risk children, maneuvers altering the gut microbiota or the maternal signals promoting the generation of stable population of colonic iTregs have even greater consequences, causing a long-term iTreg deficit and predisposing to Th2 responses to antigens encountered later in life. Hence, the short-term benefit of antibiotics in infancy should be weighed against the longer-term risk of allergies. Additionally, these data raise concern about the use of feeds with formula or donor milk. In concert with delayed food allergen introduction, these practices may explain the dramatic increase in allergic diseases in many populations worldwide.

Materials and Methods

Mice: All mice were maintained on the C57BL/6 background. C57BL/6 mice, B6SJL mice, OTI T-cell receptor transgenic mice, OTII T-cell receptor transgenic mice, and CD11c$^{YFP}$ transgenic mice, Math1$^{fl/fl}$ mice, FoxP3$^{GFP-DTR}$ transgenic mice, were purchased from The Jackson Laboratory (Bar Harbor, Me.) or The National Cancer Institute (Frederick, MD), and bred and maintained in-house. Myd88$^{-/-}$ mice, a gift from Dr. Akira (Osaka University, Osaka, Japan), were bred onto the C57BL/6 background by the Speed Congenics Facility of the Rheumatic Diseases Core Center, and maintained in-house. CBir1 TCR transgenic mice on the B6SJL background (CD45.1) were generated as described. FoxP3$^{DTR/GFP}$ mice were injected with 50 µg/kg diphtheria toxin (Sigma Aldrich) i.p. on DOL 21 and 23 of life to deplete FoxP3 cells arising during the post-neonatal phase. Transgenic mice in which a tamoxifen-dependent Cre recombinase is expressed under the control of the villin promoter (vil-Cre-ERT2) mice were a gift from Sylvie Robine (Institut Curie, Paris, France). Math1$^{fl/fl}$ mice were bred to vil-Cre-ERT2 mice to generate mice with inducible depletion of GCs following deletion of Math1 in villin expressing cells, referred to as Math1$^{iΔvil}$ mice. To deplete GCs, Math1$^{iΔvil}$ mice were injected with 25 µg tamoxifen (Sigma-Aldrich, St. Louis, Mo., USA) dissolved in sunflower seed oil with 20% ethanol (Sigma-Aldrich) i.p. daily for 4 days starting at DOL 6. Germ free mice were obtained from the Washington University Digestive Disease Research Core Center murine models core. Adult mice, neonatal phase mice, post-neonatal phase mice, and weaned mice were 8 to 16 weeks of age, 8 days of age, 18 days of age, or 28 days of age respectively when analyzed if not otherwise stated. Mice were weaned at DOL 21 with the exception of mice in FIG. 8B, which were weaned at DOL 25. Animals other than germ-free mice were housed in a specific-pathogen-free facility and fed routine chow diet. Offspring of both sexes were used in this study. Group size was based upon the size of the litter, which was 4 or greater unless noted otherwise. The number of replicates for each experiment is noted in the figure legend. For EGFRi treatment experiments and oral Ova timing experiments animals were assigned to treatment groups based upon litter size to give equivalent numbers of offspring in each group. In CF experiments animals were assigned treatment groups based upon the day of birth and availability of dams for CF. In other experiments littermates were arbitrarily assigned treatment groups, no specific randomization method was used. The investigator was not blinded to group allocation. No animals were excluded from the analysis. Where feasible within the limits of the experimental design, groups of mice used in these studies were littermates and co-housed throughout the experiment to minimize differences in the microbiota. Animal procedures and protocols were performed in accordance with the IACUC at Washington University School of Medicine.

Antibiotic treatment: Mice were given a combination of antibiotics (Abx) ampicillin (1 g/L), metronidazole (1 g/L), neomycin (1 g/L), and vancomycin (500 mg/L) in drinking water for the time periods outlined in the figure legends.

Cross Fostering (CF): Asynchronously CF mice were obtained by placing DOL 1 mice with mothers having delivered a litter 10-15 days previous (neonate CF), and DOL 10-15 mice with mothers having delivered a litter one day previous (post-neonate CF). Mice were synchronously CF by placing DOL 1 mice with different mothers having delivered the same day. Specific DOL and day pp are stated in the text or figure legends. At time of CF the mother's nose and pups were swabbed with vanilla to prevent pup rejection.

EGFRi treatment: Mice were injected with 500 µg/kg tyrphostin AG1478 (an inhibitor of EGFR phosphorylation) in the neonatal, post-neonatal, or weaned phase on DOLs noted in the text or figure legends.

Oral tolerance and Delayed Type Hypersensitivity Responses: Mice, and/or nursing dams, when treated prior to weaning, were given Ova 20 g/L in drinking water, or drinking water alone for the intervals defined in the figure legend. Four weeks and six weeks following dietary Ova exposure mice were immunized subcutaneously with 100 µg Ova in incomplete Freund's Adjuvant (Sigma Aldrich). Two weeks after the last immunization mice were challenged with 20 µg Ova in the footpad, body temperature monitored for one hour, and the increase in footpad thickness evaluated using measurements taken with micrometer calipers taken before and 24 hours after challenge. To directly evaluate colonic antigen delivery and blockade of GAPs in the development of tolerance, enemas containing Ova 10 µg/gm body weight with or without 10 µg EGF were administered intrarectally every other day five times from DOL 14 to 22 (post-neonatal phase) or DOL 56 to 64 (adult). Mice were rested three weeks, and then systemically immunized and challenged in the footpad as above.

Isolation of cellular populations and flow cytometry: SIs or colons were harvested, rinsed with PBS, and Peyer's patches or colonic patches were removed. Epithelial cellular populations were released by incubating for 15 min three times in a 37° C. rotating incubator in HBSS media (Bio-Whittaker, Walkersville, Md.) containing 5 mM EDTA, and splenic and LP cellular populations were isolated as described. Antibodies used are listed in TABLE 1. SI and colonic APCs were identified as 7AAD$^-$, CD45$^+$, CD11c$^+$, MHCII$^+$ for flow cytometric sorting. FoxP3 subpopulations were identified as 7AAD$^-$, CD45$^+$, CD3$^+$, CD4$^+$, FoxP3$^+$, and either RORγt$^+$ or Helios$^+$. For intracellular antigens and cytokines, cells were fixed, permeabilized overnight, and stained per the manufacturers recommendations (eBioscience). Flow cytometry was performed with a FACScan cytometer (BD Biosciences, San Jose, Calif.) retrofitted with additional lasers. Data acquisition was performed using CellQuest (BD Biosciences) and Rainbow (Cytek, Fremont, Calif.) or FlowJo software (Tree Star, Ashland, Oreg.). Data analysis was performed on a Macintosh computer running FlowJo software.

TABLE 1

Antibodies/staining reagents used

| Antibody | Clone | Vendor |
|---|---|---|
| Cytokeratin-18 | C-04 | Abcam |
| Muc2 | | Abcam |
| Phospho-p44/p42 MAPK (Thr202/Tyr204) | | Cell Signaling Technologies |
| Phospho-EGFR (Tyr1173) | | Millipore |
| CD45 | 30-F11 | Ebioscience |
| CD45.2 | 104 | Ebioscience |
| CD11c | N418 | Ebioscience |
| MHCII | NIMR-4 | Ebioscience |
| CD103 | M290 | BD Pharmigen |
| CD24 | 30-F1 | Ebioscience |
| CD3 | 17A2 | Ebioscience |
| CD4 | L3T4 | Ebioscience |
| CD8 | 53-6.7 | Ebioscience |
| F4/80 | BM8 | Ebioscience |
| CD11b | M1/70 | Ebioscience |
| FoxP3 | FJK-16s | Ebioscience |
| IL10 | JES5-16E3 | Ebioscience |
| IL17 | Ebio17B7B2D | Ebioscience |
| RORγT | 2F11-C3 | Ebioscience |
| GP2 | | MBL |
| DAPI | | Invitrogen |
| 7AAD | | Sigma-Aldrich |

TABLE 2

Primers used for RTPCR analysis (see SED ID NO: 1-SEQ ID NO: 32).

| Target | Forward | Reverse |
|---|---|---|
| TLR 1 | caggtctccgagagggtactg | gctacggatgagccaaatgaag |
| TLR 2 | gagcgagctgggtaaagtagaaa | agccgaggcaagaacaaaga |
| TLR 3 | gtgagatacaacgtagctgactg | tcctgcatccaagatagcaagt |
| TLR 4 | atggcatggcttacaccacc | gaggccaattttgtctccaca |
| TLR 5 | cggcctctgttgggatgtt | gaccgcatggcttcctcttc |
| TLR 6 | tgagccaagacagaaaaccca | gggacatgagtaaggttcctgtt |
| TLR 7 | ggtaagggtaagattggtggtg | cgtcacaaggatagcttctggaa |
| TLR 8 | gaaaacatgcccctcagtca | cgtcacaaggatagcttctggaa |
| Myd88 | tgccgtcctgtctacatctttg | gttgctcaggccagtcatca |
| EGFR | tcttcaaggatgtgaagtgtg | tgtacgctttcgaacaatgt |
| 16S (8F-355R) | agagtttgatcatggctcag | actcctacgggaggcagc |
| MUC2 | ccaccccctatgggtgccca | gcatgggtggggatcgcac |
| Relmβ | cactgatagtcccagggaacgcgc | atccacagccatagccacaagcac |
| Math1 | atgcacgggctgaacca | tcgttgttgaaggacgggata |
| Cytokeratin 18 | tccagaccgagaaagagacca | cccggattttgctctccagt |
| CBir1 antigen | gctgacacaggaaatcgatcg | gagagtatacatcacccgtcgcat |

OTII T-cell co-culture: 3.5×10⁴ flow cytometrically sorted splenic CD3⁺CD4⁺Vα2⁺Vβ5⁺ OTII T-cells were cultured in the presence of 10 μg Ova and 3.5×10⁴ LP cells isolated from the SI or colon or MLN cells isolated from DOL 18 mice. Seven days later cells were analyzed by flow cytometry.

Analysis of luminal antigen delivery to LP-DCs: Mice received Ova 20 g/L (Sigma Aldrich) for 3 days prior to isolation of LP-APCs (dietary Ova FIG. 1C) or were anesthetized and 2 mg Ova (OTI assay) or 25 mg Ova (OTII assay) dissolved in phosphate buffered saline (PBS), or PBS alone (controls), was injected intraluminally into the SI or colon as previously described. Two hours later cell populations were isolated from the non-Peyer's patch bearing SI LP or non-colonic patch bearing colon LP. APC populations and Ova specific CD4+ OTI or CD8+ OTII T-cells were isolated with flow cytometric cell sorting and cultured at a ratio of 1:10 APCs (1×10⁴) to T-cells (1×10⁵). As a positive control, 10 μg Ova was added to cultures of APC populations isolated from mice receiving luminal PBS. After 3 days, cultures were evaluated for the number of T-cells by flow cytometry and cell counting.

Immunohistochemistry: Immunohistochemistry was performed as described using antibodies listed in Table 1. Pseudo-colored black and white images from fluorescent microscopy were obtained with an axioskop 2 microscope using Axiovision software (Carl Zeiss, Thornwood, N.Y.).

Adoptive T-cell Transfers: Nursing B6SJL females with pups at DOL 7 or B6SJL females at DOL 49 were given Ova 20 g/L in drinking water and 7 days later, at DOL 14 (post-neonatal) or DOL 56 (adult), mice were injected i.p. with 10⁶ OTI (CD45.2) or 10⁶ DTII (CD45.2) naïve Ova-specific T-cells. Seven days later, organs were harvested for immunofluorescence or cell isolation and analyzed by flow cytometry to detect CD45.2⁺ OTI or OTII T-cells. Naive CD8 or CD4 T-cells isolated from the spleen of C57BL/6 mice (CD45.2) served as antigen non-specific controls. In some experiments, cells were labeled with CFSE prior to injection to identify cells in tissue sections. 10⁶ splenic CD4⁺ T-cells from a CBir1 B6SJL transgenic mouse were enriched by magnetic particles (Stemcell Technology, #19752 Vancouver, British Columbia, Canada) and injected into mice at DOL 21 (post-neonatal) or at DOL 56 (adults) as outlined in FIG. 11, and analyzed seven days later by flow cytometry.

Intravital two-photon (2P) microscopy: Mice were anesthetized using nebulized isofluorane in 95% $O_2$/5% $CO_2$. Intravital preparation of the intestine was performed as previously described. To detect GAPs, lysine fixable fluorescently-labeled dextran 10,000 MW (10 mg/mL) and diamidino-2-phenylindole (DAPI; 10 mg/mL) were injected intraluminally 20 minutes prior to imaging, and imaging was performed for up to one hour. To detect paracellular leak fluorescently labeled dextran 3,000 MW (10 mg/mL) and DAPI (10 mg/mL) were injected intraluminally 20 minutes prior to imaging. To detect the extension of trans-epithelial dendrites by APCs, CD11c$^{YFP}$ or CX3CR1$^{GFP}$ were imaged as above using 10,000 MW fluorescent dextran to outline the epithelial surface. Tissues were excited using a Ti:sapphire laser tuned to 890 nm (Chameleon X R, Coherent). Time-lapse imaging was performed with a custom-built 2P microscope running ImageWarp acquisition software (A&B Software, New London, Conn.). Epithelial integrity was assessed by dextran and DAPI staining as described. Following imaging, tissues were placed in 10% formalin buffered phosphate solution (Fisher Scientific) to fix dextrans in place to confirm 2P findings and for further analysis by immunofluorescence microscopy.

In some experiments mice were treated with 150 μg/kg carbachol chloride i.p. 10 minutes before dextran, 100 mg/kg tropicamide (mAChR4 selective antagonist) i.p. 20 minutes before dextran, 500 μg/kg tyrphostin AG1478 (inhibitor of EGFR phosphorylation) i.p. 20 minutes before dextran, 10 mg/kg U-0126 (inhibitor of p42/p44 MAPK phosphorylation) i.p. 20 minutes before dextran, 1-1000 ng EGF (Shenandoah Biotechnologies) injected intraluminally 20 minutes before dextran, 10 μg LPS injected intraluminally 20 minutes before dextran, or 100 μl stomach contents from a DOL 10 mice, or 100 μl heat killed cecal contents from SPF housed adult mice injected intraluminally 20 minutes before dextran was administered. All reagents from Sigma Aldrich, St. Louis, Mo. unless otherwise noted.

Enumeration of GAPs: GAPs were identified as dextran-filled columns measuring approximately 20 μm (height)×5 μm (diameter) traversing the epithelium and containing a nucleus. GAPs were enumerated in the jejunum or mid-transverse colon using Z-stack images of a volume of 225 μm(x) by 250 μm(y) by 50 μm(z) acquired during in vivo 2P imaging as described above. SI GAPs were enumerated as GAPs per villus. When present, colonic GAPs were found on both the surface epithelium and within the crypts, but were enumerated as GAPs per crypt due to difficulty in distinguishing dextran filled GAPs from luminal dextran during in vivo imaging. De-identified and coded video clips were evaluated by a blinded investigator to enumerate GAPS in early life. The number of GAPs per villus and GAPs per crypt seen by 2P imaging were confirmed by immunofluorescence microscopy of tissues that were fixed following 2P imaging. To quantify GAPs per GC, lysine fixable 10,000 MW fluorescent dextran was injected into the lumen and intestines harvested 25 min later. Tissues were fixed with 10% formalin buffered saline for 45 min, sectioned, and stained with antibodies directed against cyt18. GCs were identified cyt18+ epithelial cells with GC morphology and GAPs as dextran containing epithelial cells defined as above.

Bacterial DNA extraction, 16s rDNA Quantification, and sequencing: Cecal contents were placed in 750 ul lysis buffer (200 mM NaCl, 100 mM Tris, 20 mM ETA, pH 8.0) with 200 mg 0.1 mm diameter zirconium silica beads (BioSpec, Bartlesville, Okla.), and vortexed on a bead beater (MP Biomedicals, Fast prep 24). DNA was isolated using the All prep DNA/RNA extraction kit (cat #80204, Qiagen, Valencia, Calif.). Quantification of the copies of 16s rDNA was performed using real time PCR and a standard curve, using the primer set to measure total bacteria, 5'-GGT-GAATACGTTCCCGG-3' (SEQ ID NO: 33) and 5'-TACGGCTACCTTGTTACGACTT-3' (SEQ ID NO: 34). Metagenomic analysis of the bacterial communities was performed using the 16S rDNA gene V4 variable region PCR primers 515/806 with barcode on the forward primer in a 30 cycle PCR with HotStarTaq Plus Kit (Qiagen) with the following conditions: 94° C. for 3 minutes, followed by 28 cycles of 94° C. for 30 seconds, 53° C. for 40 seconds and 72° C. for 1 minute, with final elongation step at 72° C. for 5 minutes. Amplification success was evaluated with a 2% agarose. Samples were pooled in equal proportions based on their molecular weight and DNA concentrations and purified with Ampure XP beads (Beckman Coulter, Brea Calif.). The PCR products were then used to prepare DNA library using the Illumina TruSeq DNA library preparation protocol. Sequencing was performed at MR DNA (www.mrdnalab.com, Shallowater, Tex., USA) on a MiSeq (Illumina, San Diego, Calif.). Sequence data were processed using a proprietary analysis pipeline (MR DNA, Shallowater, Tex., USA). Sequences were depleted of barcodes, after which reads <150 bp and those with ambiguous base calls were removed. Reads were denoised, OTUs generated, and chimeras removed. Operational taxonomic units (OTUs) were defined by clustering at 3% divergence (97% similarity). Final OTUs were taxonomically classified using BLASTn against a curated GreenGenes database.

Measurement of cytokines, EGF, and immunoglobulins: Cytokines were measured using the MILLIPLEX MAP Mouse Cytokine/Chemokine Magnetic Bead Panel (see e.g., FIG. 16D; EMD Millipore) or using ELISAs for EGF (R&D systems), IL13 (eBioscience), Eotaxin (R&D systems), IgE (eBiosciences), and MCPT1 (eBioscience) per the manufacturers recommendations. An ELISA comprised of Ova (Sigma-Aldrich A5503) for capture, and monoclonal anti-IgE antibody conjugated to alkaline phosphatase (Southern Biotech 1110-04) for detection, was used to measure Ova specific IgE. An ELISA comprised of monoclonal anti-IgG (Southern Biotech 1030-01) and monoclonal anti-IgG conjugated to alkaline phosphatase (Southern Biotech 1030-04) for detection and purified mouse $IgG_1$ standard (Southern Biotech 0102-01) was used to measure total IgG.

Quantitative real time polymerase chain reaction (PCR) assay: GCs, identified as $7AAD^-$ $CD45^-$ $CD24^-$ Cytokeratin$18^+$ UEA-$I^+$ and IECs identified as $7AAD^-$ $CD45^-$ $CD24^-$ Cytokeratin $18^-$ UEA-$I^-$ were sorted from the epithelial fraction of intestines at DOL 18 directly into RLT buffer (Qiagen). RNA was extracted from epithelial cellular populations, treated with DNAse, and transcribed into cDNA using Superscript II reverse transcriptase (Invitrogen, Carlsbad, CA) according to the manufacturer's recommendations. Primers used for RT-PCR are listed in Table 2. The absolute copy number of the target was calculated from standards that were constructed as previously described.

Stool EGF levels: Pre-existing stool specimens prospectively collected from a cohort of healthy children were used for this study. Consent was obtained from mothers to collect stools from their children, under approval from the Washington University Human Research Protection Office. Data were collected regarding pregnancy, labor, delivery, medications, and feeding by interviewing parents and/or reviewing medical records as previously reported. Specimens used for in this study were from healthy children delivered at >35 weeks gestation who were not on continuous medication through the first year of life. Stool specimens were stored at −80° C. until analyzed. Specimens were disrupted using a Bullet Blender Tissue Homogenizer (Next Advance) after adding 500 µL of buffer RLT (Qiagen) with 1 mg of 0.1 mm zirconium oxide beads. Protein was isolated from lysates using an AllPrep DNA/RNA/protein minikit per manufacturer's recommendations (Qiagen) and dissolved in PBS and EGF measure by ELISA (R and D systems).

Statistical Analysis: Data analysis using a two sided student's t test for studies involving two groups or one way ANOVA with a Dunnett's or Tukey's posttest with correction for multiple comparisons for studies involving 3 or more groups was performed using GraphPad Prism (GraphPad Software Inc., San Diego, Calif.). Data is assumed to be normally distributed. A cut off of $p<0.05$ was used for significance.

Example 2

Neonatal Sepsis

Neonatal sepsis, a bloodstream infection and a leading cause of death in newly born babies accounting for 26% of all neonatal deaths, is divided into early-onset sepsis (EOS) and late-onset sepsis (LOS). EOS is caused by transplacental or ascending infections from the maternal genital tract, while the organisms causative of LOS are acquired after delivery. Patients most at risk of LOS are those born with very low birth weight, and often placed in intensive care units without access to breast milk. In a substantial portion of LOS, the pathogen can be found as a resident of the neonatal gut microbial community prior to disease. Currently it is hypothesized that an immature gut barrier is to blame for the translocation of resident gut bacteria resulting in LOS, yet the mechanisms allowing or inhibiting translocation of the gut microbiota in early life have remained enigmatic.

Figure 17:
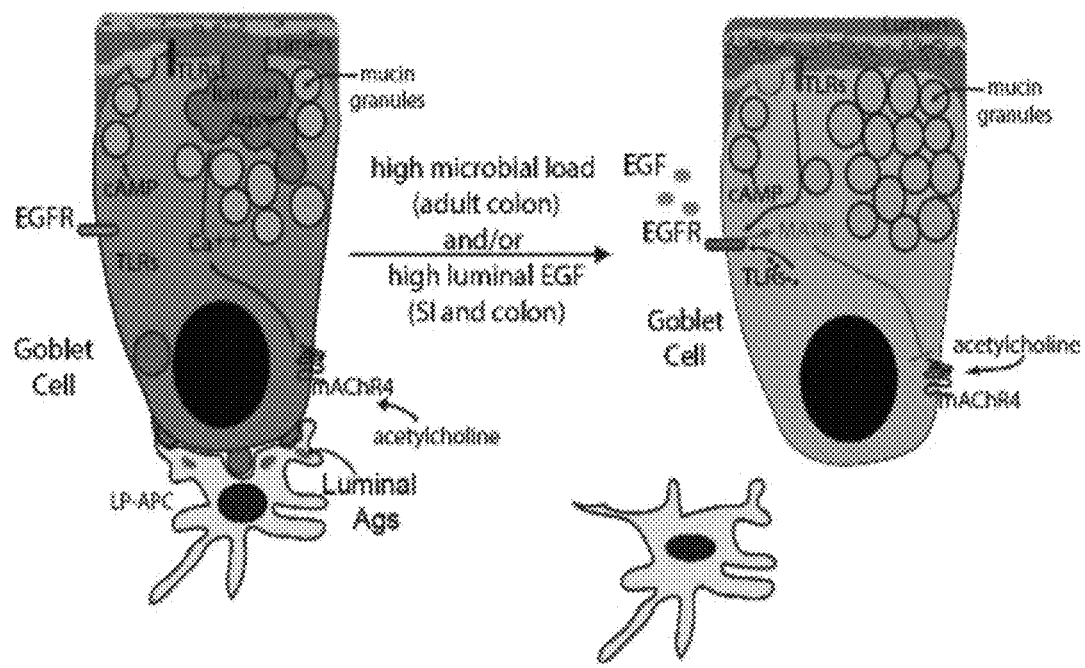
FIG. 17 is an illustration showing Goblet-cell-associated antigen passages (GAPs).

Goblet-cell-associated antigen passages (GAPs) (see e.g., FIG. 17) are a newly defined mechanism of transport from the intestinal lumen across the epithelial barrier. Upon acetylcholine stimulation, goblet cells secrete multiple mucin vesicles, and fill with soluble lumenal antigen. While this regularly occurs in the small intestine, the complex microbiota in the adult colon inhibits acetylcholine signaling via toll like receptors (TLRs) on the goblet cells. Additionally, lumenal epidermal growth factor (EGF) inhibits acetylcholine signaling and GAP formation.

Figure 18:
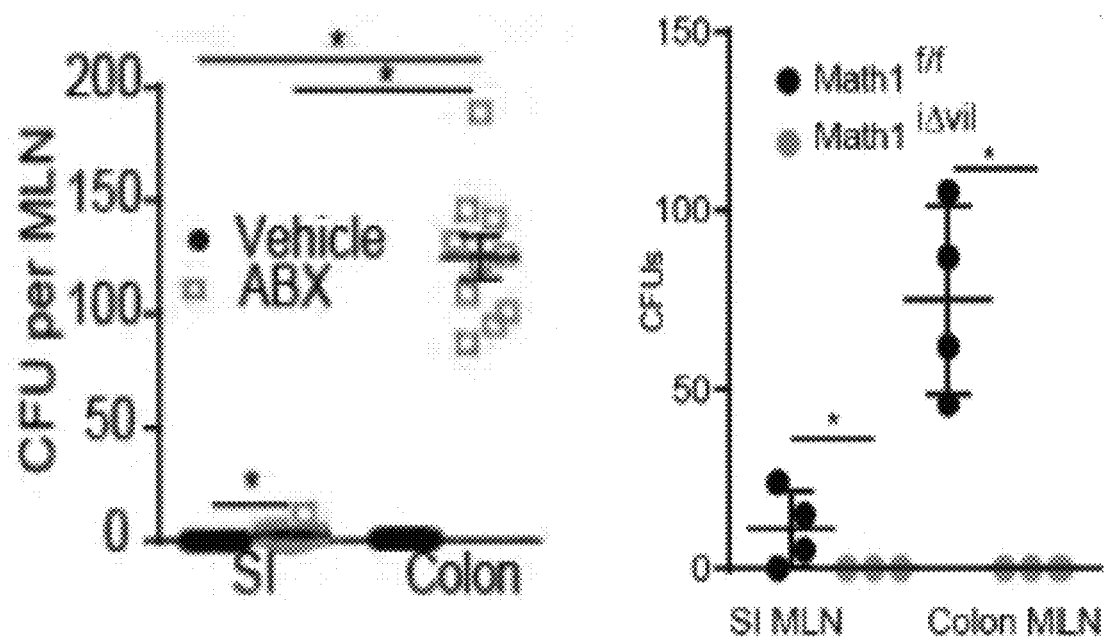
FIG. 18 is a series of line and whisker plots depicting translocation of bacteria across GAPs.
Figure 19:
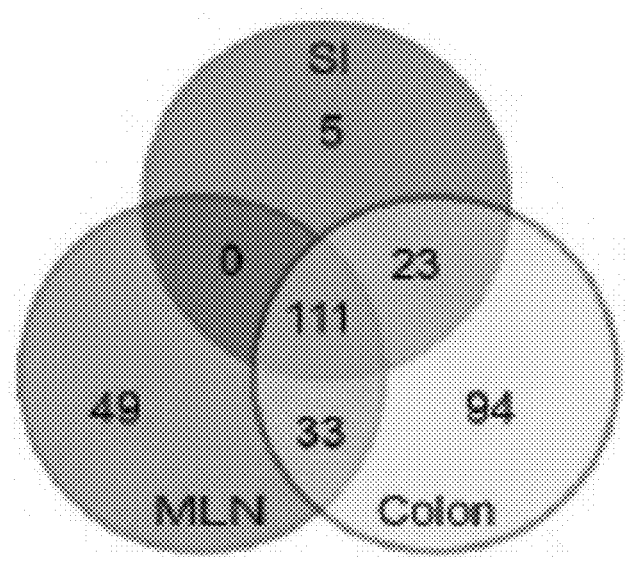
FIG. 19 is a Venn diagram showing the bacteria present in the MLN were most similar to the bacteria present in the colon, suggesting a colonic origin.
Figure 20:
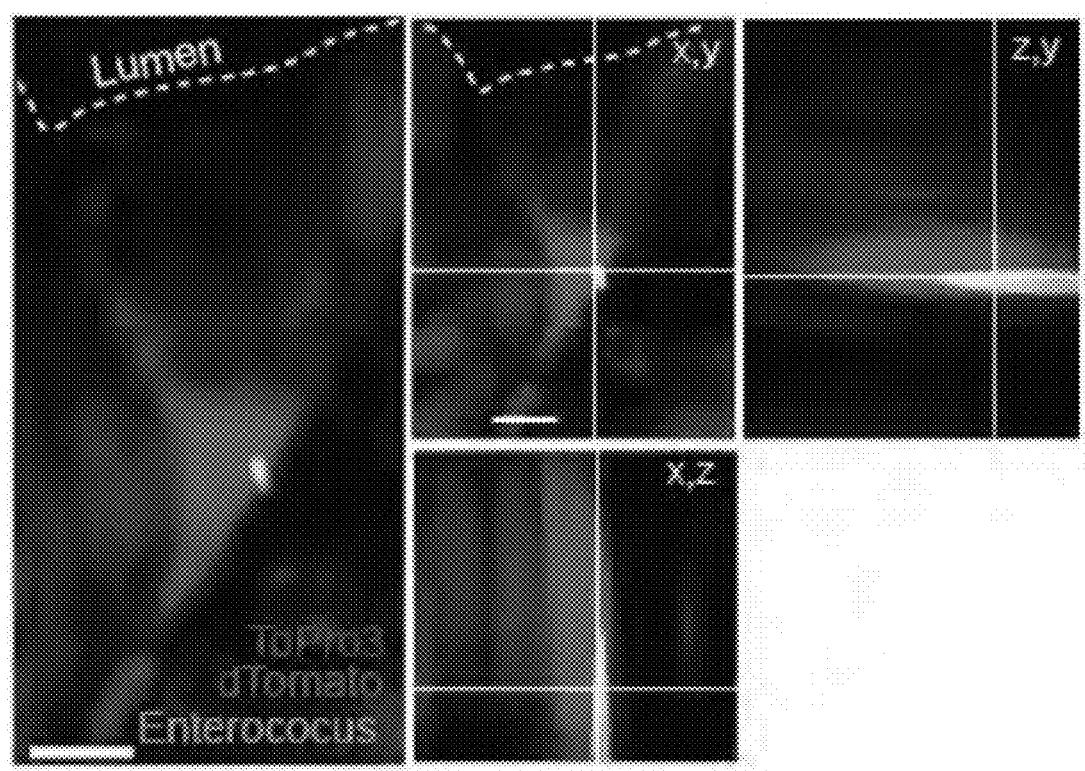
FIG. 20 is a series of images showing when colonic GAPs are present, gut resident bacteria are able to translocate across the epithelial barrier via GAPs. After disruption of the gut microbiota with antibiotics, colonic GAPs form spontaneously (red). Labeled *Enterococcus facaelis* (green) present in the colon lumen were found internalized by the GAPs on confocal microscopy.

Translocation of bacteria across GAPs was observed (see e.g., FIG. 18, FIG. 19, and FIG. 20). After disruption of the gut microbiota with antibiotics, commensal bacteria can be found in the colon draining mesenteric lymph node (see e.g., FIG. 18, left). This process is dependent on goblet cells, as bacteria is not found in mice after inducible deletion of goblet cells (see e.g., FIG. 18, right).

16s sequencing of the colonic draining MLN, and lumenal contents from the small intestine (SI) or colon of antibiotic treated mice revealed the bacteria present in the MLN were most similar to the bacteria present in the colon, suggesting a colonic origin (see e.g., FIG. 19).

After disruption of the gut microbiota with antibiotics, colonic GAPs form spontaneously (see e.g., FIG. 20, red). Labeled Enterococcus facaelis (see e.g., FIG. 20, green) present in the colon lumen were found internalized by the GAPs on confocal microscopy. Thus, when colonic GAPs are present, gut resident bacteria are able to translocate across the epithelial barrier via GAPs.

Figure 21:
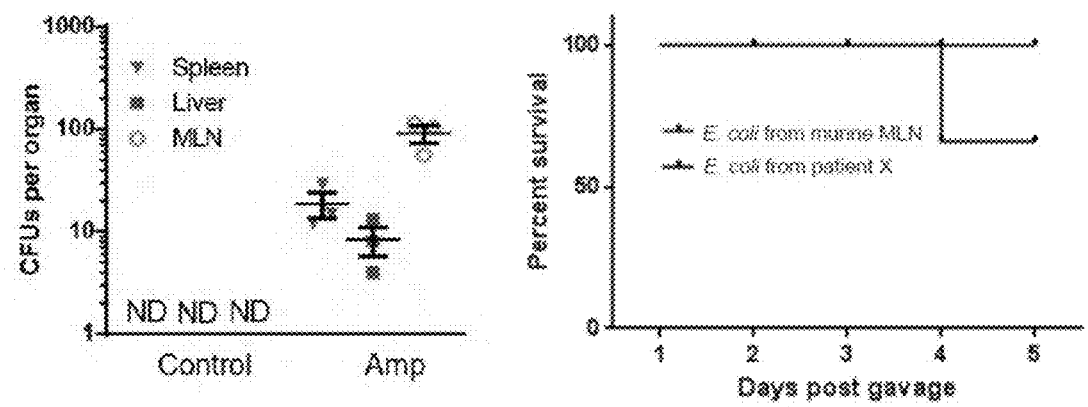
FIG. 21 is a series of plots showing systemic dissemination of bacteria after translocation via GAPs.

Systemic dissemination of bacteria was discovered after translocation via GAPs (see e.g., FIG. 21). After disruption of the gut microbiota with antibiotics, commensal bacteria can be found in the spleen and liver (see e.g., FIG. 21, left). Mice treated with antibiotics were gavaged with mouse gut commensal E. coli or E. coli isolated from a neonatal sepsis patient (see e.g., FIG. 21, right). Only the pathogenic E. coli caused morbidity and mortality in the mice.

Figure 22:
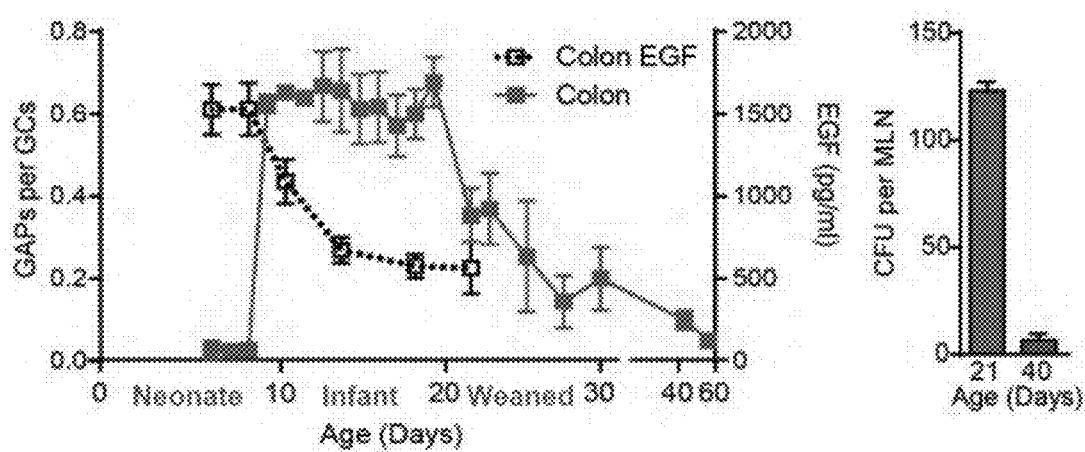
FIG. 22 is a series of plots showing GAP formation in the colon of infant mice.

GAP formation discovered in the colon of infant mice (see e.g., FIG. 22). GAPs are found in the colon of mice between days 10 and 24 of life (see e.g., FIG. 22, left). GAPs are inhibited by: 1) lumenal EGF present in the colon contents, presumably from the maternal breast milk, between days 0 and 10 of life, and 2) the expanding microbiota shortly after weaning (day 24). Commensal bacteria can be found in the colon draining MLN during infancy.

The relationship between neonatal sepsis, bacterial translocation, and GAPs were investigated. It was found that there is a two hit trigger of late-onset sepsis (LOS): (1) presence of pathogenic bacteria in the colon and (2) Formation of Colonic GAPs by either: (a) natural formation of GAPs during infancy or (b) formation of GAPs during neonatal phase due to a lack of inhibitory signals (EGF) from the breast milk.

Example 3

Microbial Antigen Encounter During a Pre-Weaning Interval is Critical for Tolerance to Gut Bacteria The following example describes bacterial antigen encounter in a pre-weaning interval is critical for developing antigen specific tolerance to gut bacteria.

Mammals, including humans, have a mutually beneficial relationship with the trillions of microorganisms inhabiting their gastrointestinal tract. However, maintaining this relationship requires recognizing these organisms as affable and restraining inflammatory responses to these organisms when encountered in hostile settings. How and when the immune system develops tolerance to gut microbial members is not well understood. Here is identified a specific pre-weaning interval in which gut microbial antigens are encountered by the immune system to induce antigen specific tolerance to gut bacteria. Intriguingly for some bacterial taxa, physiologic encounters with the immune system are restricted to this interval, despite abundance of these taxa in the gut lumen at later times outside this interval. Antigen specific tolerance to gut bacteria induced during this pre-weaning interval is stable and maintained even if these taxa are encountered later in life in an inflammatory setting. However, inhibiting microbial antigen encounter during this interval or extending these encounters beyond the normal interval, results in a failure to induce tolerance and robust antigen specific effector responses to gut bacteria upon reencounter in an inflammatory setting. Thus, identified herein, is a defined pre-weaning interval critical for developing tolerance to gut bacteria and maintaining the mutually beneficial relationship with gut microbiota.

The gastrointestinal tract (GI) is home to trillions of microorganisms. The relationship between the host and a healthy gut microbiota is mutually beneficial, with the microorganisms receiving an environment in which to reside and the host receiving benefits related to development, protection from pathogens, immunity, and metabolism. To maintain these mutual benefits, interactions between the host and the gut microbiota are orchestrated to avoid infection yet maintain tolerance and prevent inappropriate inflammatory responses. Indeed, long-lived effector responses to gut commensal antigens can occur when they are encountered in an inflammatory setting. Moreover loss of tolerance to the gut microbiota, as evidenced by systemic immune responses to gut commensals, is believed to underlie the pathogenesis of inflammatory bowel disease (IBD), a chronic inflammatory condition of the GI tract. Damage from inappropriate inflammatory responses is not limited to the host cells, but also induces dysbiosis of the gut microbiota, which has been associated with multiple disorders and in turn promotes host inflammatory responses. Accordingly, how immune tolerance to the microbiota is established, maintained, and becomes altered are central topics to understanding multiple facets of health and disease.

Immune tolerance to environmental antigens is largely mediated by peripheral Foxp3+ regulatory T cells (pTregs). Specific gut commensal bacteria taxa promote the induction of pTregs via bacterial products or metabolites. However, the bacterial antigens to which the majority of colonic pTregs respond originate from gut bacteria taxa that are distinct from those identified to promote pTreg induction. This suggests that tolerance promoting bacterial taxa provide an environment promoting the induction of pTregs directed toward other antigens from other gut bacteria, which may enforce homeostasis and limit inflammatory responses when members of the gut microbiota are re-encountered in other settings. Yet, how and when the process of tolerance induction to the larger community of the gut microbiota occurs is largely unknown.

Initial exposure to microbes via the GI tract early in life has been associated with reduced risk for inflammatory disorders. Observations from multiple studies have suggested the 'hygiene hypothesis', where a decreased susceptibility for immune mediated diseases later in life is associated with early life exposure to microbes and microbial antigens, which are largely encountered in the GI tract. Further, mouse studies have shown that initial exposure to microbes via the GI tract pre-weaning, but not later in life, reduces susceptibility to colitis later in life. These outcomes may be related to encountering microbial antigens in the setting of tolerance promoting gut bacterial taxa, establishing immune tolerance to these antigens and suppressing inflammatory responses upon future encounters. However, the role for tolerance-inducing gut bacteria is not straightforward, as these species are most abundant in later childhood and adulthood, when microbe introduction via the GI tract is less effective at reducing the risk of disease. Thus, there exist additional early life and time-limited aspects to the induction of immune tolerance to the gut microbiota.

Here distinct phases in early life in mice were identified; the neonatal phase, days of life (DOL) 0-10, in which luminal antigens are not encountered by the small intestine (SI) or colonic immune system, the post-neonatal phase, DOL 11-weaning, in which luminal antigens are encountered almost exclusively by the colonic immune system, and the post-weaning phase, in which luminal antigens are encountered almost exclusively by the SI immune system. The inhibition of antigen delivery to the SI and colon in the neonatal phase and to the SI in the post-neonatal phase was mediated by high levels of luminal epidermal growth factor (EGF) acting on the EGFR on goblet cells (GCs) suppressing the formation of goblet cell associated antigen passages (GAPs). This pattern of antigen delivery allowed for the immune system's encounter with gut microbial antigens and the development of pTregs directed toward members of the gut microbiota at this specific and crucial time in early-life. Inhibition of bacterial antigen encounter pre-weaning or shifting the timing of bacterial antigen encounter by the colonic immune system to the post-weaning period abrogated the development of pTregs directed toward members of the gut microbiota and resulted in worse colitis in response to epithelial injury and inflammatory responses to gut commensals later in life. These observations identify a specific period in early life that are critical for the induction of tolerance to the gut microbiota, which once established serves to limit inflammatory responses upon encounter of gut resident bacteria in inflammatory settings.

Luminal Antigen Encounter by the Gut Immune System Occurs in Phases in Early Life.

Figures 23A, 23B, 23C, 23D, 23E, 23F, 23G, 23H, 23I, 23J, 23K:
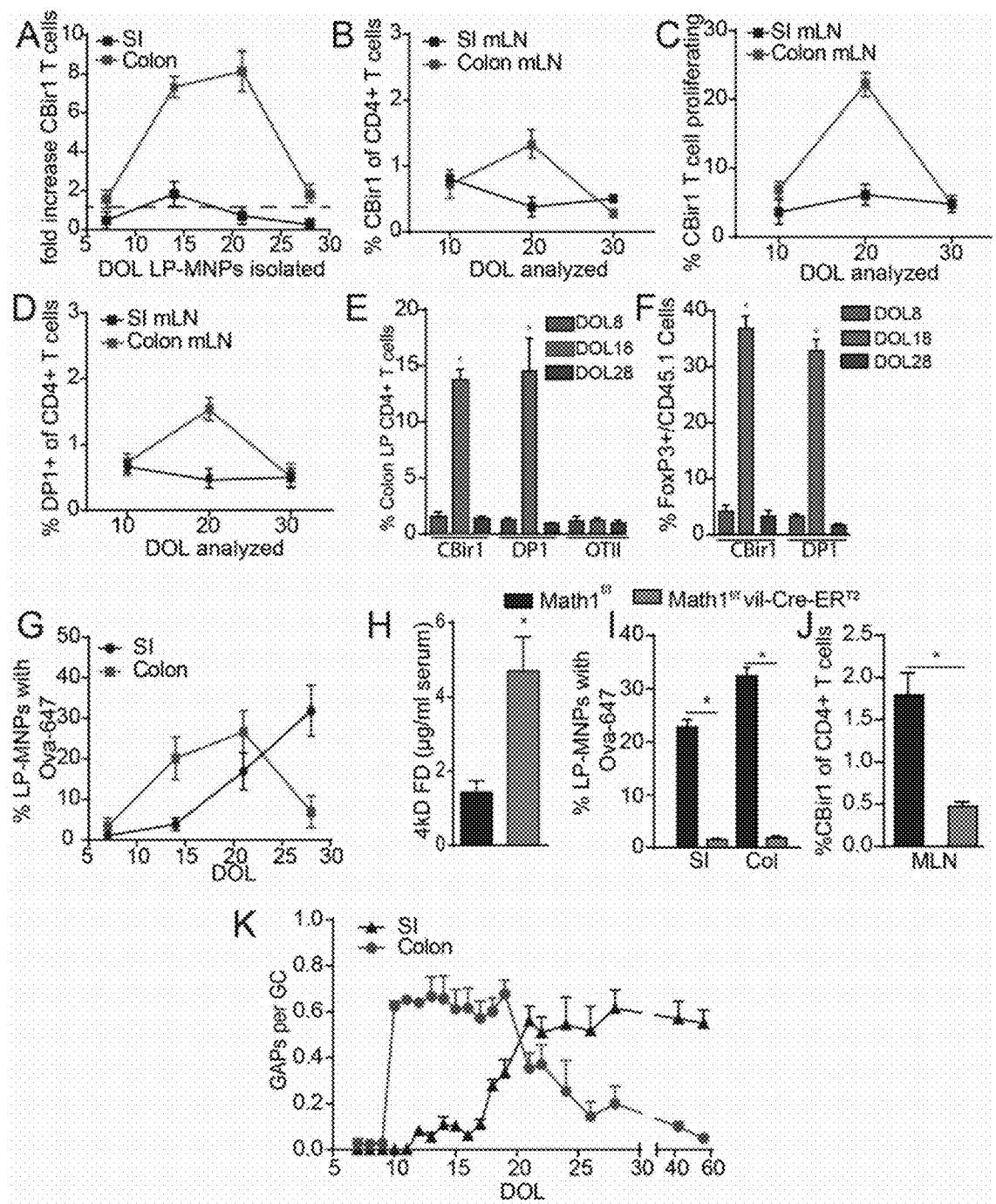
FIG. 23A-FIG. 23K is a series of graphs showing bacterial antigen encounter occurs during a specific pre-weaning interval, is dependent upon GCs, and correlates with the presence of colonic GAPs.
Figures 24A, 24B, 24C, 24D:
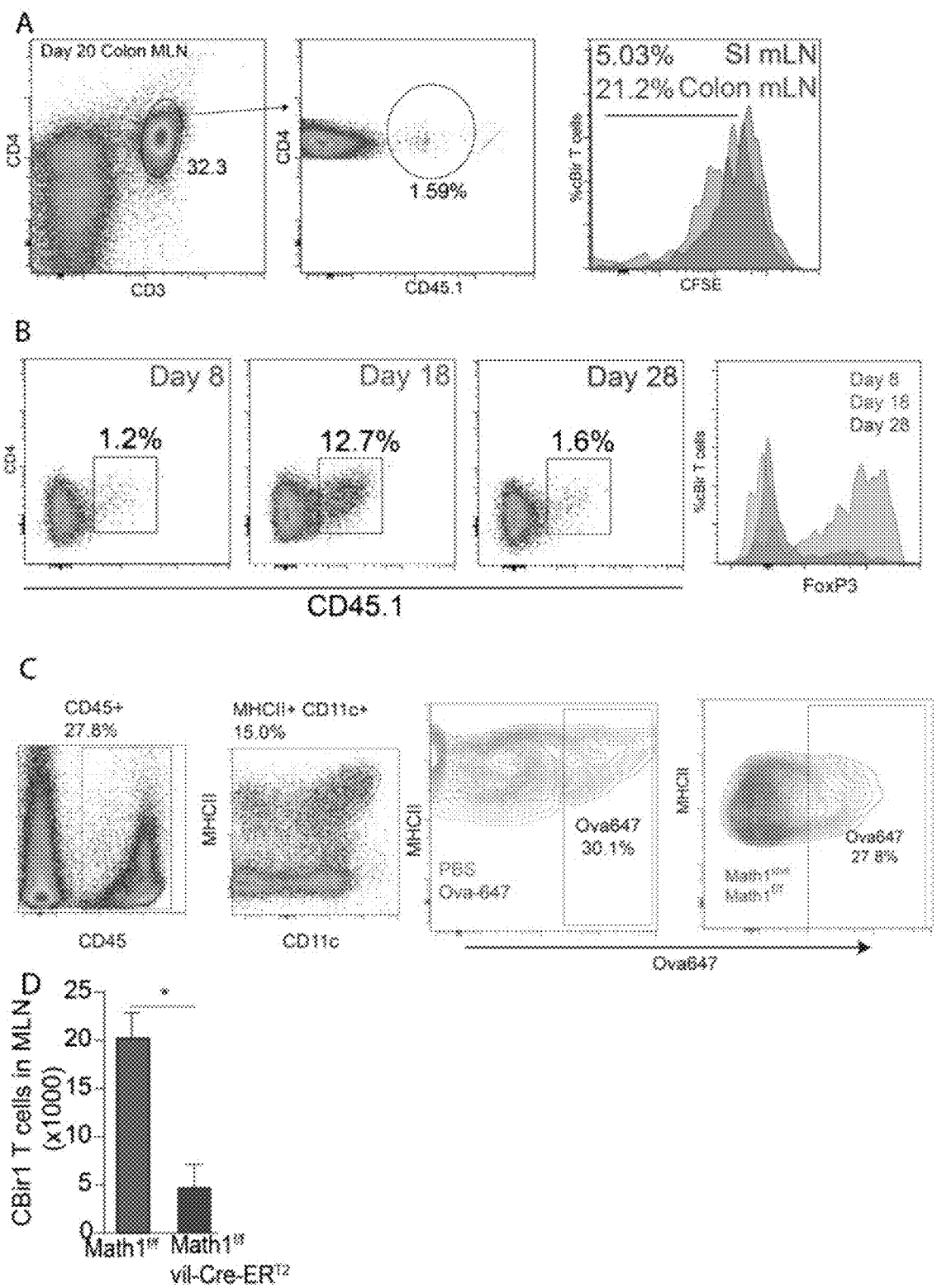
FIG. 24A-FIG. 24D is a series of representative flow cytometry plots and a graph related to FIG. 23.
Figures 25A, 25B:
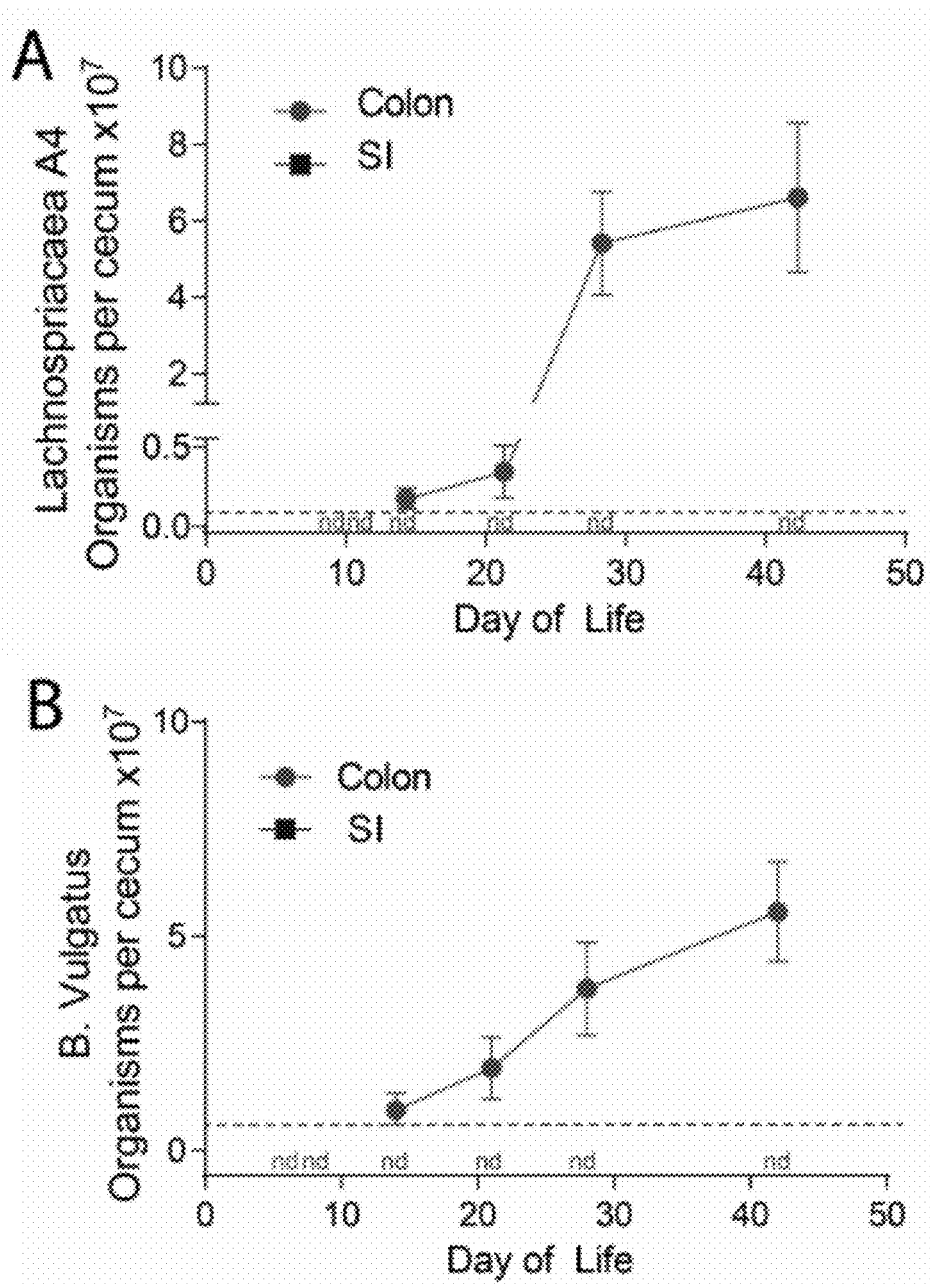
FIG. 25A-FIG. 25B is a series of graphs showing CBir1 epitope producing bacteria and *B. vulgatus* in the small intestinal and colonic contents by DOL.

While multiple studies have documented that gut bacteria can affect the outcome of T cell responses, fewer have examined how T cells encounter and respond to gut commensal bacterial antigens. Results from the few studies examining this topic indicate that T cell responses to gut bacteria are dominated by a relatively small number of taxa that are closely adherent to the epithelium, such as segmented filamentous bacteria (SFB) or *Helicobacter*, while in contrast antigens from other bacteria, such as *Bacteriodes vulgatus* and the Lachnospiraceae bacterium A4, do not elicit responses from antigen specific T cells in the absence of inflammation. A limitation of these studies is that they have examined adult mice or gnotobiotic mice, which may not reflect the physiologic interactions of the developing immune system with the microbiota in early life. To overcome this limitation, lamina propria (LP) CD11c+ MHCII+ populations were isolated, referred to as mononuclear phagocytes (MNPs), from the SI and colon of conventionally housed mice during early life and evaluated their ability to stimulate CBir1 CD4+ TCR transgenic T cells specific for a flagellin epitope produced by the Lachnospiraceae bacterium, A4, and COE1. It was observed that SI LP-MNPs were relatively ineffective at inducing CBir1 T cell expansion at all days examined (FIG. 23A). In contrast colonic LP-MNPs isolated on DOL14 and DOL21, but not earlier on DOL7 or later on DOL28, were able to induce strong proliferation of CBir1 T cells suggesting these LP-MNPs were loaded with the CBir1 flagellin epitope (see e.g., FIG. 23A). Adoptive transfer of CFSE labeled CBir1 T cells recapitulated the temporal and regional pattern of T cell stimulation in the gut in vivo, with effective accumulation and proliferation of CBir1 T cells in the colon draining MLN around DOL21 but not earlier on DOL10 or later on DOL30, and not in the SI draining MLN on any day examined (see e.g., FIG. 23B, FIG. 23C, FIG. 24). Likewise, it was observed that adoptively transferred DP1 CD4+ TCR transgenic T cells, specific for an antigen produced by B. vulgatus, localized to the colon draining MLN around DOL20 but not earlier on DOL10 or later on DOL30 and not to the SI draining MLN on any day examined (see e.g., FIG. 23D). CBir1 and DP1 TCR transgenic T cells transferred on DOL18, but not earlier on DOL8 or later on DOL28, and not ovalbumin (Ova) specific OTII TCR transgenic T cells in the absence of Ova, expanded in the colon LP, and expressed Foxp3 seven days later (see e.g., FIG. 23E, FIG. 23F, FIG. 24). This signifies that antigen specific Foxp3 pTreg responses are made towards multiple members of the commensal microbiota selectively during this pre-weaning interval. The lack of responses in the SI is likely due to the preferential localization of these bacterial taxa in the colon and the lack of responses in the colon around DOL10 may be accounted for by the low levels of these bacteria in the lumen during this time of life (see e.g., FIG. 25). However, the lack of responses in the colon around DOL30 were paradoxical as the flagellin peptide recognized by CBir1 T cells and the B. vulgatus bacteria recognized by DP1 T cells became more abundant in the colonic luminal contents around DOL30 (see e.g., FIG. 25), suggesting that LP-MNPs became unable to acquire these luminal microbial antigens.

To overcome the inability to assure microbial antigen presence at all time points in early life, the ability of SI and colon LP-MNPs to acquire a surrogate antigen Ova was evaluated. Fluorescent Ova acquisition by colonic LP-MNPs occurred in a pattern similar to that of CBir1 antigen (see e.g., FIG. 23 G, FIG. 24). In contrast SI LP-MNPs acquired fluorescent Ova around the time of weaning, DOL21, with limited capacity at earlier time points (see e.g., FIG. 23 G). Thus, the inability to stimulate gut bacteria antigen T cell responses prior to DOL10 might reflect both the limited presence of the antigen and the inability of LP-MNPs to acquire luminal antigens, while in contrast the inability to stimulate gut bacteria antigen T cell response in the colon post-weaning is reflective of the inability of colonic LP-MNPs to acquire antigen. Further the lack of T cell responses to bacterial antigen in the SI is not due to the inability of SI LP-MNPs to acquire luminal antigens post-weaning, but likely is reflective of the low levels of this bacterial antigen in the SI lumen (see e.g., FIG. 25).

Figure 26:
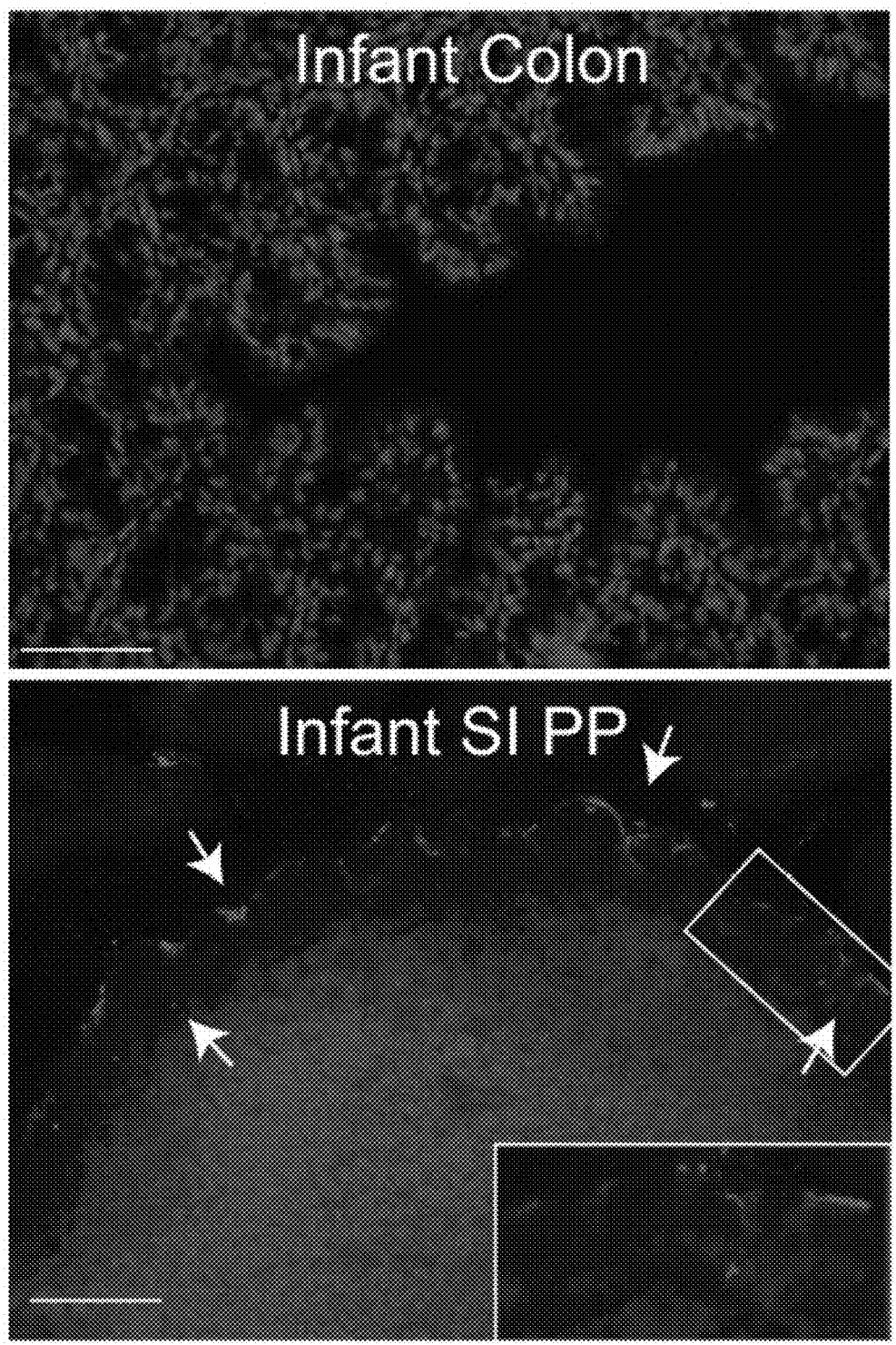
FIG. 26 M cells are not present on the non-follicle bearing epithelium in the colon in early life. Immunofluorescence staining for GP2 (red) revealed that M cells are not seen in the colonic epithelium (left panel) but were present in the follicle associated epithelium overlying Peyer's patches (PP) in the SI (right panel) of DOL19 mice. Blue=DAPI nuclear stain, scale bar=50 µm.
Figure 27A:
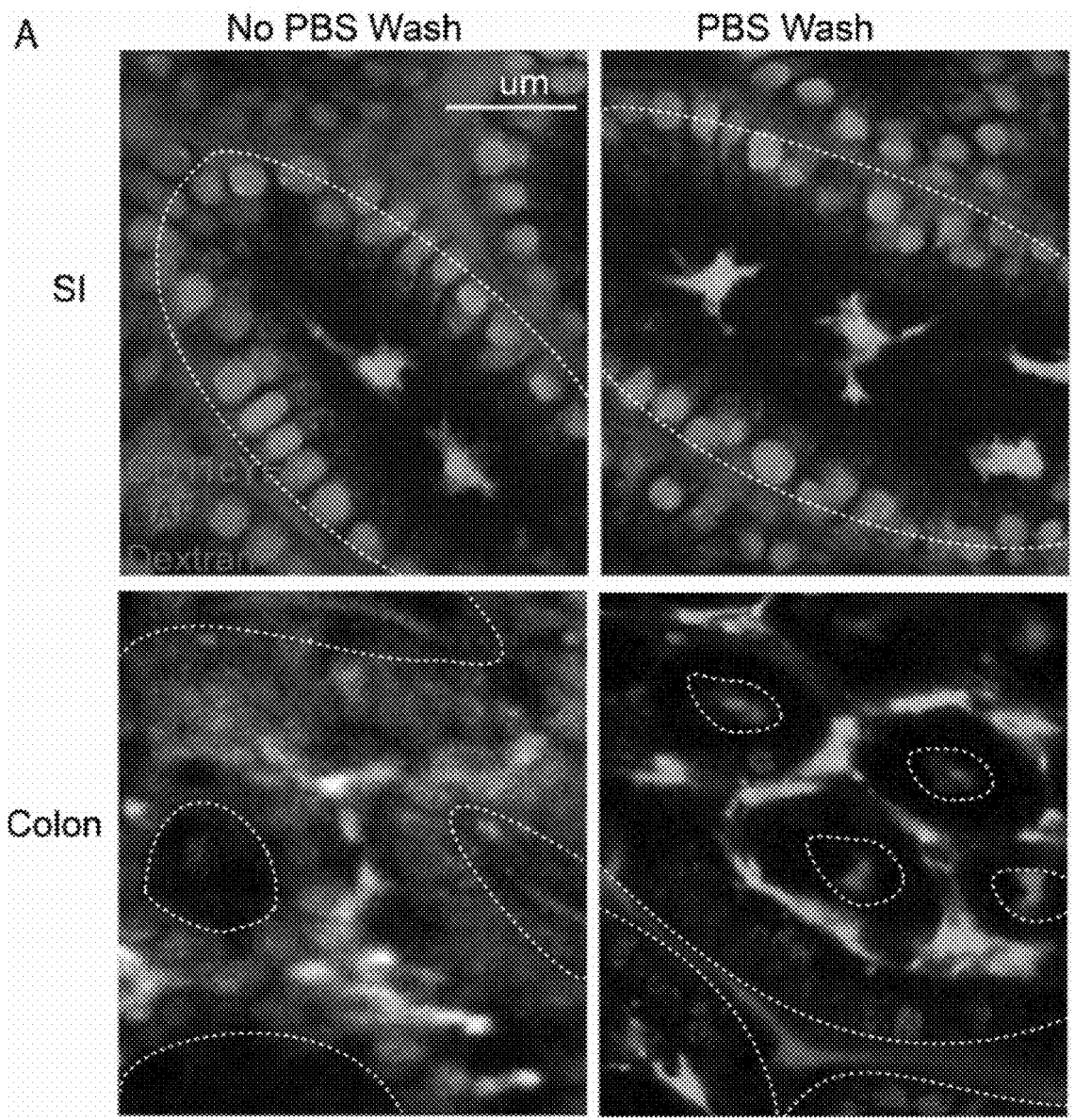
FIG. 27A-FIG. 27B is a series of images and a graph showing the extension of trans-epithelial dendrites by LP-MNPs is rare in the intestine of pre-weaning mice.
Figure 27B:
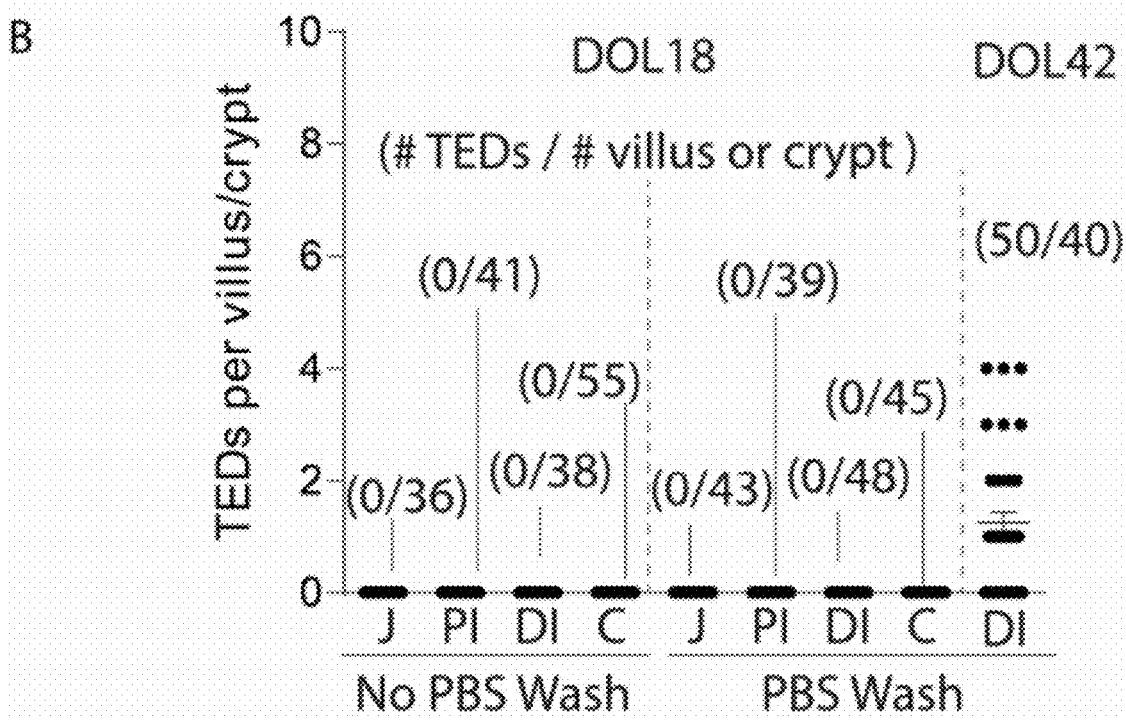
Figures 28A, 28B, 28C, 28D:
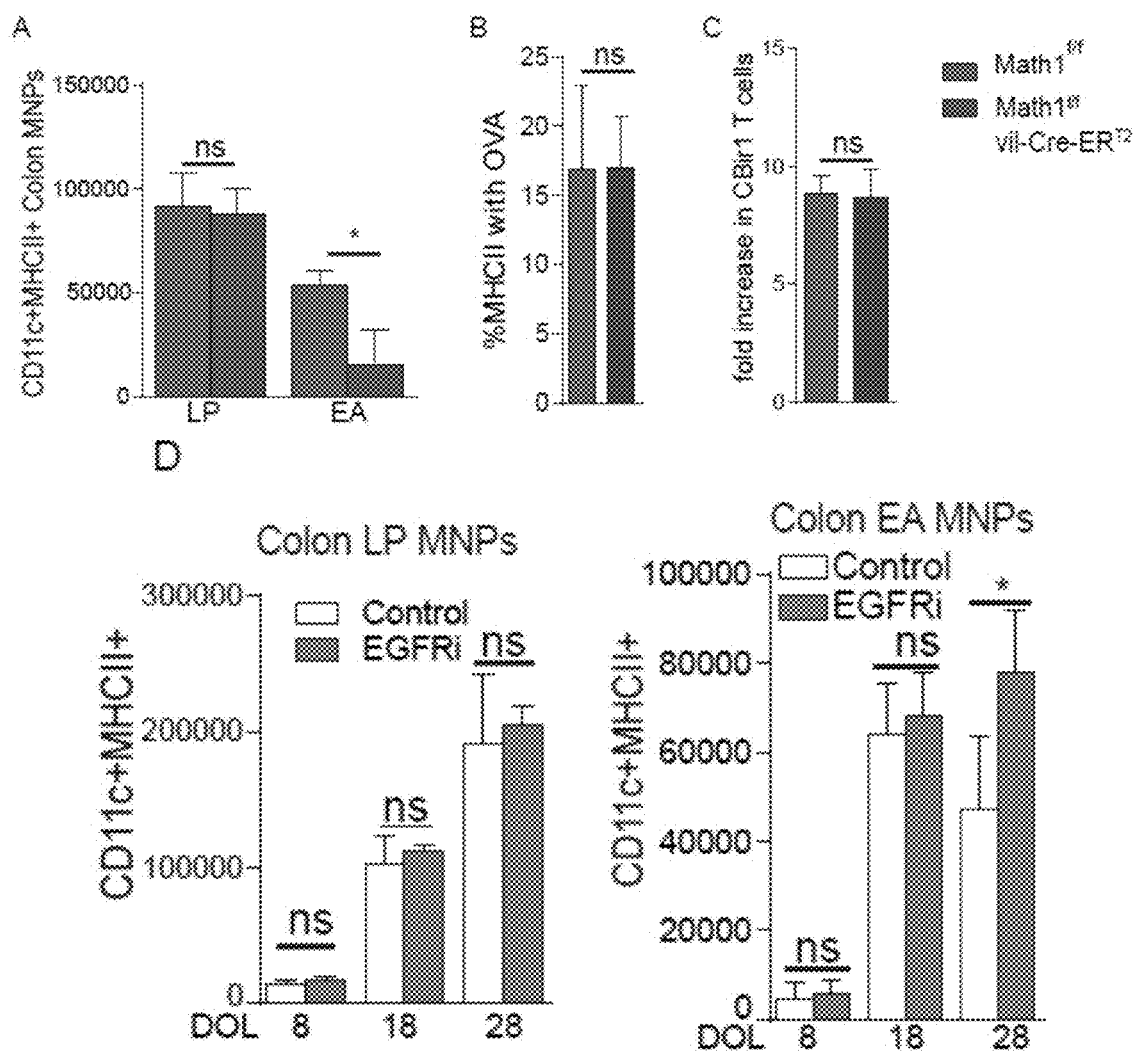
FIG. 28A-FIG. 28F is a series of bar graphs showing GAP manipulations in early life do not affect antigen presenting capacity of colonic lamina propria MNPs.
Figures 28E, 28F:
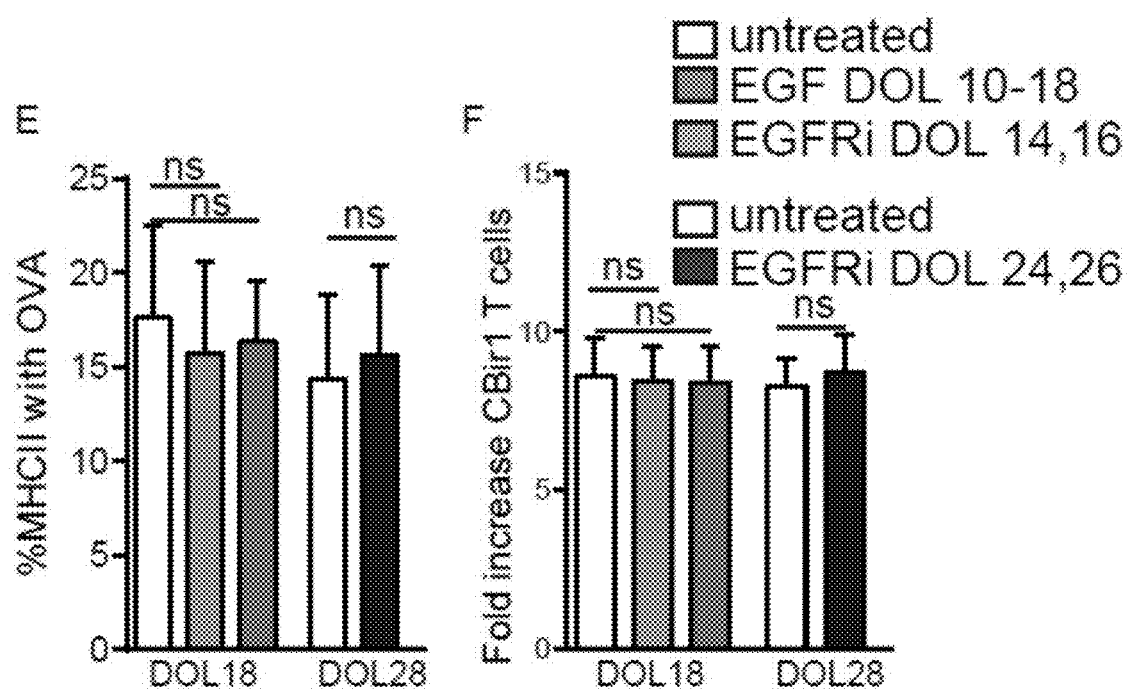
Figure 29A:
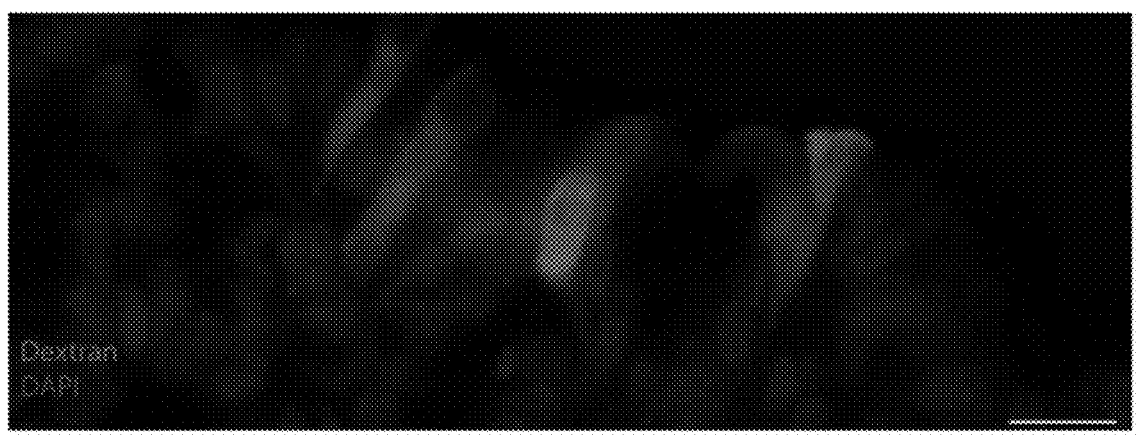
FIG. 29A-FIG. 29C is a series of immunofluorescent staining images and a bar graph showing dextran containing epithelial cells express the GC marker cytokeratin.
Figure 29B:
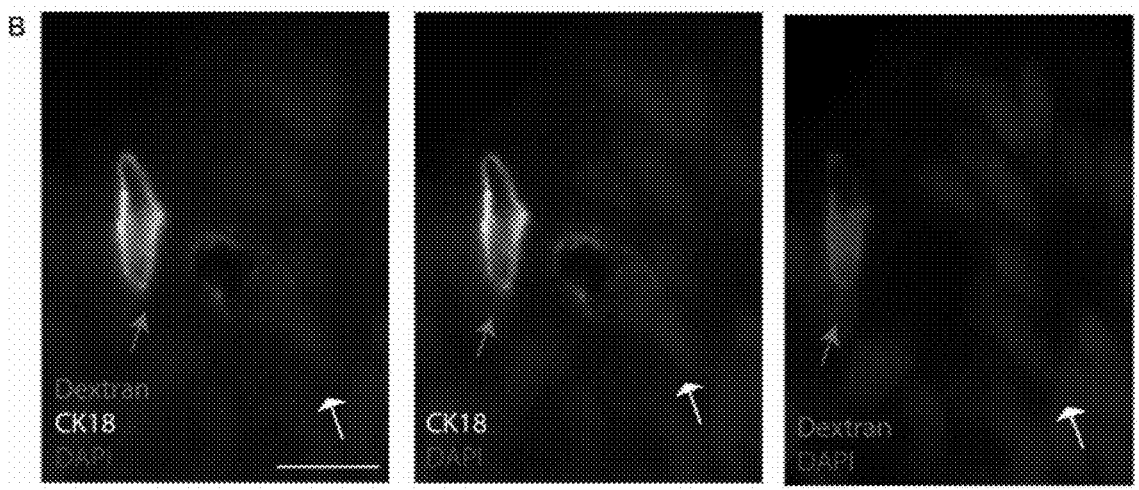
Figure 29C:
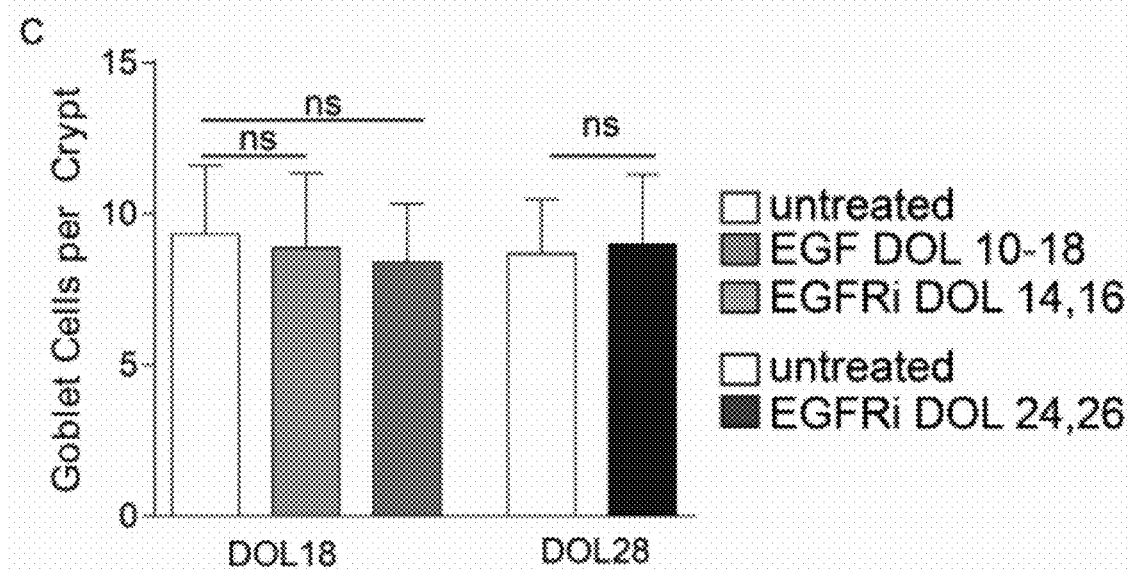

Several processes have been implicated in luminal antigen capture by LP-MNPs, however these processes have not been investigated in the pre-weaning intestine. Consistent with observations in the adult intestine, villous M-cells, or M-cells in the non-follicle bearing epithelium, were absent from the colon pre-weaning (see e.g., FIG. 26). CD11c+ APCs can extend trans-epithelial dendrites (TEDs) into the lumen of the SI for the purpose of sampling luminal antigens, however this has not been observed in the colon of adult mice where the majority of antigen is loading onto LP-MNPs prior to DOL 21 (see e.g., FIG. 23A and FIG. 23G). In vivo two-photon imaging of a DOL21 CD11 $c^{YFP}$ reporter mice did not reveal dendrites protruding past the intestinal epithelium in either the SI or the colon, though dendrites were readily observed in the LP probing the epithelium (see e.g., FIG. 26). Studies evaluating TED formation in adult mice removed luminal contents and mucus prior to imaging, a process, which induces TED formation in the SI, but not the colon of adult mice. It was observed that even after removal of the luminal contents and mucus layer, TEDs did not form in the SI or colon of DOL18 mice (see e.g., FIG. 26). Goblet cells (GCs) can form goblet cell associated antigen passages (GAPs) and deliver luminal substances to LP-MNPs in the SI of adult mice. Mouse atonal homologue 1 (Math1) is a transcription factor required for GC development, and inducible deletion of Math1 in intestinal epithelial cells results in GC deletion. It was observed that deletion of GCs in DOL18 Math1$^{f/f}$vil-Cre-ER$^{T2}$ mice resulted in a ~3 fold increase in intestinal permeability as evaluated by 4 kD FITC dextran presence in the serum following gavage (see e.g., FIG. 23H). Surprisingly, LP-MNPs from the SI or colon of DOL18 mice lacking GCs could not capture luminal fluorescent Ova (see e.g., FIG. 23I, FIG. 24), yet had a normal number of LP-MNPs and could capture fluorescent Ova when administered systemically (see e.g., FIG. 28). Moreover, CBir1T cells transferred into DOL 18 mice lacking GCs failed to expand in vivo (see e.g., FIG. 23J), despite the ability of colonic LP-MNPs from mice lacking GCs to expand CBir1 T cells similar to controls when antigen was added to ex vivo cultures (see e.g., FIG. 28). Thus, the presence of increased intestinal permeability did not correlate with the ability of LP-MNPs to capture luminal antigen and to stimulate immune responses in early life, and suggested that GCs and GAPs are required for LP-MNPs to acquire luminal antigens in the pre-weaning period. Therefore, the regional pattern and timing of GAP formation during early life was evaluated. GAPs were not seen in the colon or small intestine prior to DOL10 (see e.g., FIG. 23K). Around DOL10, GAPs were present in the colon (see e.g., FIG. 29) at a rate of 0.6 GAPs per goblet cells, and remained at that level until DOL21, the time of weaning, when GAP formation decreased to become rare in the colon at DOL24 (see e.g., FIG. 23K). At DOL18 GAPs became consistently present in the SI across multiple experiments and became prevalent at 0.6 GAPs per GC on DOL21 and remained at that level throughout adulthood (see e.g., FIG. 23K). Thus, GCs were required for the delivery of antigens to the LP-MNPs in early life, and the presence of GAPs, but not TED formation, increased intestinal permeability, or villous M cells correlated with the regional pattern and timing of antigen delivery during early life. three phases of luminal antigen delivery in the gut were defined; the neonatal phase (DOL0-10) in which antigens are not delivered to the SI or colonic immune system, the post-neonatal phase (DOL11-weaning) in which antigens are predominantly delivered to the colonic immune system, and the post-weaning phase when antigens are delivered predominantly to the SI immune system.

The Gut Microbiota and Breast Milk Control Luminal Antigen Delivery in Early Life.

GCs in the colon of adult mice are largely unable to form GAPs due to Myd88 dependent GC intrinsic sensing of the abundant colonic microbes and microbial products. GC microbial sensing activates the epidermal growth factor receptor (EGFR) and p42/p44 mitogen activated protein kinase (MAPK), inhibiting GC responses to acetylcholine (ACh), the stimulus inducing spontaneous GAP formation. Like intestinal GCs from adults, GCs from pre-weaning DOL18 mice expressed TLRs, Myd88, and EGFR (see e.g., FIG. 30A), suggesting that they would respond similarly to microbial products. Indeed, colonic GAPs on DOL18 could be inhibited by heat killed cecal contents from adult SPF housed mice and this inhibition was dependent upon Myd88 in Math1 expressing epithelial lineages, which is largely restricted to GCs in the colon (see e.g., FIG. 30B). Intraluminal LPS inhibited GAP formation in the DOL18 colon, and this inhibition was dependent upon activation of EGFR and MAPK (see e.g., FIG. 30C), confirming the pathways downstream of microbial sensing seen in GCs in the adult colon applies to pre-weaning colonic GCs as well. The gut microbiota undergoes dramatic changes in quantity and diversity from birth to weaning. The cecal bacterial load increased little during the neonatal phase, but then logarithmically increased during the post-neonatal phase and post-weaning before plateauing during adulthood (see e.g., FIG. 30D). This quantitative increase in bacterial load correlated with qualitative changes as seen by 16s deep sequencing (see e.g., FIG. 30E), with a switch from gammaproteobacteria to clostridia, bacilli, and bacteroidia in early life. Indeed, when Myd88 was deleted from GCs, GAPs formed spontaneously in the post-weaning colon, but the density of colonic GAPs in earlier phases of life, and in the small intestine remained unchanged (see e.g., FIG. 30F, FIG. 30G), indicating that Myd88 dependent signals suppress GAP formation specifically in the colon, in the post-weaning period. Therefore, while both pre-weaning and post-weaning colonic GCs can respond to microbial signals to inhibit GAP formation, the gut microbiota is permissive for the spontaneous formation of colonic GAPs pre-weaning.

Figures 31A, 31B, 31C, 31D, 31E, 31F, 31G, 31H, 31I, 31J:
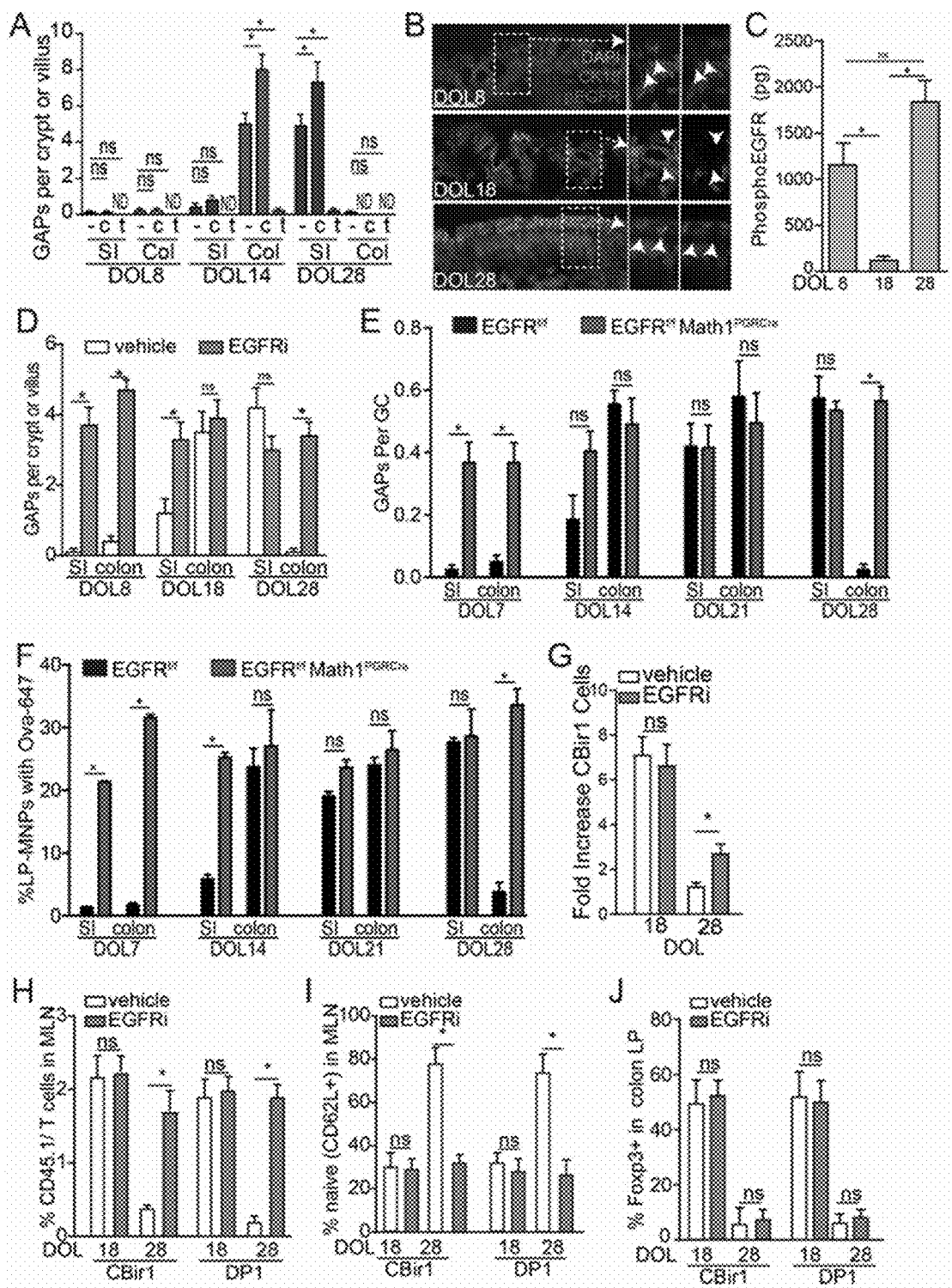
FIG. 31A-FIG. 31J is a series of bar graphs and images showing EGFR activation in GCs inhibits GAP formation and luminal antigen delivery throughout life.
Figure 32A:
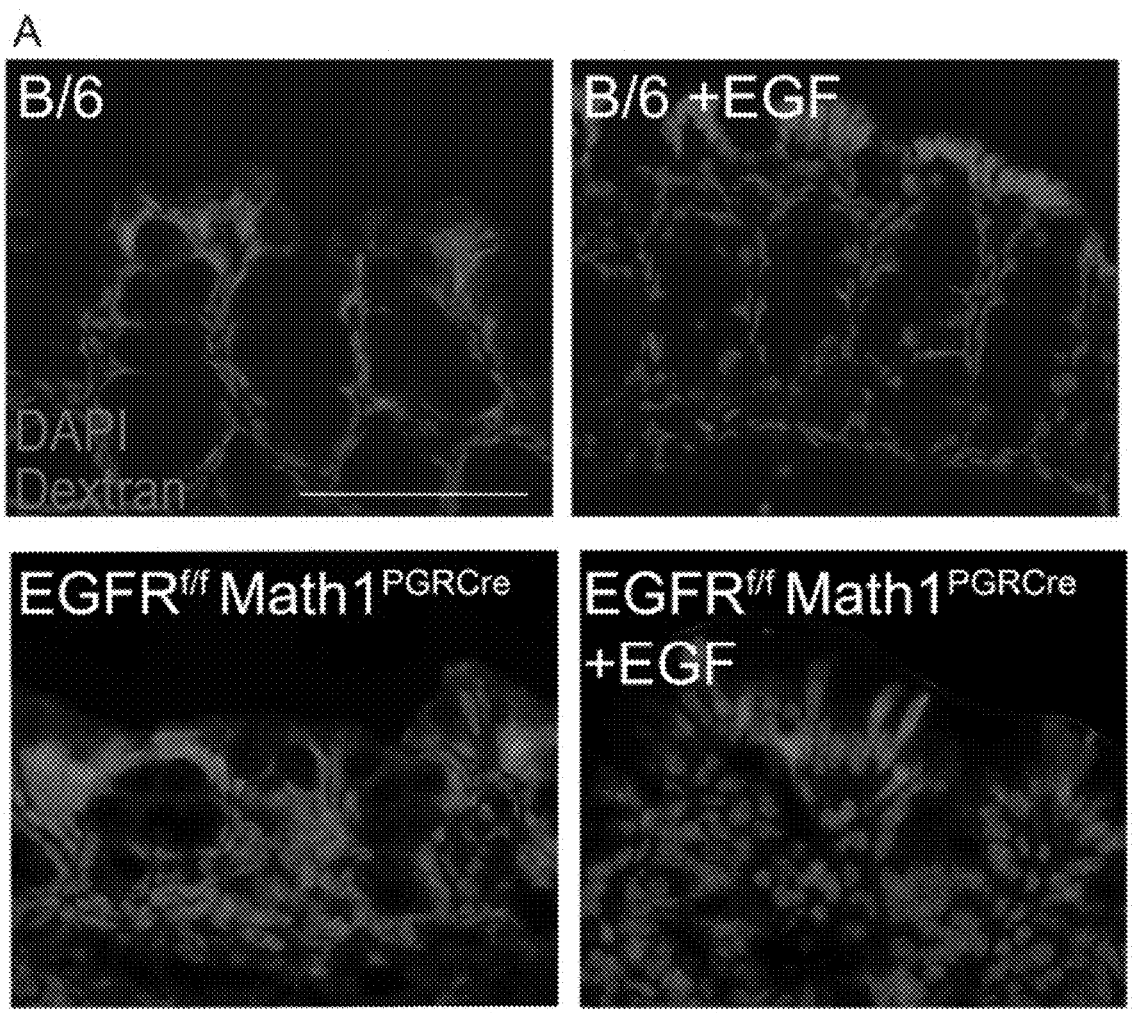
FIG. 32A-FIG. 32B is a series of images and a bar graph showing EGF inhibits colonic GAPs in the post-neonatal phase of life in a GC intrinsic manner.
Figure 32:
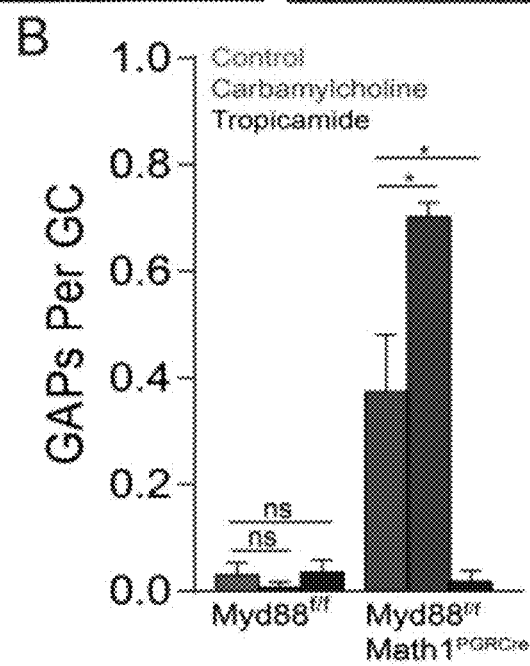

The lack of GAPs in the neonatal phase of mice lacking Myd88 in GCs could be due to the lack of ACh, the stimulus spontaneously inducing GAPs or due to lack of GC responsiveness to ACh due to other pathways activating the EGFR in GCs. The ability of GCs to respond to ACh analogue carbamylcholine (CCh) to form GAPs was evaluated. SI and colonic GCs in DOL8 mice, the neonatal phase, did not form GAPs in response to CCh (see e.g., FIG. 31A). SI GCs in DOL 14 mice, the post-neonatal phase, were relatively unresponsive to CCh, while colonic GCs were responsive to CCh to form GAPs (see e.g., FIG. 31A). Moreover, spontaneously forming colonic GAPs on DOL 14 were suppressed by tropicamide, an antagonist of muscarinic ACh receptor 4 (mAChR$_4$; see e.g., FIG. 31A), the ACh receptor on GCs inducing GAPs in the adult SI. In contrast, GCs in the post-weaning phase responded similar to what has been reported for adults with SI GCs increasing GAPs in response to CCh and spontaneously forming GAPs via mAChR$_4$ signals, and colonic GCs being unresponsive to CCh to form GAPs (see e.g., FIG. 31A). This suppression post-weaning was relieved by deletion of Myd88 in GCs, which allowed GAPs to be form spontaneously in a mAChR4 dependent manner and to be further induced by CCh (see e.g., FIG. 32). This indicates that the pattern of GC responsiveness to ACh to form GAPs changes throughout early life, prompting us to explore if other ligands/pathways activate EGFR and p42/p44 MAPK at these times of life. Consistent with EGFR activation inhibiting GAPs in the pre-weaning colon, phosphorylation of the EGFR in GCs inversely correlated with the presence of colonic GAPs pre-weaning (compare e.g., FIG. 31 B-FIG. 31C with FIG. 23K) and inhibition of EGFR phosphorylation with tryphostin AG1483 (EGFRi), or deletion of EGFR in GCs, allowed GAP formation in the SI and colon during all phases of early life, independent of changes to the number of GCs (see e.g., FIG. 31D-FIG. 31E, FIG. 29).

Intraluminal fluorescent Ova-647 was captured by SI and colonic LP-MNPs in all phases of life in mice lacking EGFR in GCs (see e.g., FIG. 31 F), indicating that EGFR activation in GCs was controlling the regional and temporal pattern of antigen delivery in early life. Inhibition of EGFR activation allowed colonic LP-MNPs from post-weaning mice to capture microbial antigen to stimulate CBir1 T cells ex-vivo (see e.g., FIG. 31G). The presence of GAPs correlated with MNP recruitment to the colonic epithelium and the acquisition of luminal ova (see e.g., FIG. 28). However, these GAP manipulations did not affect the overall number of MNPs in the colonic LP, the ability of MNPs to capture systemic antigens, or their ability to stimulate bacterial antigen specific T cell proliferation when antigen was added to ex vivo cultures (see e.g., FIG. 28). This indicates that GAP manipulation specifically affected luminal antigen delivery to MNPs but not their presence within the colonic LP or their antigen presentation capacity. Additionally, inhibition of EGFR activation allowed adoptively transferred CBir1 or DP1 cells to expand and become activated in the MLN of post-weaning mice while cells transferred into post-weaning vehicle treated mice, lacking colonic GAPs, remained naïve (see e.g., FIG. 31H and I). However, unlike microbial antigen specific T cells encountering antigen in the post-neonatal phase of life, DOL18, CBir1and DP1 T cells encountering microbial antigen post-weaning, DOL28, had little Foxp3 expression seven days post transfer (see e.g., FIG. 31J), indicating that the colon LP of post-neonatal mice is uniquely favorable for the induction of regulatory responses.

Figures 33A, 33B, 33C, 33D, 33E, 33F, 33G:
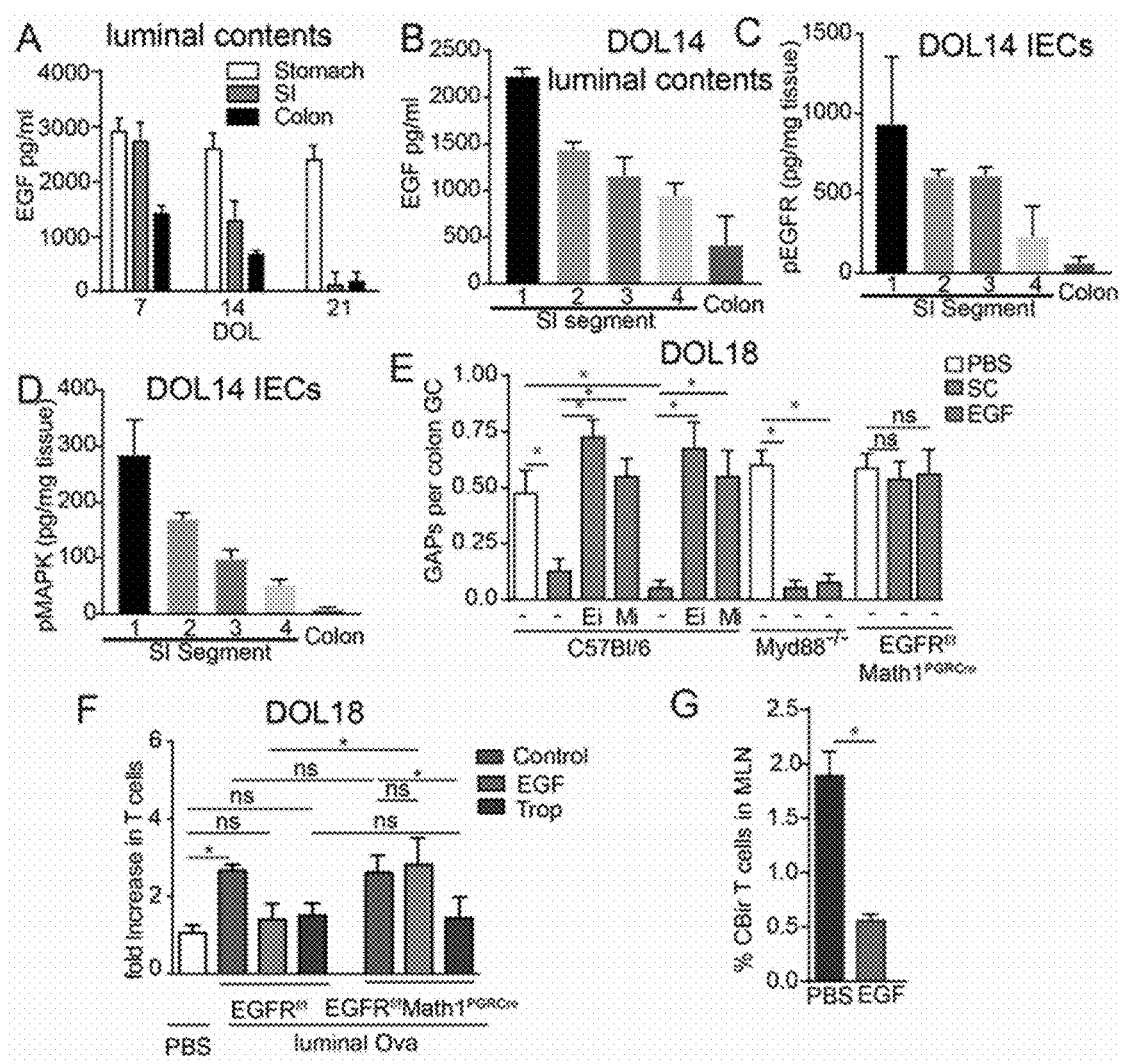
FIG. 33A-FIG. 33G is a series of graphs showing luminal EGF inhibits GAPs and antigen delivery prior to weaning.

Because pathways independent of Myd88 were activating EGFR in GCs to suppress GAPs, the pattern of EGFR ligands in the pre-weaning gut were evaluated. EGFR ligands, including EGF, amphiregulin, and heparin-binding EGF like growth factor, are abundant in the breast milk after parturition and decrease throughout lactation until weaning. Of these, EGF is the most abundant in breast milk, being ~5 fold higher than the others. Furthermore, ingested breast milk EGF reaches the offspring's GI tract in a biologically active form. It was observed that EGF was present in luminal contents throughout the GI tract of mice prior to weaning in a concentration pattern inversely correlating with the presence of GAPs (see e.g., FIG. 33A compare with FIG. 23K). The concentration of EGF decreased both throughout the GI tract, and over time, and correlated with the activation of the EGFR and p42/p44 MAPK in the epithelium (see e.g., FIG. 33A-FIG. 33D), indicating that the proximal to distal gradient and temporal decrement of luminal EGF could allow GAP formation to occur in a distal to proximal and temporal pattern as was observed in the gut during early life. Luminal EGF inhibits GAPs, and accordingly the stomach contents from DOL10 mice, which contains high levels of EGF, inhibited GAPs in the colon of DOL18 mice in a manner dependent upon EGFR and p42/p44 MAPK activation (see e.g., FIG. 33E). Stomach contents also inhibited colonic GAP formation in DOL18 Myd88$^{-/-}$ mice (see e.g., FIG. 33E) confirming the inhibitory ligands present in the stomach contents of neonatal mice were not microbial ligands acting via Myd88. Indeed, luminal recombinant EGF inhibited GAPs and luminal antigen loading of LP-MNPs in post-neonatal colon, in a EGFR and MAPK dependent, but Myd88 independent manner (see e.g., FIG. 33E-F and FIG. 32). Moreover, CBir1 cells failed to expand in the colon draining MLN three days post transfer in post-neonatal mice given intracolonic recombinant EGF (see e.g., FIG. 33G). These data indicate that breast milk EGF and potentially other EGFR ligands control the temporal and regional luminal antigen exposure of the gut immune system pre-weaning.

Altering the Timing of Exposure to Bacterial Antigens Results in Loss of Tolerance to Gut Bacteria, Worsened Colitis, and Inflammatory Responses to Gut Bacteria Following Epithelial Injury.

Figures 34A, 34B, 34C, 34D, 34E, 34F:
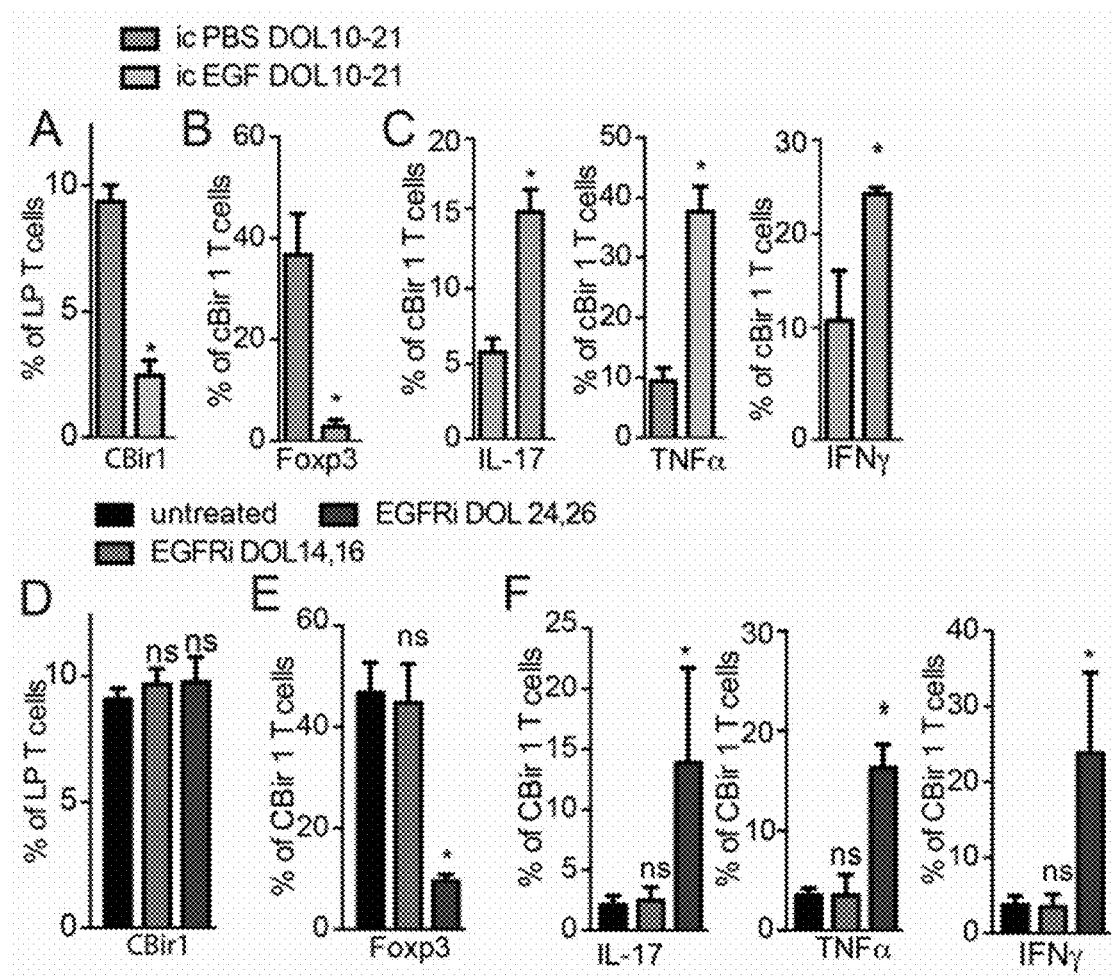
FIG. 34A-FIG. 34F is a series of bar graphs showing inhibiting or altering the timing of microbial antigen encounter results in inflammatory T cell responses against gut bacteria.
Figure 35:
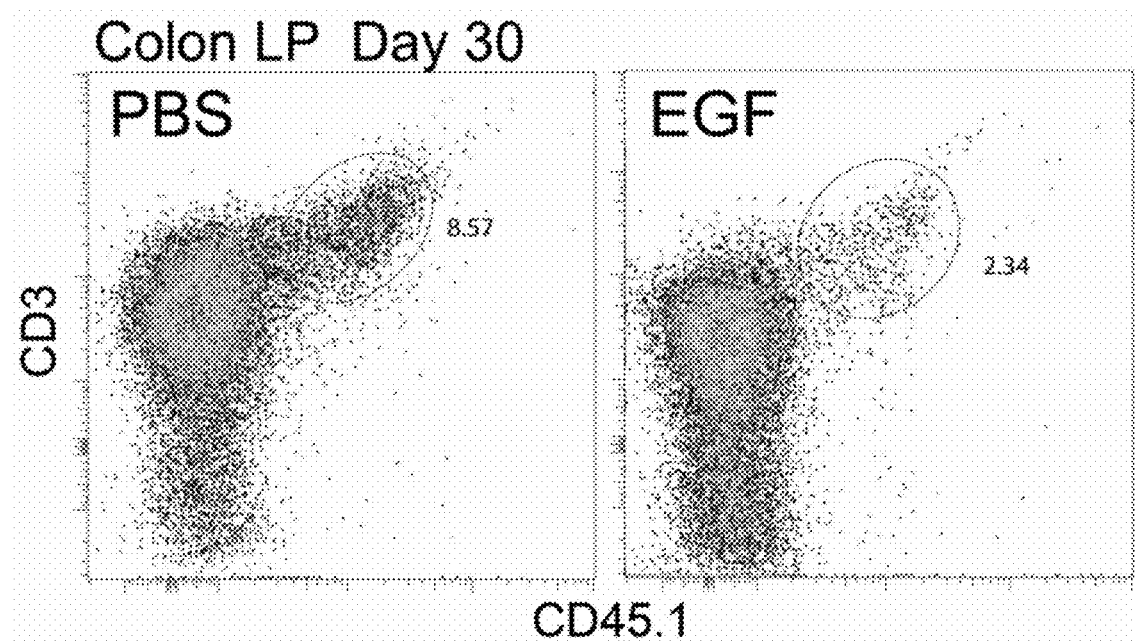
FIG. 35 is a series of flow plots showing inhibition of GAPs in the post-neonatal phase of life abrogates T cell responses to a gut bacteria. Representative flow plots identifying CD45.1+CD3+CD4+ CBir1 T cells in the colon LP and on DOL30, two weeks after transfer. Mice received intracolonic PBS or EGF, to inhibit colonic GAPS from DOL10-21.

It was evaluated whether GAP dysregulation or disruption affects the development of microbial specific Tregs. CBir1 T cells transferred into mice given intracolonic EGF on DOL10-21, to inhibit colonic GAPs, had significantly less expansion and expressed significantly less Foxp3 on DOL30 (see e.g., FIG. 34A and FIG. 24B and FIG. 35). However, a significantly larger proportion of the remaining CBir1 T cell population expressed inflammatory cytokines, when compared to PBS treated control mice (see e.g., FIG. 34C). Conversely, inhibition of EGFR on DOL14 and 16, during the post-neonatal phase, or on DOL24 and 26, post-weaning, did not affect the expansion of transferred CBir1 T cells (see e.g., FIG. 34D). However, unlike control treated mice or mice given EGFR inhibitors on DOL14 and 16 during the post-neonatal phase, CBir1 T cells in mice given EGFR inhibitors on DOL24 and 26 post-weaning, to allow encounters with microbial antigen outside of the normal window, expressed significantly less Foxp3 and a significantly greater proportion of the population expressed inflammatory cytokines (see e.g., FIG. 34E and FIG. 34F). Inhibition of EGFR during the post-neonatal phase on DOL14 and 16, when colonic GAPs are already present, resulted in no significant difference in the expression of Foxp3+ or inflammatory cytokines by transferred CBir1 T cells when compared with controls (see e.g., FIG. 34E and FIG. 34F). This supports that the effects of EGFR inhibition post-weaning on CBir1 T cells is a result of the induction of colonic GAPs and extension of the window of microbial antigen encounter.

Figures 36A, 36B, 36C, 36D, 36E:
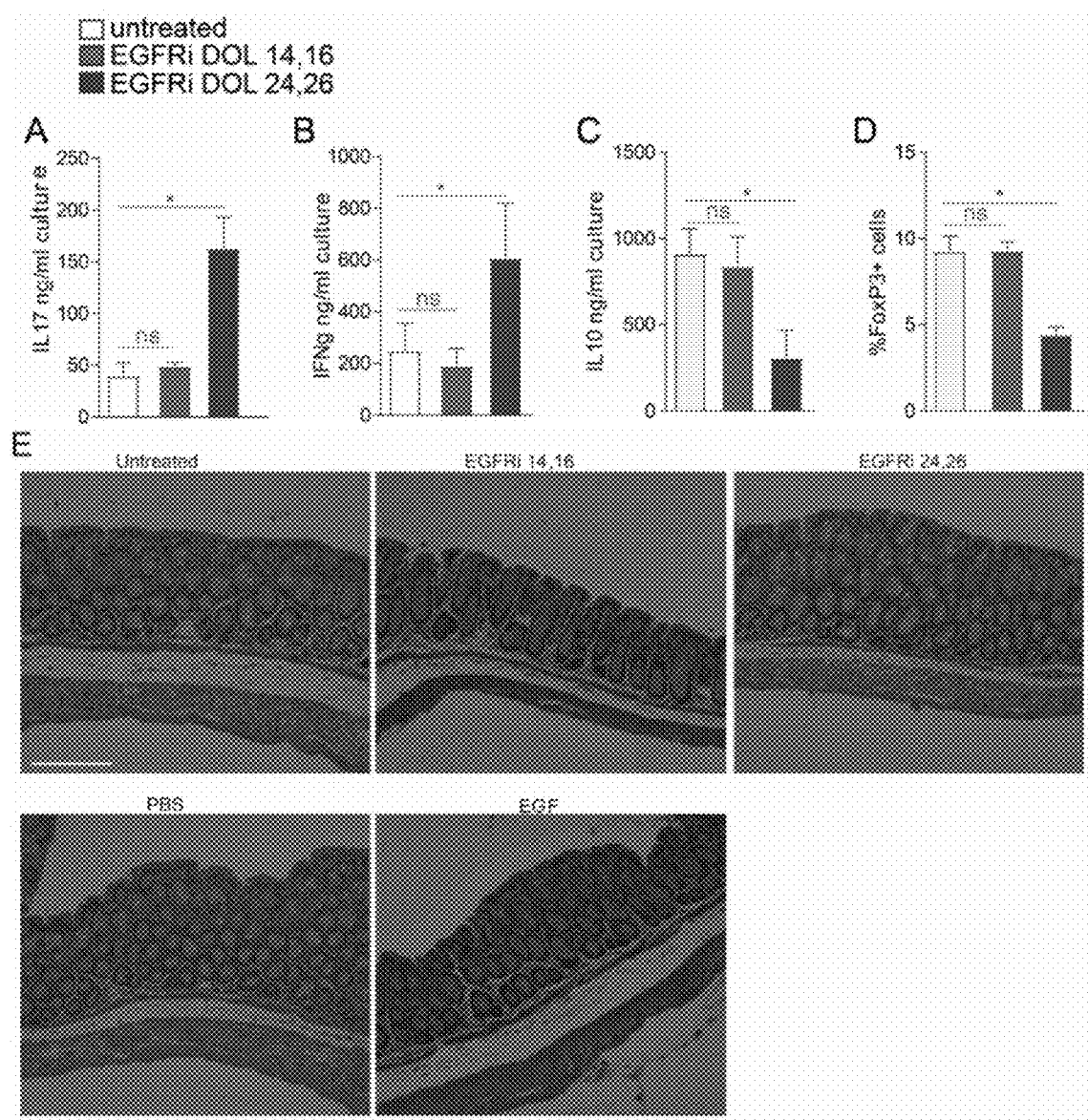
FIG. 36A-FIG. 36E are a series of bar graphs and images showing EGFR inhibition post-weaning, to inappropriately induce colonic GAPs, but not in the post-neonatal phase, when GAPs are present, results in inflammatory cytokine production in the colon draining MLN, but does not induce overt pathologic changes.
Figures 37A, 37B, 37C, 37D, 37E, 37F, 37G, 37H, 37I, 37J, 37K, 37L:
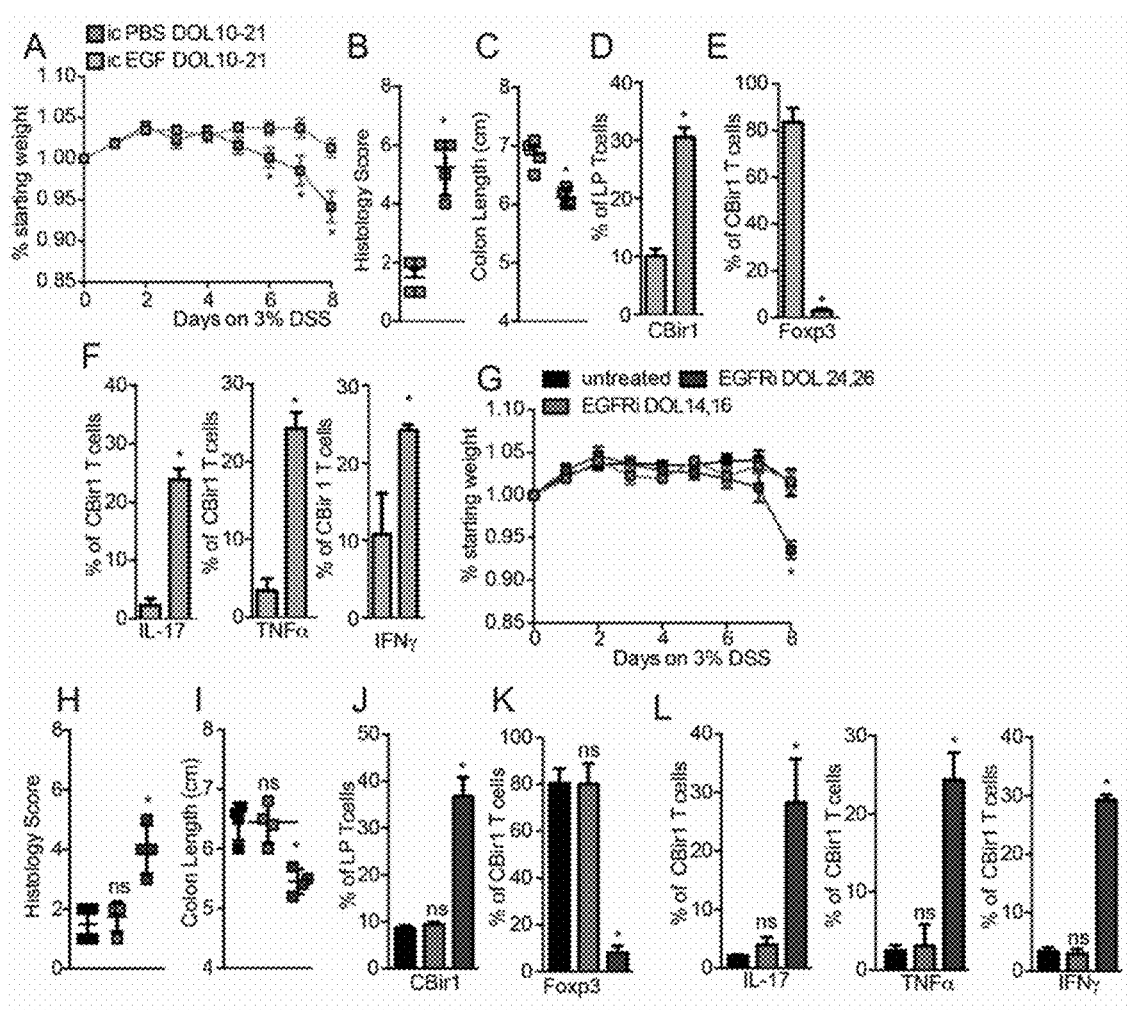
FIG. 37A-FIG. 37L is a series of graphs showing inhibiting or altering the timing of microbial antigen encounter results in inflammatory T cell responses against gut bacteria and worsened colitis upon epithelial damage.
Figures 38A, 38B, 38C:
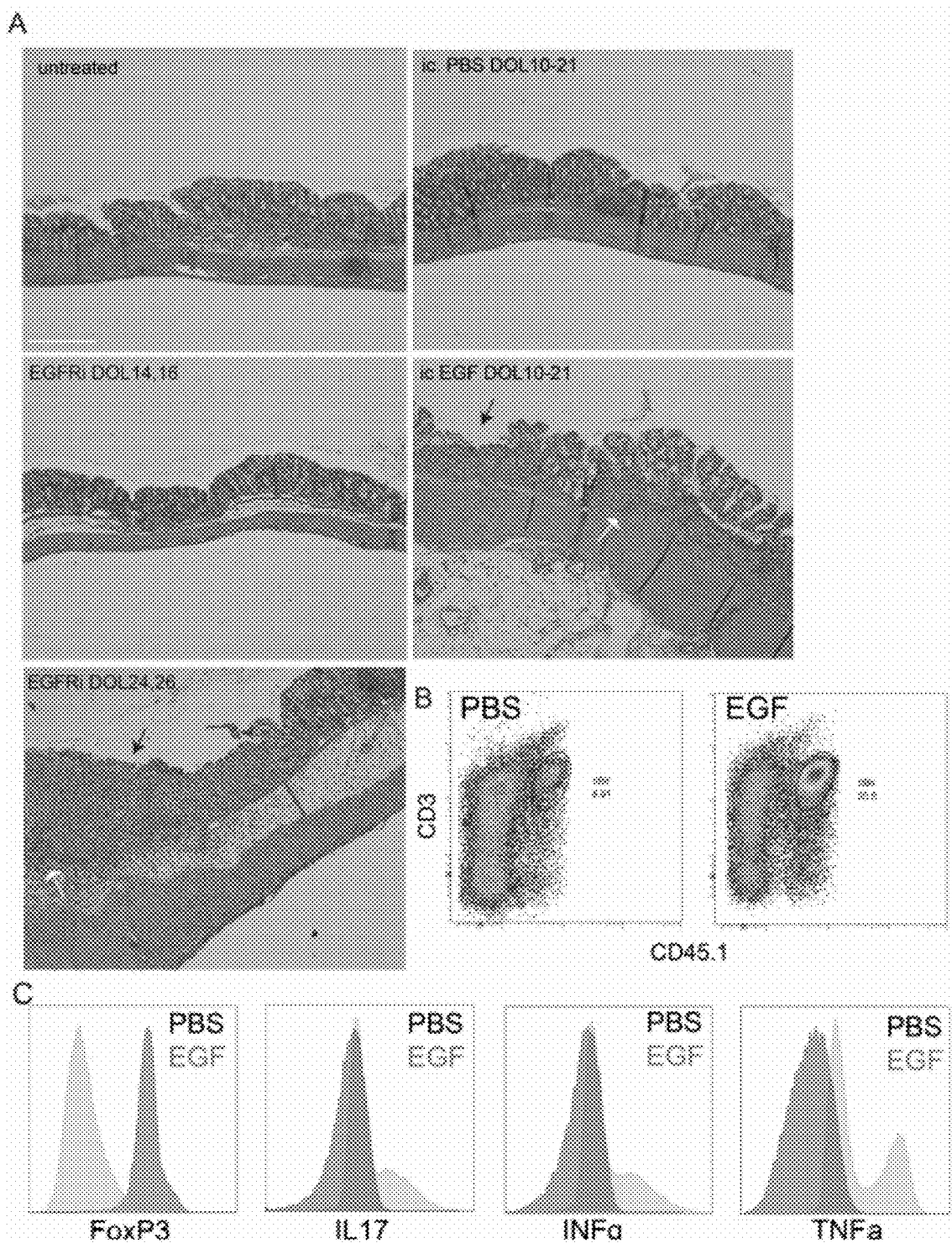
FIG. 38A-FIG. 38C is a series of images, flow plots, and expression plots showing worsened DSS colitis and inflammatory responses to commensal bacterial when encounters with microbial antigens are altered in early life.
Figures 39A, 39B, 39C, 39D, 39E, 39F, 39G, 39H, 39I, 39J, 39K:
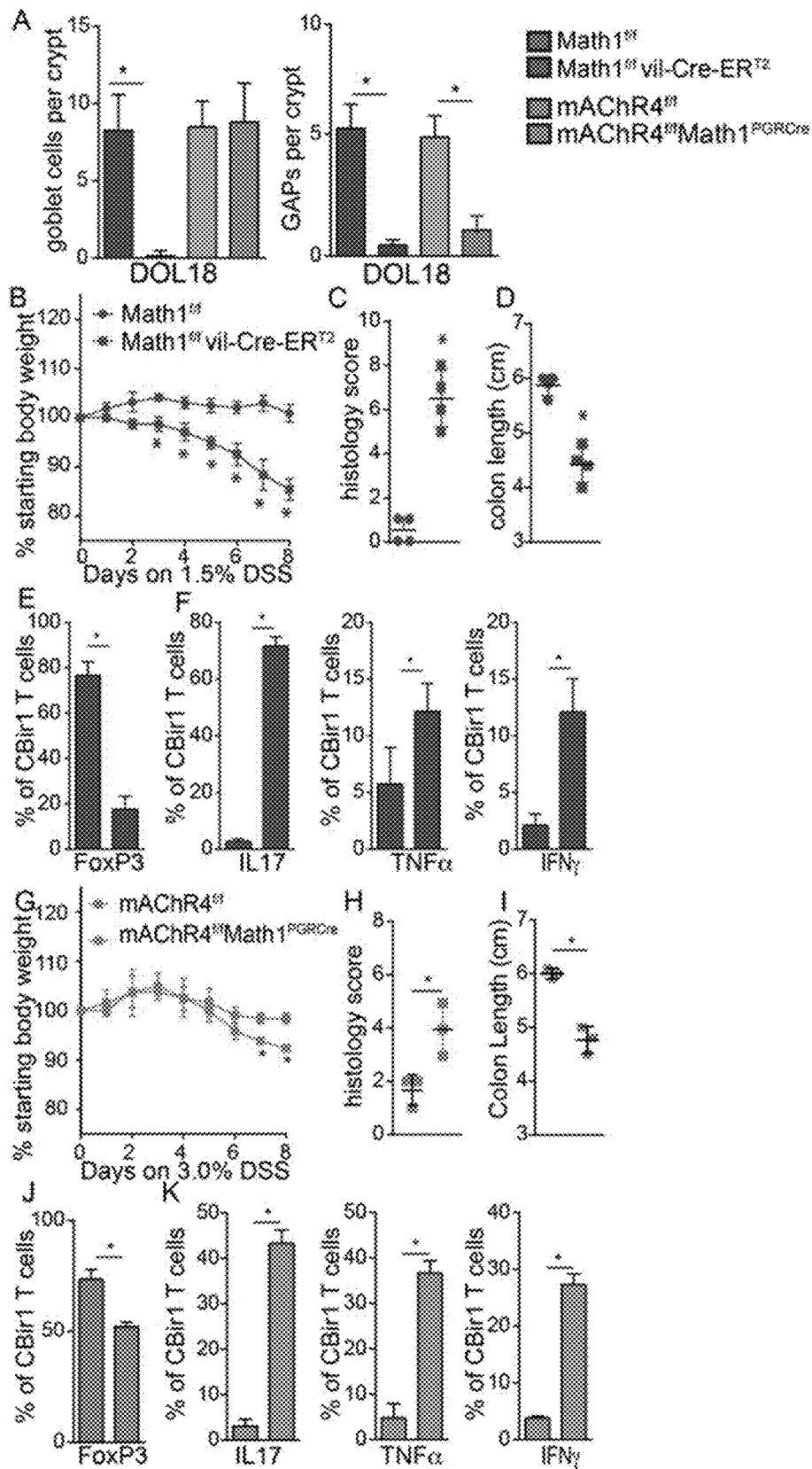
FIG. 39A-FIG. 39K is a series of graphs showing deletion of GCs or GAPs during early life results in inflammatory T cell responses against gut bacteria and worsened colitis later in life.
Figure 40:
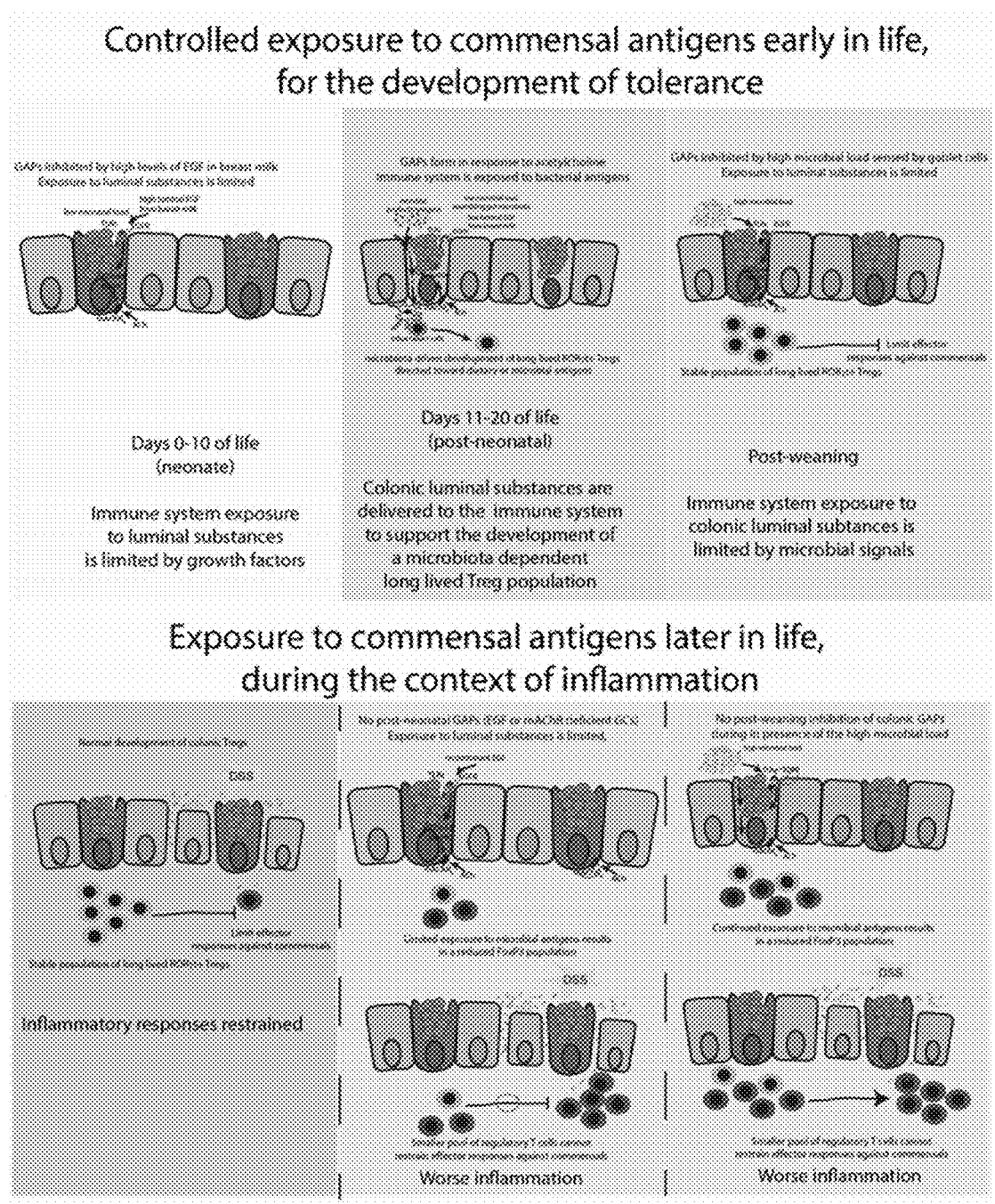
FIG. 40 is an illustration of a summary Schematic.

Altering the timing of microbial antigen encounter resulted in inflammatory cytokine production in the MLN one week later, but no overt pathology in the colon (see e.g., FIG. 36). It was reasoned that the lack of pathology might in part be due to the relatively low level of microbial antigen encountered by the immune system post-weaning, as was observed, little or no responses by bacterial antigen specific T cells adoptively transferred into mice post-weaning (see e.g., FIG. 23B-FIG. 23D). Therefore, mice given intracolonic EGF on DOL10-21 to inhibit microbial antigen encounter and pTreg development, mice given EGFR inhibitors post-weaning on DOL 24 and 26 to alter the timing of microbial antigen encounter, and control mice were given 3% dextran sodium sulfate (DSS) in drinking water on DOL30-38 to disrupt the colonic epithelial barrier and allow exposure of the immune system to luminal bacteria. Mice treated with EGF on DOL10-21, or EGFR inhibition on DOL 24 and 26, lost significantly more weight (see e.g., FIG. 37A and FIG. 37G) and developed significantly worse disease as evidenced by histology demonstrating increased edema, increased ulceration, increased cellular infiltration, and shortened colons (see e.g., FIG. 37B, FIG. 37C, FIG. 37H, and FIG. 37I and FIG. 38). In untreated mice, mice receiving intrarectal PBS on DOL10-21, and mice receiving EGFR inhibitors in the post-neonatal phase on DOL14 and 16 when colonic GAPs are normally present, transferred CBir1 T cells did not expand further in the colon LP (compare FIG. 23E with FIG. 37D and FIG. 37J), and continued expressing Foxp3 but not inflammatory cytokines after DSS treatment (see e.g., FIG. 37 E, FIG. 37F, FIG. 37K and FIG. 37L). However, in mice where microbial antigen encounter was inhibited by EGF, or inappropriately induced post-weaning by EGFR inhibition on DOL24 and 26, DSS treatment resulted in significant expansion of CBir1 T cells in colon LP (see e.g., FIG. 37D and FIG. 37J). The transferred CBir1 T cells had significantly reduced Foxp3 expression and significantly increased inflammatory cytokines (see e.g., FIG. 37E, FIG. 37F, FIG. 37K, and FIG. 37L) indicative of effector T cell expansion during inflammation in response commensal bacteria. Similarly, mice lacking GCs and GAPs beginning on DOL 12, or mice with deletion of mAChR4 on GCs between DOL 10 and 21, which have GCs but are unable to form GAPs during this interval (see e.g., FIG. 39 A), experienced worse DSS induced colitis (see e.g., FIG. 39B-FIG. 39D and FIG. 39G-FIG. 39I). Similar to mice treated with EGF on DOL 10-21 to inhibit GAPs during the post-neonatal phase, CBir1 T cells adoptively transferred on DOL16 into mice lacking GCs or GAPs had significantly reduced Foxp3 expression and significantly increased inflammatory cytokines following disruption of the epithelial barrier with DSS (compare e.g., FIG. 37F and FIG. 37G with FIG. 39G, FIG. 39H, FIG. 39N and FIG. 39O). These data demonstrate that altering GAPs and the timing of gut bacterial antigen encounter in early life is a critical component to establish durable tolerance and limit inflammatory responses upon encounter later in life.

Discussion.

Here a specific pre-weaning interval was identified in which bacterial antigens are encountered by the colonic immune system. Surprisingly, in the course of normal development the immune system's encounter with some bacterial antigens is largely restricted to this interval in the post-neonatal phase of life. However, these events and their time-limited nature may not pertain to all gut bacterial antigens, as some bacteria in the fully developed gut microbiota may not be present during this interval, and gut bacteria closely adhering to the epithelium have been observed to generate antigen specific T cell responses outside of this interval in later life. Blocking the encounter of the immune system with bacterial products during this window resulted in failure to develop pTregs specific for antigens from these bacteria that was not compensated for by later encounters, indicating that the timing of these events is critical for developing tolerance to some gut bacteria. Further, initial encounter of these bacterial antigens outside of this interval or extending encounters beyond this interval resulted in the induction of effector T cell responses to gut bacteria. Thus, the encounter of antigens from some gut bacterial taxa during a specific pre-weaning interval is critical for the development of tolerance to members of the gut microbiota.

The microbiota drives the development of a long-lived population of pTregs in the pre-weaning colon, and that these pTregs can control effector responses. Superimposing our findings on these studies suggests that these pTregs can be specific microbial antigens encountered in the post-neonatal phase, and that these encounters serve to develop a long-lived pTreg population with the ability to control inflammatory responses. While a limitation of our study is that it is restricted to mice, it is notable that individuals with Crohn's disease make systemic immune responses to the CBir1 antigen, and it was observed that pTregs specific for CBir1 antigen were largely induced during the post-neonatal phase of life in mice. This indicates that the events identified in pre-weaning mice have relevance to humans and combined with observations that antibiotic use in the first year of life is associated with an increased incidence of asthma, allergy, and inflammatory bowel disease, strongly suggests that altering microbial antigen encounters during specific intervals in pre-weaning children increases the risk of disease.

Effective acquisition of luminal antigens by LP-MNPs was abrogated in the absence of GCs and correlated with the density of GAPs in all situations, and was not correlated with paracellular leak, villous M-cells, or the extension of TEDs by LP-MNPs. While it is not possible to entirely exclude contributions from these other pathways, and a limitation is that the pharmacologic and genetic manipulations may have other effects beyond altering GAPs, multiple strategies manipulating GAPs correlated with antigen acquisition by LP-MNPs strongly implicating that GAPs are major contributors to antigen acquisition in the pre-weaning intestine. The stratified mucus layer, which separates bacteria from the epithelium, develops in the first week of life. However, this mucus layer was not sufficient to prevent encounters of the colonic immune system with gut bacterial antigens. This suggests that bacterial antigens, as opposed to whole bacteria, are delivered via GAPs, or alternatively encounters with live bacteria occur in the proximal colon where the mucus layer is more permeable. The need to restrict the encounter of gut bacterial antigens with the immune system to a specific interval is not well understood. The need to limit encounters in the neonatal phase might be related to the limited diversity of the gut bacterial population and limited T cell repertoire. This might preclude developing a diverse and stable responding T cell population as well as Th2 skewing from T cells derived from fetal T cell precursors, resulting in unbalanced responses to gut bacterial antigens. The need to limit exposure to gut bacterial antigens after weaning, when the immune system is fully competent may be related to the complex environment in which these antigens are encountered, as it was observed that inappropriate exposure to gut bacterial antigens post-weaning does not result in the induction of pTregs, and previous observations indicate these encounters result in inflammatory responses. In total, these observations indicate that timing of exposure is a critical component to the development of tolerance to some gut bacterial antigens, and highlights the unique and time-limited events occurring in the pre-weaning GI tract.

The gut microbiota contributes to multiple facets of health, and dysbioisis of the gut microbiota is implicated to contribute to multiple diseases. Interactions of the gut microbiota with the immune system shape each other resulting in co-development of these two organs, and accordingly these interactions are important to establish a stable relationship that is able to withstand transient perturbations by either member. In fact, the unstable relationship between the immune system and the gut microbiota, characterized by reciprocal inappropriate inflammatory responses and dysbiosis, is believed to underlie the pathogenesis of IBD. Here it was demonstrated that the encounters of bacterial antigens with the immune system that establish this relationship are much more complex than previously appreciated and extend beyond the mere presence of specific bacterial taxa in the lumen and responding T cells in the immune compartment. For antigens from some bacterial taxa, these encounters initially occur, and are largely limited to, a specific interval in early life, which is critical for developing tolerance to these bacteria and fostering a stable relationship with gut microbiota.

Materials and Methods.

Mice: All mice were ten generations or greater on the C57BL/6 background, with the exception of mAChr4$^{f/f}$ mice, which were six or more generations on the C57BL/6 background. C57BL/6 mice, OTII T cell receptor transgenic mice, and CD11c$^{YFP}$ transgenic mice, Math1$^{f/f}$ mice, Myd88$^{f/f}$ mice, Math1$^{PGRCre}$ mice were purchased from The Jackson Laboratory (Bar Harbor, ME) and bred and maintained in house. EGFR$^{f/f}$ mice were a gift from Dr. David Threadgill (University of North Carolina, Chapel Hill, N.C.). Myd88$^{-/-}$ mice, a gift from Dr. Akira (Osaka University, Osaka, Japan), were bred onto the C57BL/6 background by the Speed Congenics Facility of the Rheumatic Diseases Core Center, and maintained in house. mAChR4$^{f/f}$ mice were a kind gift from Jurgen Wess (National Institute Health, Bethesda, Md.). CBir1 TCR transgenic mice and DP1 transgenic mice have been previously described. Transgenic mice bearing a tamoxifen-dependent Cre recombinase expressed under the control of the villin promoter (vil-Cre-ER$^{T2}$) mice were a gift from Sylvie Robine (Institut Curie, Paris, France). To deplete Myd88, EGFR, or mAChR4 in GCs, mice were bred to generate Myd88$^{f/f}$Math1$^{PGRCre}$ mice, EGFR$^{f/f}$Math1$^{PGRCre}$ mice, and mAChR4$^{f/f}$ Math1$^{PGRCre}$ mice. These mice and Cre negative littermate controls were injected i.p. with mifepristone (10 mg/kg) every day starting four days prior to use in experiments. Generation of Math1 ERT2$^{ViCre}$ mice and inducible deletion of GCs by treatment with tamoxifen has been previously described. Mice used in these experiments were bred in house and weaned at DOL 21. Cohoused littermates were used as experimental groups and controls to minimize differences in the gut microbiota. For pharmacologic manipulations, littermates of the same sex were assigned a cage which contained animals of all treatment groups. For genetic manipulations, cages of weaned mice contained littermates of the same sex and both genotypes. Animal procedures and protocols were carried out in accordance with the institutional review board at Washington University School of Medicine.

Statistical Analysis: Data analysis using a student's t test or one-way ANOVA with a Dunnett or Tukey test to correct for multiple comparisons was performed using GraphPad Prism (GraphPad Software Inc., San Diego, Calif.). Biologic variables measured were normally distributed. Test for significance were two-sided. Alpha of p value <0.05 was considered significant.

Isolation of cellular populations and flow cytometry: Small intestines or colons were harvested, rinsed with PBS, and Peyer's patches or colonic patches were removed. Epithelial cellular populations were released by incubating for 15 min three times in a 37° C. rotating incubator in HBSS media (BioWhittaker, Walkersville, Md.) containing 5 mM EDTA as previously described. Isolation of splenic, MLN and lamina propria (LP) cellular populations was performed as previously described. In some experiments, single cell suspensions of MLN were cultured in cell culture media for three days as previously described. The first wash of HBSS+ EDTA was used to isolate goblet cells as below. Antibodies used for analysis are listed in TABLE 1. SI and colonic LP-MNPs were identified as 7AAD$^-$, CD45$^+$, CD11c$^+$, MHCII$^+$for flow cytometric sorting. Goblet cells were identified as CD45⁻, CD24⁻CK18⁺, UEA-I⁺ for flow cytometric sorting as previously described. For intracellular antigens and cytokines, cells were fixed and permeabilized overnight and stained per the manufacturers recommendations (eBioscience). Flow cytometry was performed with a FACScan cytometer (BD Biosciences, San Jose, Calif.) retrofitted with additional lasers. Data acquisition was performed using CellQuest (BD Biosciences) and Rainbow (Cytek,Fremont, Calif.) or FlowJo software (Tree Star, Ashland, OR). Data analysis was performed on a Macintosh computer running FlowJo software.

Analysis of luminal fluorescent Ova delivery to LP-DCs: 200 µg of Ova conjugated Alexafluor-647 (Molecular Probes) was injected in the SI on colonic lumen and two hours later cell populations were isolated from the SI and colonic LP and analyzed by flow cytometry.

Immunohistochemistry: Immunohistochemistry was performed as previously described. Antibodies used for immunohistochemistry are listed in TABLE 1. Pseudo-colored black and white images from fluorescent microscopy were obtained with an axioskop 2 microscope using Axiovision software (Carl Zeiss, Thornwood, NY).

Paracellular leak assay: To detect paracellular leak fluorescein labeled dextran 4,000 MW (50 mg/mL) was gavaged into mice on DOL 18. Four hours later serum was collected and fluorescence was measured on a spectrometer.

Intravital two-photon (2P) microscopy: Mice were anesthetized using nebulized isofluorane in 95% $O_2$/5% $CO_2$. Intravital preparation of the intestine was performed as previously described. To detect GAPs, tetramethylrodamine labeled dextran 10,000 MW (10 mg/mL) or fluorescein labeled dextran 10,000 MW (10 mg/mL) and diamidino-2-phenylindole (DAPI; 10 mg/mL) were injected intraluminally 20 minutes prior to imaging and imaging was performed for up to one hour. Tissues were excited using a Ti:sapphire laser tuned to 890 nm (Chameleon XR, Coherent). Time-lapse imaging was performed with a custom-built 2P microscope running ImageWarp acquisition software (A&B Software, New London, Conn.). Epithelial integrity was assessed by dextran and DAPI staining as previously described. Following imaging, tissues were placed in 10% formalin buffered phosphate solution (Fisher Scientific) to fix dextrans in place to confirm 2P findings and for further analysis by immunofluorescence microscopy.

Enumeration of GAPs: GAPs were identified using in vivo two-photon imaging and imaging of fixed tissue sections and enumerated as previously described. The number of GAPs per GCs was quantified by immunofluorescence microscopy of tissues that were fixed following 2P imaging and stained with CK18 (abcam).

Measurement of cytokines, EGF, and immunoglobulins: Cytokines and EGF were measured using the using ELISAs for EGF (R&D systems), phosphorylated MAPK, phosphorylated EGFR, IL17 (eBioscience), IFNγ and IL-10, (R&D systems) per the manufacturers recommendations. Luminal EGF was measured in stomach, SI, and colonic contents; to isolate contents the stomach was opened and contents was added to 1 ml PBS. For SI and colonic contents, 1 ml of PBS was injected to one open end of the SI or colon using a 24 gauge gavage needle. Contents were then collected in a tube from the other open end of the SI or colon. Phosphorylated MAPK, and phosphorylated EGFR was measured on epithelial cells from the SI or colon isolated by one 15 minute wash with HBSS+EDTA as described above. Cytokines were measured on supernatants from cultured MLNs.

Quantitative real time polymerase chain reaction assay: GCs, identified as 7AAD⁻CD45⁻CD24⁻Cytokeratin 18⁺UEA-I⁺ and IECs identified as 7AAD⁻CD45⁻CD24⁻Cytokeratin 18⁻UEA-I⁻ were flow cytometrically sorted from the epithelial fraction of intestines directly into RLT buffer (Qiagen) for RNA extraction. RNA was extracted from epithelial cellular populations, treated with DNAse, and transcribed into cDNA using Superscript II reverse transcriptase (Invitrogen, Carlsbad, Calif.) according to the manufacturer's recommendations. Primers used for RT-PCR are listed in TABLE 2. The absolute copy number of the target was calculated from standards that were constructed as previously described.

Treatments to alter GAPs: Acute induction or inhibition of GAPs was performed as previously described. Mice were given 500 µg/kg tyrphostin AG1478 i.p. to inhibit of EGFR activation, 10 mg/kg U0126 i.p. to inhibit MAPK/ERK (MEK1/MEK2) activation, 150 µg/kg carbamylcholine (acetycholine analogue) i.p., 100 mg/kg tropicamide (mAChR4 selective antagonist) i.p., 1 µg recombinant murine EGF (Shenandoah) in 20 µl PBS intracolonic, 10 µg LPS intraluminally, or 100 µl stomach contents from a DOL10 mice intraluminally, or 100 µl heat killed cecal contents from SPF housed adult mice intraluminally. Reagents from Sigma Aldrich, St. Louis, Mo. unless otherwise noted.

LP-MNP/T cell co-culture: $1\times10^5$ flow cytometrically sorted splenic CD3+CD4+Vβ8.3+ CBir1 T cells or $1\times10^5$ flow cytometrically sorted splenic CD3⁺CD4⁺Vα2⁺Vβ5⁺ OTI T cells were cultured with $1\times1\times10^5$ CD45+ MHCII+ CD11c+ flow cytometrically sorted SI or colonic LP-MNPs isolated from mice two hours following intraluminal administration of 2 mg Ova or PBS. Some wells were cultured with 10 µg Ova or 10 µg CBir1 Flagellin as a positive control. After three days, cultured cells were counted and analyzed by flow cytometry to determine absolute number of transgenic cells to calculate fold increase of T cells.

Adoptive T cell Transfer: $10^5$ splenic CD4⁺ T cells from CD45.1 CBir1 TCR transgenic mice, CD45.1+ DP1 TCR transgenic mice, or CD45.1+ OTII TCR transgenic mouse were enriched by magnetic particles (Stemcell Technology, #19752 Vancouver, British Columbia, Canada) and injected i.v. into mice. In some experiments cells were labeled with CFSE prior to injection, and MLNs of recipient mice were analyzed three days posts transfer. Mice were analyzed seven days posts transfer to evaluate the presence of the transferred population in the LP. In some experiments, in FIG. 34, FIG. 37, and FIG. 39, cells were transferred on DOL 16, and analyzed on DOL 30 or after 8 days of DSS treatment on DOL 38.

DSS colitis: Mice were given DSS (36,000-50,000 MW, Reagent grade, MP Biomedicals) in drinking water ad libitum for eight days. Math1$^{fl/fl}$ ERT2$^{ViCre}$ mice and litter mates were given 1.5% DSS due to their increased susceptibility to disease. Weight was measured daily. On the final day, colons were measured for length to assess shortening, and were fixed in buffered formalin and embedded in paraffin for sectioning. H/E sections were scored for disease as before. In some experiments, colon LP was isolated on the final day of DSS treatment to analyze endogenous T cell and transferred CBir1 T cell populations.

Bacterial DNA extraction, 16s RNA Quantification, and sequencing: Colonic cecal contents were placed in 750 µl lysis buffer (200 mM NaCl, 100 mM Tris, 20 mM ETA, pH 8.0) with 200 mg 0.1 mm diameter zirconia silica beads (BioSpec, Bartlesville, Okla.), and vortexed on bead beater (MP Biomedicals, Fast prep 24) and DNA was isolated using the All prep DNA/RNA extraction kit (cat #80204, Qiagen, Valencia, Calif.). Quantification of the copies of 16s was performed using real time PCR and a standard curve, using the primers for total bacteria 5'-GGT-GAATACGTTCCCGG-3' (SEQ ID NO: 33) and 5'-TACGGCTACCTTGTTACGACTT-3' (SEQ ID NO: 34), the CBir1 flagellin epitope 5'-GCTGACACAGGAAATC-GATCGT-3' (SEQ ID NO: 35) and 5'-GAGAGTATACAT-CACCCGTCGCAT-3' (SEQ ID NO: 36) and B. Vulgatus 5'-AAGGGAGCGTAGATGGATG-3' (SEQ ID NO: 37) and 5'-CGAGCCTCAATGTCAGTTGC-3' (SEQ ID NO: 38). Metagenomic analysis of the bacterial communities using 16s rRNA sequencing was performed and analyzed as previously described.

What is claimed is:

1. A method for suppressing formation of goblet associated antigen passages (GAPs) in a human subject comprising: administering an effective amount of a composition comprising an epidermal growth factor receptor (EGFR) ligand and a diluent, wherein the composition does not comprise breast milk;

the EGFR ligand is administered to the subject over a time course of treatment in a multiple dosage regime;

the amount of the EGFR ligand administered decreases as the subject ages and the subject is an infant or child between about 0 days old (first day of life) and about two years old or about weaning age; and the subject has, is suspected of having, or is at risk for an allergic disorder, and administration of the composition results in a reduced immune response.

2. The method of claim 1, wherein the subject has an allergic disorder, and administration of the composition results in a reduced immune response.

3. The method of claim 2, wherein the allergic disorder is a food allergy.

4. The method of claim 1, wherein the method comprises oral administration of the composition comprising an EGFR ligand.

5. The method of claim 1, wherein
(i) the composition comprising an EGFR ligand is administered to the subject, wherein the EGFR ligand concentration in the composition is between about 0.02 µg/mL and about 0.2 µg/mL; or
(ii) the subject is between about 0 days old (day of birth) and about 1 year old, about 18 months old, or about two years old or between 0 days of age (first day of life) and about 140 days of age.

6. The method of claim 1, wherein the composition comprising the EGFR ligand is administered to the subject in an oral formulation.

7. The method of claim 6, wherein the oral formulation is selected from the group consisting of a food formulation, a powdered formulation, liquid formulation, and a capsule, including wherein the oral formulation is liquid dispensed in a dropper bottle, powdered infant formula, liquid concentrate infant formula, ready-to-use infant formula, or parenteral hyperalimentation, wherein the oral formulation is optionally used to supplement infant formula or breast milk.

8. The method of claim 1, wherein the EGFR ligand is selected from one or more of the group consisting of: EGF, transforming growth factor-a (TGFa), heparin-binding EGF-like growth factor (HB-EGF), amphiregulin (AR), betacellulin (BTC), epiregulin (EPR), hyaluronic acid, epigen, and other EGFR activator.

9. The method of claim 8, wherein the EGFR ligand is in an effective amount to:
reduce immune response toward an antigen;
modulate exposure to gut luminal substances;
modulate colonic antigen uptake or antigen exposure;
modulate luminal antigen delivery;
reduce bacterial translocation;
promote development of regulatory T-cells restraining Th2 responses;
promote RORγt+iTreg development and maintenance; or
modulate Th2 related immunoglobulins and cytokines.

10. A method of modulating antigen passage to outside of the intestines from the gut of a human subject comprising administering to the subject an effective amount of a composition comprising an EGFR ligand and a diluent,
wherein
the composition does not comprise breast milk;
the subject has, is suspected of having, or is at risk of developing an allergic disorder;
the EGFR ligand is administered to the subject over a time course of treatment in a multiple dosage regime and the amount of the EGFR ligand administered decreases as the subject ages; and
the subject is an infant or child between about 0 days old (first day of life) and about two years old or about weaning age.

11. The method of claim 10, wherein the EGFR ligand is in an effective amount to treat, prevent, or reduce the likelihood of developing a food allergy and the composition comprising an EGFR ligand is administered to the intestine.

12. The method of claim 10, wherein the composition is formulated in an oral formulation selected from the group consisting of: a food formulation, a powdered formulation, liquid formulation, and a capsule, including wherein the oral formulation is liquid dispensed in a dropper bottle, powdered infant formula, liquid concentrate infant formula, ready-to-use infant formula, or parenteral hyperalimentation, wherein the oral formulation is optionally used to supplement infant formula or breast milk.

13. The method of claim 10, wherein the EGFR ligand is selected from one or more of the group consisting of: EGF, transforming growth factor-a (TGFa), heparin-binding EGF-like growth factor (HB-EGF), amphiregulin (AR), betacellulin (BTC), epiregulin (EPR), hyaluronic acid, epigen, and other EGFR activator.

14. The method of claim 10, wherein the EGFR ligand is in an effective amount to:
reduce immune response toward an antigen;
modulate exposure to gut luminal substances;
reduce bacterial translocation;
modulate colonic antigen uptake or antigen exposure;
modulate luminal antigen delivery;
promote development of regulatory T-cells restraining Th2 responses;
promote RORγt+iTreg development and maintenance; or
modulate Th2 related immunoglobulins and cytokines.

15. A method for treating or reducing the likelihood of developing a food allergy in a human subject in need thereof, the method comprising: administering to the intestine an effective amount of a composition comprising an EGFR ligand and a diluent to the subject, wherein
the composition does not comprise breast milk;
the EGFR ligand is administered to the subject over a time course of treatment in a multiple dosage regime;
the amount of the EGFR ligand administered decreases as the subject ages; and
the subject is an infant or child between about 0 days old (first day of life) and about two years old or about weaning age.

16. The method of claim 15, wherein the EGFR ligand is selected from one or more of the group consisting of: EGF, transforming growth factor-a (TGFa), heparin-binding EGF-like growth factor (HB-EGF), amphiregulin (AR), betacellulin (BTC), epiregulin (EPR), hyaluronic acid, epigen, and other EGFR activator.

17. A method for suppressing formation of goblet associated antigen passages (GAPs) in a human subject or modulating antigen passage to outside of the intestines from the gut of a human subject comprising: administering to the intestine an oral formulation comprising a composition comprising an epidermal growth factor receptor (EGFR) ligand and a diluent,
wherein
the composition does not comprise breast milk;
the EGFR ligand is administered to the subject over a time course of treatment in a multiple dosage regime;
the amount of the EGFR ligand administered decreases as the subject ages and the subject is an infant or child between about 0 days old (first day of life) and about two years old or about weaning age;
the subject has, is suspected of having, or is at risk for necrotizing enterocolitis (NEC) or sepsis; and
administration of the composition results in a reduced immune response.

18. The method of claim 17, wherein the EGFR ligand is in an effective amount to treats, prevents, or reduce the likelihood of developing NEC.

19. The method of claim 17, wherein
(i) the composition comprising an EGFR ligand is administered to the subject, wherein the EGFR ligand concentration in the composition is between about 0.02 µg/mL and about 0.2 µg/mL; or
(ii) the subject is between about 0 days old (day of birth) and about 1 year old, about 18 months old, or about two years old or between 0 days of age (first day of life) and about 140 days of age.

20. The method of claim 17, wherein the oral formulation is selected from the group consisting of a food formulation, a powdered formulation, liquid formulation, and a capsule, including wherein the oral formulation is liquid dispensed in a dropper bottle, powdered infant formula, liquid concentrate infant formula, ready-to-use infant formula, or parenteral hyperalimentation, wherein the oral formulation is optionally used to supplement infant formula or breast milk.

21. The method of claim 17, wherein the EGFR ligand is selected from one or more of the group consisting of: EGF, transforming growth factor-a (TGFa), heparin-binding EGF-like growth factor (HB-EGF), amphiregulin (AR), betacellulin (BTC), epiregulin (EPR), hyaluronic acid, epigen, and other EGFR activator.

22. The method of claim 17, wherein the EGFR ligand is in an effective amount to:
reduce immune response toward an antigen;
modulate exposure to gut luminal substances;
modulate colonic antigen uptake or antigen exposure;
modulate luminal antigen delivery;
reduce bacterial translocation;
promote development of regulatory T-cells restraining Th2 responses;
promote RORγt+iTreg development and maintenance; or
modulate Th2 related immunoglobulins and cytokines.

23. The method of claim 17, wherein the subject is at risk of sepsis.

24. The method of claim 17, wherein the subject is at risk for NEC.

25. The method of claim 17, wherein the sepsis is late onset sepsis (LOS).

26. The method of claim 17, wherein the subject is a pre-term infant or neonate.

27. The method of claim 17, wherein the dosage is administered until the subject is 60 days old.

* * * * *